(12) United States Patent
Lakowicz et al.

(10) Patent No.: US 7,635,595 B2
(45) Date of Patent: Dec. 22, 2009

(54) FLUORESCENT PROBES FOR SACCHARRIDES

(76) Inventors: Joseph R. Lakowicz, 10037 Fox Den Rd., Elliott City, MD (US) 21042; Nicolas Dicesare, 935 Guyon Street, St. Charles de Drummod, Quebec (CA) J2C 8N3

(*) Notice: Subject to any disclaimer, the term of this patent is extended or adjusted under 35 U.S.C. 154(b) by 905 days.

(21) Appl. No.: 11/075,817

(22) Filed: Mar. 10, 2005

(65) Prior Publication Data

US 2005/0158245 A1 Jul. 21, 2005

Related U.S. Application Data

(63) Continuation of application No. 10/448,430, filed on May 30, 2003, now abandoned.

(60) Provisional application No. 60/383,799, filed on May 30, 2002.

(51) Int. Cl.
G01N 33/50 (2006.01)
G01N 21/64 (2006.01)
C07D 233/54 (2006.01)
C07F 5/04 (2006.01)
C07F 5/02 (2006.01)
A61B 5/00 (2006.01)

(52) U.S. Cl. ............... 436/94; 422/61; 436/95; 436/131; 436/172; 548/110; 558/286; 558/287; 558/288; 564/8; 564/9; 564/10; 564/11; 568/1; 568/6; 600/316; 600/317; 600/319

(58) Field of Classification Search ............ 250/485.1, 250/459.1; 422/61; 436/94–95, 131, 172; 600/316–317, 319; 548/110, 215, 235, 239; 558/286–288; 562/7; 564/8–11, 305; 568/1, 568/6

See application file for complete search history.

(56) References Cited

U.S. PATENT DOCUMENTS

| | | | | | |
|---|---|---|---|---|---|
| 2,710,874 | A | * | 6/1955 | Freund | 556/73 |
| 3,038,926 | A | * | 6/1962 | Farthouat | 558/288 |
| 3,222,379 | A | * | 12/1965 | Farthouat | 536/115 |
| 3,397,228 | A | * | 8/1968 | Brownstein | 562/7 |
| 3,567,439 | A | * | 3/1971 | Daniel et al. | 430/83 |
| 4,496,722 | A | * | 1/1985 | Gallop et al. | 544/69 |
| 5,108,502 | A | * | 4/1992 | Pawlowski et al. | 106/31.48 |
| 5,187,288 | A | * | 2/1993 | Kang et al. | 548/110 |
| 5,248,782 | A | * | 9/1993 | Haugland et al. | 548/110 |

(Continued)

FOREIGN PATENT DOCUMENTS

JP 7-145174 * 6/1995

OTHER PUBLICATIONS

Bauer, W. W. et al, Journal of the American Chemical Society 1924, 46, 1925-1931.*

(Continued)

*Primary Examiner*—Arlen Soderquist
(74) *Attorney, Agent, or Firm*—Rothwell, Figg, Ernst & Manbeck, P.C.

(57) ABSTRACT

The spectroscopic and photophysical properties of fluorescent probes comprising donor-acceptor derivatives comprising the boric acid group or a derivative of boric acid, $B(OH)_3$ (or borate ion, $BO(OH)_2^{-1}$), arsenious acid, $H_3AsO_3$ (or arsenite ion, $H_2AsO_3^{-1}$), telluric acid, $H_6TeO_6$ (or tellurate ion, $H_5TeO_6^{-1}$) or germanic acid, $Ge(OH)_6$ (or germanate ion, $GeO(OH)_3^{-1}$) are described. Method of using said probes are also provided.

19 Claims, 27 Drawing Sheets

U.S. PATENT DOCUMENTS

| | | | | |
|---|---|---|---|---|
| 5,274,113 | A * | 12/1993 | Kang et al. | 548/405 |
| 5,338,854 | A * | 8/1994 | Kang et al. | 548/110 |
| 5,446,157 | A * | 8/1995 | Morgan et al. | 546/13 |
| 5,503,770 | A * | 4/1996 | James et al. | 252/301.16 |
| 5,512,246 | A | 4/1996 | Russell | |
| 5,631,364 | A * | 5/1997 | Sundrehagen et al. | 540/128 |
| 5,981,746 | A * | 11/1999 | Wolfbeis et al. | 540/450 |
| 6,001,999 | A * | 12/1999 | Wolfbeis et al. | 540/468 |
| 6,002,954 | A | 12/1999 | Van Antwerp | |
| 6,011,984 | A | 1/2000 | Van Antwerp | |
| 6,106,999 | A * | 8/2000 | Ogiso et al. | 430/281.1 |
| 6,232,467 | B1 * | 5/2001 | Petasis et al. | 506/27 |
| 6,319,540 | B1 | 11/2001 | Van Antwerp | |
| 6,475,670 | B1 | 11/2002 | Ito | |
| 6,534,316 | B2 * | 3/2003 | Strongin et al. | 436/94 |
| 6,627,177 | B2 * | 9/2003 | Singaram et al. | 424/9.6 |
| 6,682,938 | B1 * | 1/2004 | Satcher et al. | 436/172 |
| 6,766,183 | B2 * | 7/2004 | Walsh et al. | 600/317 |
| 2002/0043651 | A1 * | 4/2002 | Darrow et al. | 252/408.1 |
| 2002/0094586 | A1 * | 7/2002 | Daniloff et al. | 436/518 |

OTHER PUBLICATIONS

Worrall, D. E., Journal of the American Chemical Society 1930, 52, 664-669.*

Doak, G. O. et al, Journal of the American Chemical Society 1942, 64, 1064-1066.*

Suenaga, H. et al, Tetrahedron Letters 1995, 36, 4825-4828.*

Muller, M. et al, Angewandte Chemie, International Edition in English 1996, 35, 886-888.*

Superchi, S. et al, Organic Letters 1999, 1, 2093-2096.*

B. Appleton, et al, "Detection of total sugar concentration using photoinduced electron transfer materials: development of operationally stable, reusable optical sensors", Sensors and Actuators B, vol. 65, 2000, pp. 302-304.

K. Berndt, et al., "Phase-modulation fluorometry using a frequency-doubled pulsed laser diode light source", Rev. Sci. Instrum. vol. 61, No. 7, Jul. 1990, pp. 1816-1820.

R. Corriu, et al., "Unsaturated polymers containing boron and thiophene units in the backbone", Chem. Commun., 1998, pp. 963-964.

S. D'Auria, et al., "The fluorescence emission of the Apo-glucose Oxidase from *Aspergillus niger* as Probe to Estimate Glucose Concentrations", Biochemical and Biophysical Research Communications, vol. 263, 1999, pp. 550-553.

N. DiCesare, et al., "Evaluation of Two Synthetic Glucose Probes for Fluorescence-Lifetime-Based Sensing", Analytical Biochemistry, vol. 294, 2001, pp. 154-160.

Z. Diwu, et al., "A Facile Protocol for the Convenient Preparation of Amino-substituted α-Bromo- and α-α-Dibromo Arylmethylketones", Tetrahedron Letters, vol. 39, 1998, pp. 4987-4990.

J. Hartley, et al., "Synthetic receptors", J. Chem. Soc., Perkin Trans. vol. 1, 2000, pp. 3155-3184.

K. Hirai, et al., "Reactions and Kinetics of (2,4,6-Tri-tert-butylphenyl)phenylcarbene", The Chemical Society of Japan, Chemistry Letters, 1994, pp. 503-506.

C. Hutchinson, et al., "Fluorescence Lifetime-Based Sensing in Tissues: A Computational Study", Biophysical Journal, vol. 68, Apr. 1995, pp. 1574-1582.

T. James, "Novel Saccharide-Photoinduced Electron Transfer Sensors Based on the Interaction of Boronic Acid and Amine", J. Am. Chem. Soc., 1995, vol. 117, pp. 8982-8987.

T. James, "A saccharide 'sponge'. Synthesis and properties of a dendritic boronic acid", Chem. Commun., 1996, pp. 705-706.

J. Lakowicz, et al., "Anisotrophy-Based Sensing with Reference Fluorophores", Analytical Biochemistry, vol. 267, 1999, 397-405.

B. Lee, et al., "Boratastilbene: Synthesis, Structural Characterization, and Photophysics", J. Am. Chem. Soc., vol. 122, 2000, pp. 3969-3970.

N. Matsumi, et al., "Synthesis of Organoboron π-Conjugated Polymers by Hydroboration Polymerization between Heteroaromatic Diynes and Mesitylborane and Their Light Emitting Properties", Macromolecules, vol. 32, 1999, pp. 4467-4469.

N. Matsumi, et al., "Poly($p$-phenylene-borane)s. Novel Organoboron πConjugated Polymers via Grignard Reagent", J. Am. Chem. Soc., vol. 120, 1998, pp. 10776-10777.

D. Rehm et al., "Kinetics of Fluorescence Quenching By Electron and H-Atom Transfer", Israel Journal of Chemistry, vol. 8, 1970, pp. 259-271.

K.R.A. S. Sandanayake, et al., "Two Dimensional Photoinduced Electorn Transfer (PET) Fluorescence Sensor for Saccharides", Chemistry Letters, 1995, pp. 503-504.

H. Shinmori, et al., "Spectroscopic Sugar Sensing by a Stilbene Derivative with Push ($Me_2N$-)-Pull (($HO)_2B$-)-Type Substituents", Tetrahedron, vol. 51, No. 7, 1995, pp. 1893-1902.

P. Sienkiewicz, et al., "Chemical Affinity Systems-l, pH Dependence of Boronic Acid-Diol Affinity in Aqueous Solution", J. Inorg. Nucl., Chem. vol. 42, 1980, pp. 1559-1575.

A. Singh, et al., "α, $w$-Diphenylpolyenes Capable of Exhibiting Twisted Intramolecular Charge Transfer Fluorescence: A Fluorescence and Fluorescence Probe Study of Nitro- and Nitrocyano-Substituted 1,4-Diphenylbutadienes", J. Phys. Chem. A, vol. 104, 2000, pp. 464-471.

Y. Sonoda et al., Substituent Effect on the *cis-trans* Photoisomerization of *trans,trans,trans*-1,6-Diphenyl-1,3,5-hexatrienes, The Chemical Society of Japan, Chemistry Letters, 1998, pp. 349-350.

H. Suenaga, et al., "Screening of boronic acids for strong inhibition of the hydrolytic activity of α-chymotrypsin and for sugar sensing associated with a large fluorescence change", Pure & Appl. Chem., vol. 68, No. 11, 1996, pp. 2179-2186.

H. Szmacinski, et al., "Fluorescence lifetime-based sensing and imaging", Sensors and Actuators B, vol. 29, 1995, pp. 16-24.

H. Szmacinski, et al., "Lifetime-Based Sensing", Topics in Flurescence Spectroscopy, vol. 4: Probage Design and Chemical Sensing, Chap. 10, pp. 295-334.

M. Takeuchi, et al., "Fluorescence and CD Spectroscopic Sugar Sensing by a Cyanine-appended Diboronic Acid Probe", Tetrahedron, vol. 52, No. 4, 1996, pp. 1195-1204.

R. Thompson, et al., "Phase Fluorometry Using a Continuously Modulated Laser Diode", Anal. Chem., vol. 64, 1992, pp. 2075-2078.

W. Wang, et al., "Building Fluorescent Sensors by Template Polymerization: The Preparation of a Fluorescent Sensor for d-Fructose", Organic Letters, vol. 1, No. 8, 1999, pp. 1209-1212.

J. Yoon, et al., "Fluorescent Chemosensors of Carbohydrates. A Means of Chemically Communicating the Binding of Polyols in Water Based on Chelaton-Enhanced Quenching", J. Am. Chem. Soc., vol. 114, 1992, pp. 5874-5875.

* cited by examiner

FLUORESCENT PROBES FOR SACCHARRIDES

CROSS-REFERENCE TO RELATED APPLICATION

The present application is a continuation of application Ser. No. 10/448,430, filed May 30, 2003, which is related to and claims priority under 35 U.S.C. § 119(e) to U.S. provisional patent application Ser. No. 60/383,799, filed May 30, 2002, which is incorporated by reference herein in its entirety, along with the references cited therein.

This invention was made with partial government support and as a result of this finding, the United States Government may have certain rights in this invention.

FIELD OF THE INVENTION

This invention relates generally to the field of fluorescent probes. More specifically, the invention relates to electron-donor and electron acceptor pairs that possess a boronic acid group or boronic, arsenious, germanic and telluric acid derivatives and methods of use of such compounds as sensors for detecting the presence of sugars.

The publications and other materials used herein to illuminate the background of the invention or provide additional details respecting the practice are incorporated by reference and for ease of reference are included in the attached Bibliography.

BACKGROUND AND SIGNIFICANCE

For more than a decade, the development of synthetic probes for the recognition and analysis of sugars has attracted much attention. Synthetic probes could find useful applications in the food industry as well as in the clinical analysis. Detection and monitoring of glucose is particularly important for diabetics. The use of enzymes shows some limitations in the development of implantable sensors for continuous glucose monitoring in blood or interstitial tissue. Continuous monitoring of glucose blood level is very important for the long term health of the diabetics and could lead to important medical technology such as a blood sugar alarm system and an in vivo control device for an implanted insulin pump.

The boronic acids have been known for their ability to interact with diols (1). In addition, boronic, arsenious, germanic and telluric acid derivatives are known to exhibit similar characteristics (See e.g., U.S. Pat. No. 5,512,246). These compounds have been used for the development of receptor and fluorescent probes for sugars (2-4). One advantage of using boronic acid as a chelator group for sugars is the compound's fast and reversible interaction with sugars. In addition, many substituted phenylboronic acids are commercially available, which would allow for the development of a large diversity of synthetic fluorescent probes for sugars with minimal synthetic steps. Depending on the structure of the molecule and on the number of boronic acid group present, association constants from micromolar to tens of millimolar can be obtained and chiral discrimination can also be observed. Delivery systems for insulin have also been developed using boronic acid gel (5-6).

Determination of the glucose concentration is crucial for people with diabetes. Large variation in the glucose level in blood could result in important medical problems including cardiovascular disease, neuropathies and blindness. Non-invasive measurement of blood glucose has been a long-standing research goal and a wide variety of such methods have been describe in the literature, including near-infrared spectroscopy, optical rotation, amperometric, calorimetric, and fluorescence detection (7-20). Despite some promising results, these methods show limitation as important background with the NIR (Near infra red) technique and low optical rotation and important depolarization du to the tissue with the optical rotation technique. Enzymes and proteins are widely use in the research for the development of glucose sensors. At present, the most reliable method to measure blood glucose is by finger stick and subsequent glucose measurement, typically by glucose oxidase. A competitive glucose assay using fluorescence resonance energy transfer between concanavalin A and dextran has been developed and efforts are also underway to develop methods for the use of intrinsic fluorescence changes using thermophilic enzymes. Proteins and enzymes show an affinity constant comparable with blood glucose level, show a great selectivity and are biocompatible. Despite these advantages, they exhibit low stability (to heat and organic solvents), solubility problems and are difficult to modify. Thus, the development of a synthetic glucose sensor is greatly desirable and the flexibility of organic compounds as probes could allow a wide range of possibilities for the development of a non-consuming glucose device.

In treating diabetic patients, the aim is to tightly regulate the plasma glucose level within the normal physiological range (80-120 mg/dL), so that diabetic adverse effects can be avoided. As an aid to diabetes therapy, continuous monitoring of blood glucose concentrations in vivo has long been recognized as a major objective as a future tool in the fight against diabetes. During the past decade, intense effort has been directed toward the development of glucose monitoring biosensors as an aid to diabetes therapy. Development of an implantable glucose sensor that is specific to glucose and sensitive enough to precisely measure glucose levels in vivo would be a significant advance in the treatment of diabetes. Such ability to more closely control blood glucose levels would also be useful in insulin delivery system responsive to glucose levels in diabetic patients. Glucose biosensor systems have recently been described which employ glucose binding molecules attached to a polymeric hydrogel for example (See. e.g., U.S. Pat. No. 6,475,670).

For several decades, fluorescence spectroscopy has been widely use for the detection and analysis of different analytes (20-22). Wavelength-ratiometric, fluorescence lifetime based sensing and polarization assays (24-26) are some techniques available for the detection and analysis of analytes by fluorescence spectroscopy. Fluorescence techniques for glucose recognition have been used most of the time with enzymes and proteins. Despite some promising results, enzymes and proteins show some stability problems against organic solvents and heat. In contrast, synthetic organic probes show high stability and flexibility due to the versatility of the organic synthesis. Modification of the probe structure could lead to a modification of the affinity for the analyte, of the wavelength of emission of the probes and of the immobilization of the probes on a support for the building of a sensor.

The use of the intramolecular charge transfer (ICT) involving the boronic acid is a very promising technique for rapid monitoring of sugar levels. ICT is well known to be very sensitive to small perturbations that can result in spectral shifts, intensity changes and/or lifetime changes. In addition, ICT can be applied to a large diversity of fluorophores without limitation of the wavelength range and/or lifetime of the fluorophore. The boronic acid group has been known for 40 years for the ability to form complexes with polyols. This ability led Yoon et al. to build a fluorescence probe for sugar based on the boronic acid group. S. Shinkai, T. D. James and collaborators have developed and studied some molecular structures and fluorescence probes involving the boronic acid group (27-33). They have developed fluorescence probes involving different mechanisms to induce spectral changes. Molecular rigidification, photoinduced electron transfer (PET) and excimer formation are some examples (34-36). Despite these interesting studies, most of the fluorescence probes developed up to now show emission in the ultraviolet region and/or involved a mechanism limited to few fluorophores.

Photoinduced electron transfer (PET) is often used as mechanism for fluorescence quenching in the development of sensors. This quenching is due to the presence of the amino group near the chromophore. When an analyte (ions for almost all cases) binds the probe, the interaction between the analyte and the nitrogen's lone pair of electrons removes the quenching and results in a detectable increase of the fluorescence of the probe. This mechanism has been applied with an anthracene derivative with amino and phenyl boronic acid groups for glucose probes. Upon the binding between the boronic acid group and the saccharide, the pKa of the boron atom decreases. This decrease improves the interaction between the boron atom and the nitrogen atom of the amino group and thus reduces the PET quenching of the chromophore. Increase of the fluorescence intensity up to seven time can be observed. These anthracene probes for saccharide have also been successful adapted to build polymers for the development of a device (37-38). Until now, however, no system and analysis using the fluorescence lifetime could be found for these systems.

Recent interest in the boron-aromatic systems stems from the concept of π-electron aromaticity and conjugation across $sp^2$-hybridized boron. Recent reports highlight the potential use of boron-containing conjugated polymers in the emerging optoelectronic applications. Lee et al. investigated the effect of the B⁻-for-C substitution on the photophysics and photochemistry of borastilbenes and borastyrylstilbenes (39-40). The phenyl boronic acid group [phe-B(OH)$_2$] has attracted interest for its ability to covalently bind diols and sugars. Lorand et al. investigated the structure of the neutral and anionic forms [phe-B(OH)$_3^-$] of the phenylboronic acid group. Their results showed that the neutral form of the boronic acid group linked to the phenyl moiety has a planar triangular conformation with a $sp^2$-hybridized boron atom. On the other hand, the anionic form has a tetrahedral conformation with a $sp^3$-hybridized boron atom. Two research groups have investigated the effect of this change on the emission of fluorophores in order to evaluate their use for the development of fluorescent probes for saccharides. Yoon et al. examined anthrylboronic acid and Suenaga et al. analyzed naphthyl, biphenyl, pyrenyl and stilbeneboronic acid. In the case of the anthrylboronic acid, a decrease of 40% of the emission intensity was observed following the formation of the anionic form of the boronic acid group. Complexation of the boronic acid moiety with saccharides decreases the p$K_a$ of boronic acid group, 8.8 to 5.9 in saturated fructose solution. As a result, complexation with the saccharide induces the formation of the anionic form of the boronic acid and then a decrease of the emission intensity. This decrease is relatively small, 30% for fructose and about 10% for glucose. Suenaga et al. observed similar results. For this reason, the direct insertion of the boronic acid group on a fluorophore has not been deeply investigated.

Several laboratories have investigated the ability of the boronic acid group to interact with amino groups. Fluorescence probes based on a decrease of the photoinduced electron transfer (PET) of amino-substituted fluorophores, mainly anthracene, have been synthesized (42). This mechanism resulted in a significant intensity increase, up to 7-fold, and a fluorescence lifetime change after binding saccharides. Molecular rigidification induced by saccharides interaction using the boronic acid group as a chelator group has also been used with a cyanine dye for the development of fluorescence probes. Excimer formation between two pyrene moieties has also been used. Despite these interesting approaches to use the combination of the boronic acid group and fluorophores, they are mostly restricted to a few fluorophores. The PET mechanism is expected to be ineffective for long wavelength fluorophore use (43). Rigidification and excimer formation can be applied only to few fluorophores.

One objective of the invention is to provide compounds which are useful as fluorescent probes for the detection of sugars. Another objective of the invention is to provide fluorescent probes that are useful for the detection of sugars based on lifetime fluorescence, changes in fluorescent intensity, spectral shifts and/or wavelength-ratiometric measurements.

The present invention fulfils these needs and realizes these and other objectives. Other advantages of the invention are further apparent from the disclosure provided.

SUMMARY OF THE INVENTION

In one embodiment, the present invention provides fluorescence probes based on the ICT mechanism involving the boric acid group or a derivative of boric acid, B(OH)$_3$ (or borate ion, BO(OH)$_2^{-1}$), arsenious acid, H$_3$AsO$_3$ (or arsenite ion, H$_2$AsO$_3^{-1}$), telluric acid, H$_6$TeO$_6$ (or tellurate ion, H$_5$TeO$_6^{-1}$) or germanic acid, Ge(OH)$_6$ (or germanate ion, GeO(OH)$_3^{-1}$), which bind to the vicinal hydroxyl groups of compounds containing such groups such as carbohydrates. The term "carbohydrate" as used herein, refers to compounds bearing a plurality of hydroxyl groups and one or more functional groups (particularly aldehyde, ketone, alcohol and/or acid moieties). Carbohydrates can be monomeric such as glucose, oligomeric or polymeric through acetal or glycosidic linkages.

In one embodiment, the invention provides compounds useful as fluorescent probes that are represented by the represented by the formula

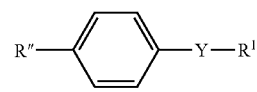

wherein $R^1$ represents the boric acid group or a derivative of boric acid, B(OH)$_3$ (or borate ion, BO(OH)$_2^{-1}$), arsenious acid, H$_3$AsO$_3$ (or arsenite ion, H$_2$AsO$_3^{-1}$), telluric acid, H$_6$TeO$_6$ (or tellurate ion, H$_5$TeO$_6^{-1}$) or germanic acid, Ge(OH)$_6$ (or germanate ion, GeO(OH)$_3^{-1}$); Y represents a compound of the formula

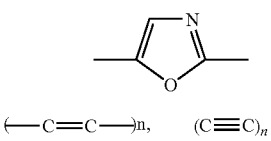

or a phenyl group.

and wherein $R^3$ represents a compound selected from the group consisting of H, $N(CH_3)_2$, CN and $OCH_3$ or other groups as well known in the art that are capable of donating or accepting electrons from an aromatic system; and n is a whole number from 1 to 5.

In one embodiment, the invention provides compounds which can be used as fluorescent probes to detect sugars wherein the probes are derived from stilbene derivatives which contain a boronic acid group.

In another embodiment, the invention provides compounds which can be used as fluorescent probes to detect sugars wherein the probes are derived from diphenylbutadiene or diphenylhexatriene substituted with the dimethylamino group as electron-donor group in a position para one of the phenyl group and the boronic acid group as the electron-withdrawing group in a position para of the other phenyl group.

In another embodiment, the invention provides compounds which can be used as fluorescent probes to detect sugars wherein the probes are derived from diphenyloxazole derivatives substituted with the dimethylamino group as electron-donor group in a position para one of the phenyl group and the boronic acid group as the electron-withdrawing group in a position para of the other phenyl group. Other groups well known to be capable of charge transfer interations with the boronic acid are also considered as part of the present invention.

In another embodiment, the invention provides compounds which can be used as fluorescent probes to detect sugars wherein the probes are anthracene derivatives substituted in a position meta of the phenyl group with a boronic acid group as the electron-withdrawing group.

In another embodiment, the invention provides compounds which can be used as fluorescent probes to detect sugars wherein the probes are functionalized boron-dipyrromethane with a boronic acid group as the electron-withdrawing group.

In another embodiment the invention provides a method of detecting the presence of a sugar in a solution which comprises adding a compound of the present invention comprising a boronic acid group to said solution and detecting a change in fluorescence in the compound, the fluorescence change resulting from the interaction of the boronic acid compound with the sugar. In a preferred embodiment, the change in fluorescence results from the boronic acid group interactions with the sugar.

In another embodiment, the method of detecting the presence of the sugar is performed in vivo in an animal. In one preferred embodiment, the method is performed in vivo in a human.

In yet another embodiment, the detection of a sugar in solution comprises the utilization of a fluorescent probe having a boronic acid group as an electron withdrawing group, wherein said probe is bound to a solid support in an animal.

In another embodiment, the invention provides a method of detecting the presence of a sugar in an animal wherein the lifetime fluorescence of the probe in the presence of the sugar is determined.

In another embodiment, the invention provides a method of detecting the presence of a sugar in vitro or ex vivo, wherein a sample is removed from an animal prior to testing of said sample. Thus, in another embodiment the invention provides kits for testing for the presence of a sugar which comprise a compound as described herein.

In another embodiment, the invention provides a method of detecting the presence of a sugar in an animal wherein a change in the fluorescent intensity of the probe in the presence of the sugar is detected.

In another embodiment, the invention provides a method of detecting the presence of a sugar in a transparent media such as the lens of the eye. In a preferred embodiment, the invention comprises a contact lens containing a compound described herein, wherein the contact lens comprising the compound can be used to detect the presence of a sugar in the eye of an animal.

In another embodiment, the intention provides methods for in vitro or ex vivo monitoring for the presence of sugars.

In another embodiment, the invention provides kits which comprise compounds of the present invention or other compounds useful in practicing the methods of the present invention and instructions for practicing the methods of the present invention to detect diols.

In another embodiment, the invention provides a method for detecting the presence of a sugar in a sample which comprises adding a fluorescent probe compound to the sample and measuring a change in the intensity ratio of the compound in response to the sugar.

DETAILED DESCRIPTION OF THE INVENTION

Figure 1A:
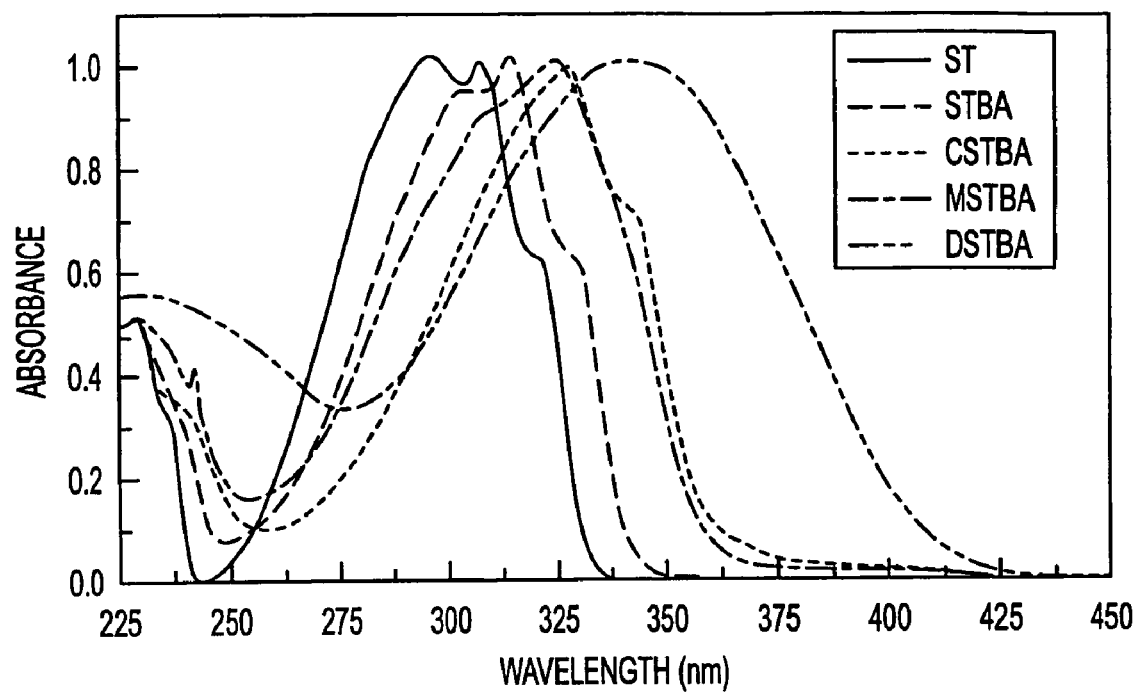
FIG. 1(A) is a graphical representation of the absorption and emission spectra of the stilbenes investigated in water/methanol 1:1 (v/v) at room temperature.

In an attempt to extend the usefulness of fluorescent probes for saccharides based on the boronic acid group, we investigated the possibility of using excited state charge transfer (CT) between the boronic acid moiety and a donor and/or acceptor groups. The excited charge transfer phenomenon has been widely used and described in the development of many luminescent probes for ions. As discussed above, the $sp^2$-hybridized boron atom inserted directly on the fluorophore shows resonance with the aromatic system of a chromophore as shown in the following representative reaction schemes:

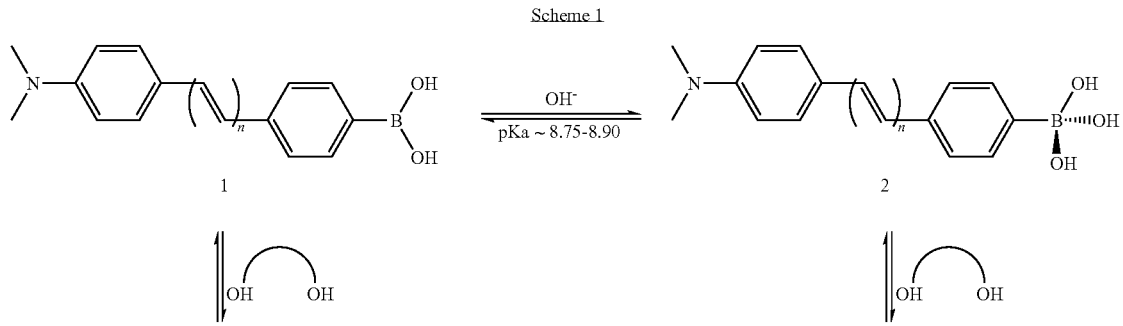

Scheme 1

-continued

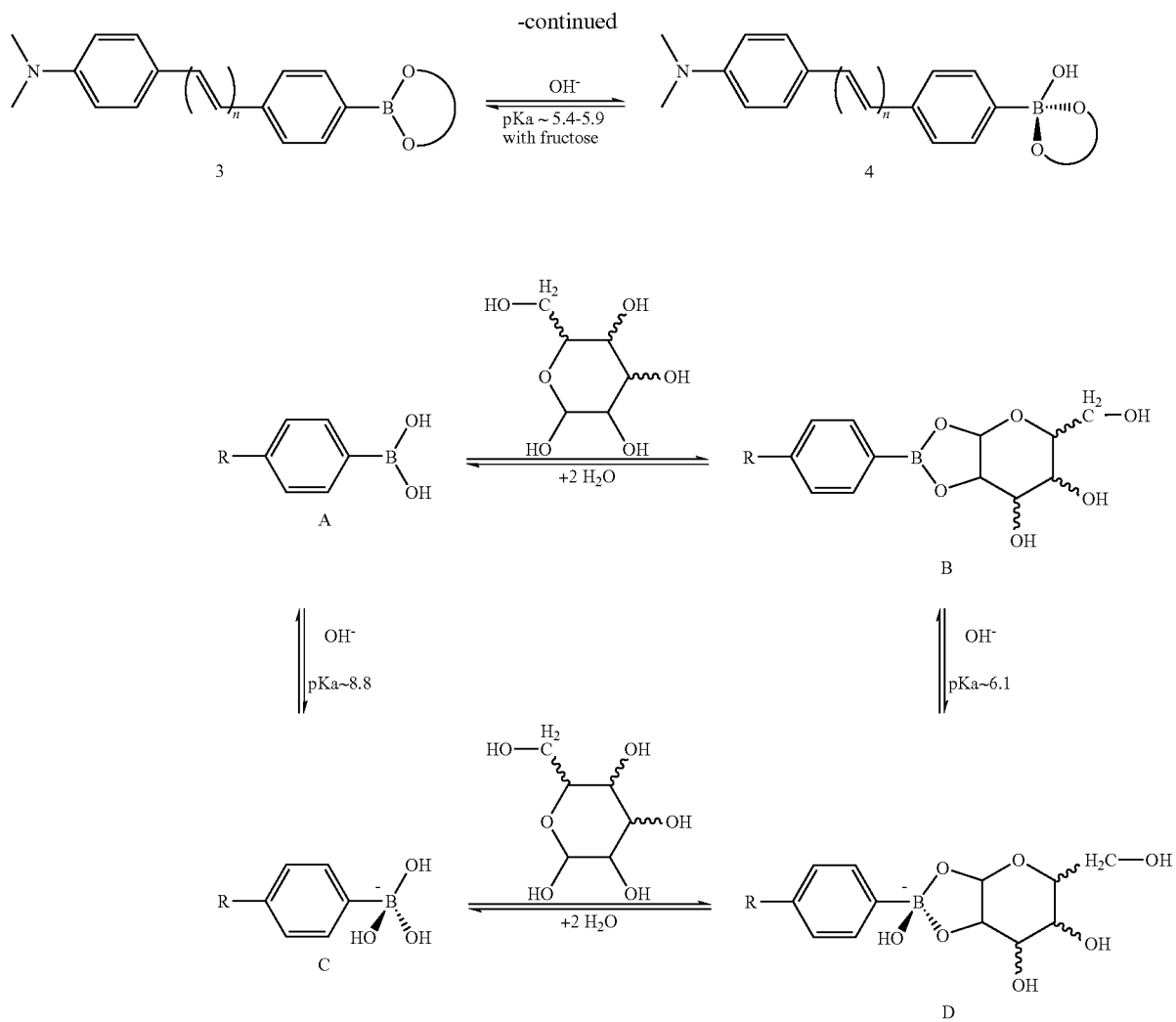

Excited-state charge transfer (CT) can be observed when the boronic acid group and an electron-donor group are present on the same fluorophore. In this case, the boronic acid group [—B(OH)$_2$] acts as an electron-withdrawing group. Following the interaction with sugar, the pK$_a$ of the boronic acid decreases and between pH 7 and 8, the boronic acid group is present in its anionic form [—B(OH)(sugar)]$^-$. The anionic form of the boronic acid group is no longer an electron-withdrawing group and spectral changes are observed due to reduced charge transfer. These spectral changes can be used for wavelength-ratiometric method for the detection and analysis of sugars. These results were obtained using substituted stilbenes in positions 4 and 4' as a molecular model. This CT mechanism can be applicable to a wide variety of fluorophores and especially to long wavelength emission fluorophores.

Because of the empty p orbital present on the boron atom, the boronic acid group should act as an electron acceptor group. The incorporation of a donor group on the same chromophore should result in excited charge transfer. As the boron with a sp2-hybridization changes to a sp3-hybridization for the anionic form (compound 2 in Scheme 1), the boronic acid group is no longer an electron acceptor group. This should lead to a change in the spectroscopic and photophysical properties of the probes. At pH 7-8, the form 1 (Scheme 1) should be dominant in solution, after the addition of sugar compound 4 should become predominant as the pK$_a$ of the boronic acid group decreases following the complexation with sugar. The difference in the hybridization of (forms 1 and 4 of scheme 1) should result in a change of the optical properties of the probes induced by the presence of sugar. This would lead to new fluorescent probes for sugar sensing. Also, the CT mechanism is applicable to a wide range of different luminescent probes and not restricted to only some probes as for the PET, rigidification or excimer mechanism.

The probes and methods of the present invention are applicable to detection of sugars in a transparent media, such as for example the lens and fluid of the eye. Thus, in one embodiment, the invention provides a method for monitoring glucose levels in a transparent media wherein the media is the fluid surrounding the eye. In one embodiment, the invention provides a method for monitoring glucose levels in the eye wherein the compounds of the present invention are attached to a contact lens for in situ glucose monitoring in the eye.

The present invention further provides methods for in vitro or ex vivo monitoring. Thus, as well readily be recognized by those of ordinary skill in the art, the compounds and methods of the present invention can be employed to detect and monitor the presence of a diol in medical diagnostic techniques, fermentation processes, tissue culture, diabetic testing strips and the like.

In one embodiment, the invention provides methods for detecting the presence of a sugar or diol in a sample which comprises measuring a change in the intensity ratio of a fluorescent compound when the compound reacts with the sugar or diol. It is known in the art that the measure of absolute flourescent intensity can be a difficult and time and labor consuming endeavor. Background noise from the sample can be present and the equipment requires frequent calibration and maintenance. By determining an intensity ratio of a compound at two different wavelengths, the process of measuring fluorescence can become more simplified. The intensity ratio is a measurement of the fluorescent intensity of a compound at two different excitation or emission wavelengths characteristic for the compound. An example of a measurement of the intensity ratio is shown for exainple in FIGS. 5 and 6B.

Detection of the probes of the present invention can employ numerous techniques, as will be readily recognized by those of ordinary skill in the art. For example, a simple system consists of a sample carrier, a source of radiation, and a detector capable of measuring the intensity of radiation passing through the sample. The absorbance characteristics of the probe as a function of analyte concentration at a given pH are easily established, permitting evaluation of a sample of unknown concentration. Numerous substrates, including a treated glass surface can be used as a carrier for the probes of the present invention.

The probes dyes can also be used in conjunction with standard flow injection analysis methods, in which reagents are introduced into a flowing stream of sample liquid. Another technique involves attachment of dye molecules to lengths of fiber-optic material, which are exposed to radiation and analyzed after contact with the sample. The probes can also be bound to polymeric material such as test paper for visual inspection. The probes of the present invention may also be used in vivo as apparent to one of ordinary skill in the art. (See e.g., U.S. Pat. Nos. 6,002,954, 6,011,984 and 6,319,540, the content of which are incorporated by reference and in which probes are immobilized in a biocompatible matrix.).

The present invention is described by reference to the following Examples, which are offered by way of illustration and are not intended to limit the invention in any maimer. Standard techniques well known by persons of ordinary skill in the art and/or the techniques specifically described below were utilized.

EXAMPLE 1

Stilbene derivatives combining the boronic acid group in position 4 and donor or acceptor groups in position 4' were synthesized. The molecular structures of the stilbene and substituted stilbenes investigated were as follows:

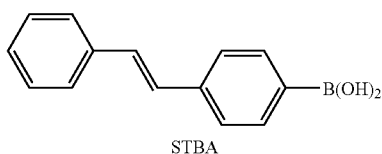

STBA

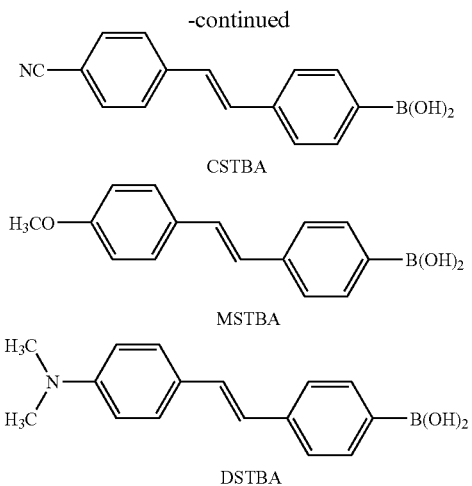

Dimethylamino and cyano groups are well known and used as donor and acceptor groups, respectively. Both groups have been widely used in the investigation of excited charge transfer in stilbene derivatives (44-46). The insertion of the methoxy group, which is a weaker donor group was also investigated. Stilbeneboronic acid (STBA) was used for a control molecule. A nitro group derivative has also been synthesized, but no fluorescence was observed in methanol and water for this compound. The results show that the insertion of a donor group and the boronic acid group directly on the stilbene in position 4 and 4', respectively, lead to an excited charge transfer state. At higher pH, a new blue shifted emission band appears due to the loss of the acceptor properties of the anionic form of the boronic acid group. On the other hand, the incorporation of the cyano group does not lead to any excited charge transfer state, but for the anionic form, an excited charge transfer can be observed. This is observed by the appearance of a new red shifted band in the emission spectrum.

The spectral properties of four stilbene derivatives containing the boronic acid group [—$B(OH)_2$]: stilbene-4-boronic acid (STBA), 4'-cyanostilbene-4-boronic acid (CSTBA), 4'-methoxystilbene-4-boronic acid (MSTBA) and 4'-(dimethylamino)stilbene-4-boronic acid (DSTBA) were evaluated. The emission spectrum of DSTBA displays a large solvent-polarity dependence showing the formation of a photoinduced charge transfer state (CT). This state is weakly present in MSTBA and not present for CSTBA and STBA for the neutral form of the boronic acid group. These results show the donor withdrawing property of the neutral form of the boronic acid group. At higher pH, the boronic acid group is present in the anionic form [—$B(OH)_3^-$], resulting in a change of the configuration around the boron atom from the triangular planar (sp2 hybridization) to the tetrahedral conformation (SP3 hybridization). This change induced a blue shift of about 50 nm and an increase of intensity in the emission spectrum of DSTBA due to the loss of the electron withdrawing properties for the anionic form of the boronic acid group, leading to the loss of the CT effect. The same effect is also observed for MSTBA. In contrast, a red shift of about 35 nm and a decrease of intensity are observed for CSTBA. from the neutral to the anionic forms of the boronic acid group. These observations lead to the conclusion that the anionic form of the boronic acid group acts as an electron donor group and a photoinduced CT state can be formed when an electron withdrawing group is present on the fluorophore.

The usefulness of this effect for the development of saccharide probes is also demonstrated. After addition of sugar, the emission spectra of DSTBA and MSTBA showed a blue shift and an increase of the intensity. On the other hand, a red shift and a decrease of the intensity are observed in the emission spectra of CSTBA after addition of sugar. A change from the neutral to the anionic form of the boronic acid group is used to explain these changes. These results show that the use of the combination of electron donor or withdrawing groups with the boronic acid group is a new and promising way to develop ratiometric fluorescent probes for glucose and other saccharides.

FIG. 1 shows the absorption and fluorescence spectra of the four stilbene derivatives investigated and the unsubstituted trans-stilbene. Spectral parameters are shown in Table 1. Insertion of the boronic acid in the 4 position induces a small red shift in the absorption spectrum in comparison with ST (FIG. 1A) This shift is due to the hyperconjugation of the aromatic system with the empty p orbital of the boron atom. The addition of cyano, methoxy and dimethylamino groups in the 4' position also induced a red shift in the absorption spectra (FIG. 1A) The maximum of the absorption spectrum of DSTBA (346 nm, Table 1) is relatively similar to that of the 4-(dimethylamino)stilbene (DS)(351 nm in acetonitrile). This shows that no particular effects are involved in the ground state following the insertion of a donor or acceptor group in position 4' of the stilbeneboronic acid.

Figure 1B:
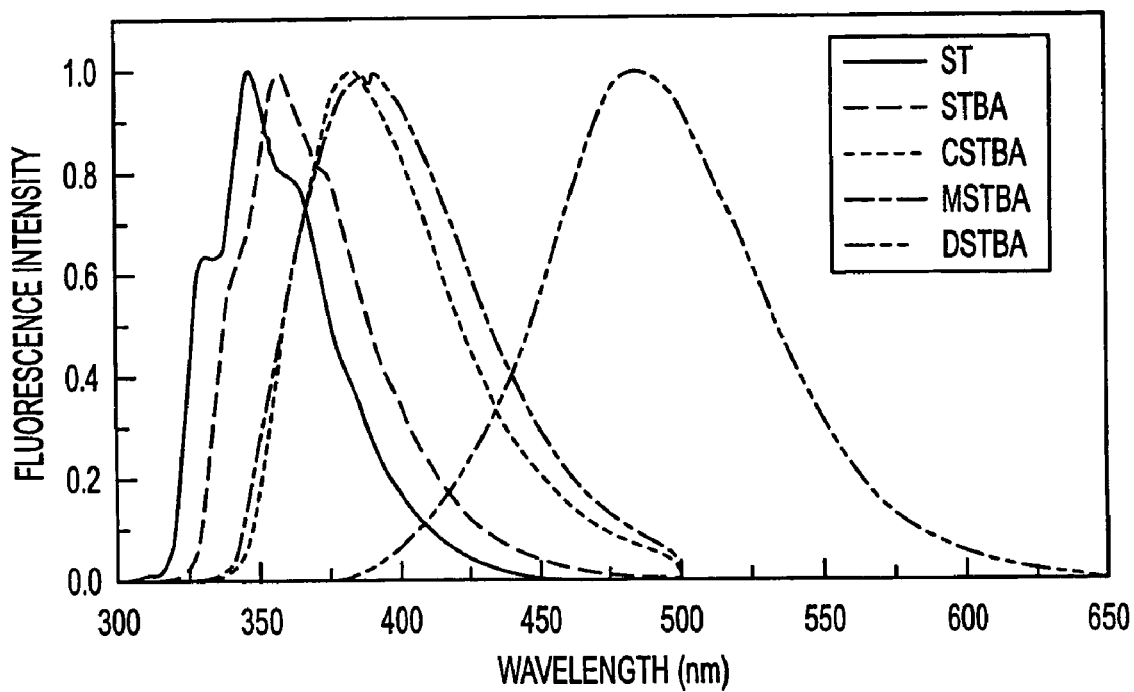
FIG. 1(B) is a graphical representation of the absorption and emission spectra of the stilbenes investigated in water/methanol 1:1 (v/v) at room temperature. ST is for trans-stilbene.
Figure 2:
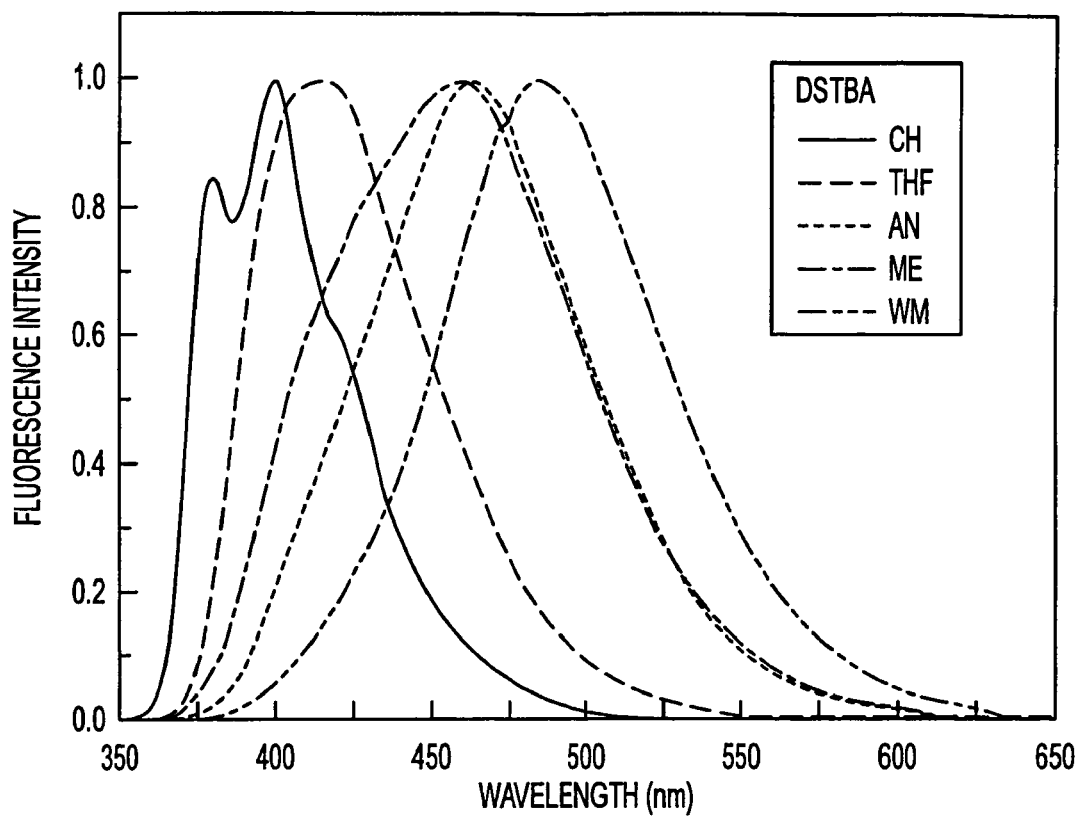
FIG. 2 shows the normalized emission spectra of DSTBA in different solvents. CH (cyclohexane), THF(tetralydrofuran), AN (acetonitrile), ME (methanol), and WM (water/methanol 1:1 (v/v)) at room temperature at $\lambda_{ex}$=350 nm.

Fluorescence spectra follow the same trend as the absorption spectra. STBA, CSTBA and MSTBA are red shifted in comparison with ST (FIG. 1B). These shifts are similar to those observed in the absorption spectra. The Stokes' shifts for these three compounds are similar to the one observed for ST, showing that no major effects are involved in the excited state for these compounds. On the other hand, the emission spectrum of DSTBA shows a large bathochromic shift in comparison with STBA. Since this shift, 127 nm, is much more larger than the shift observed in the absorption spectrum, 32 nm, the extent of the hyperconjugation due to the insertion of the amino group is not enough to explain this shift and this shows that an additional excited state relaxation process is involved. The emission spectrum of DSTBA shows also an important bathochromic shift in comparison with DS (440 nm in acetonitrile). These results suggest the formation of an excited induced CT state for DSTBA. In order to verify this hypothesis, we recorded the emission spectrum of DSTBA in various solvents of different polarity (FIG. 2). The emission spectrum of DSTBA in cyclohexane shows vibronic structure and is centered at 400 nm. While the polarity of the solvent is increased, the emission spectrum shows a large bathochromic shift (85 nm from CH to WM) and the vibronic structure is lost. On the other hand, the absorption spectra of DSTBA in the same series of solvent do not show any significant shift (not shown). Also, the Stokes' shift increases from 3820 $cm^{-1}$ in cyclohexane (CH) to 8300 $cm^{-1}$ in the water/methanol (50:50 v/v) mixture (WM). These observations are consistent with the formation of an excited induced CT state due to the presence of the donor amino group and the acceptor boronic acid group on the fluorophore. These results on DSTBA are comparable with the results reported for 4-dimethylamino-4-cyanostilbene (DCS) where a bathochromic shift of 115 nm is observed from methylcyclohexane to acetonitrile. ST and STBA do not show any solvent effect, but CSTBA and MSTBA show a little bathochromic shift with the increase of the polarity of the solvent (results not shown). These shifts are much more smaller, 12 nm for CSTBA and 21 nm for MSTBA from CH to WM, than that observed for DSTBA, 85 nm from CH to WM.

Table 1 also reports the fluorescence quantum yields of the derivatives investigated. For all stilbenes reported in this study, the fluorescence quantum yields decreased with the increase of the polarity of the solvent. This decrease is about 2 to 5 time smaller, from CH to WM, for ST, STBA and CSTBA while this decrease is more important for MSTBA and DSTBA, 10 to 15 time smaller from CH to WM. Despite this more important solvent effect, $\phi F$ remains larger for MSTBA and DSTBA than for the other three compounds in all the solvents.

Figure 3:
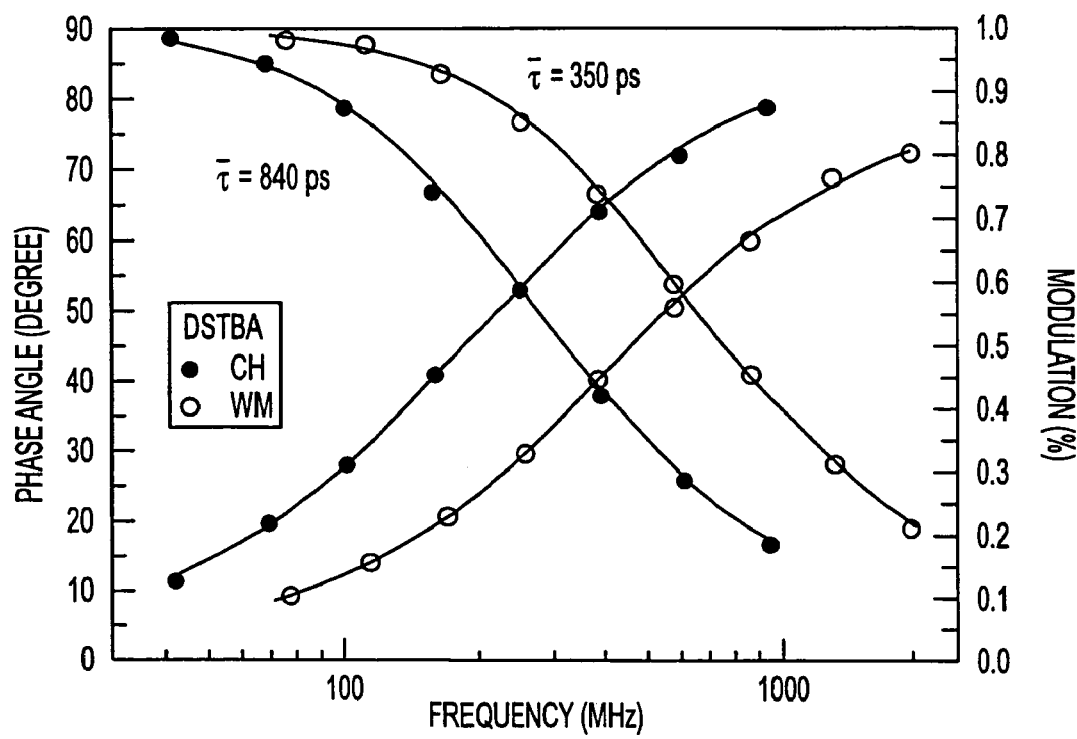
FIG. 3 shows the frequency decay profiles of DSTBA in cyclohexane (CH) and water/methanol 1:1 (v/v) (WM) at room temperature.

Fluorescence decay parameters of the stilbenes investigated are listed in Table 2. Mean fluorescence lifetimes of STBA and CSTBA are similar and comparable to the mean lifetime of ST, 26 ps in WM. For these three compounds, fluorescence decay profiles were satisfactorily fitted with a single exponential and lifetimes do not show any effect of solvent. MSTBA and DSTBA show much longer lifetime. For these two compound, single exponential model was used to fit the fluorescence decay curves in CH and THF while a two exponential model was needed for the decay profiles in acetonitrile (AN), methanol (ME) and WM. The observed mean lifetime decreased with the polarity of the solvent for MSTBA and DSTBA. Examples of the fluorescence decay profiles of DSTBA in CH and WM are displayed in FIG. 3. The decrease of the mean lifetime was larger for MSTBA, 670 to 80 ps from CH to WM, than for DSTBA, 840 to 350 ps from CH to WM. The similar solvent effects observed for DSTBA and MSTBA for the steady state and intensity decays could suggest that a CT state is also involved in the excited state of MSTBA.

pH and Sugar Effects on the Optical Spectra

STBA

Figure 4:
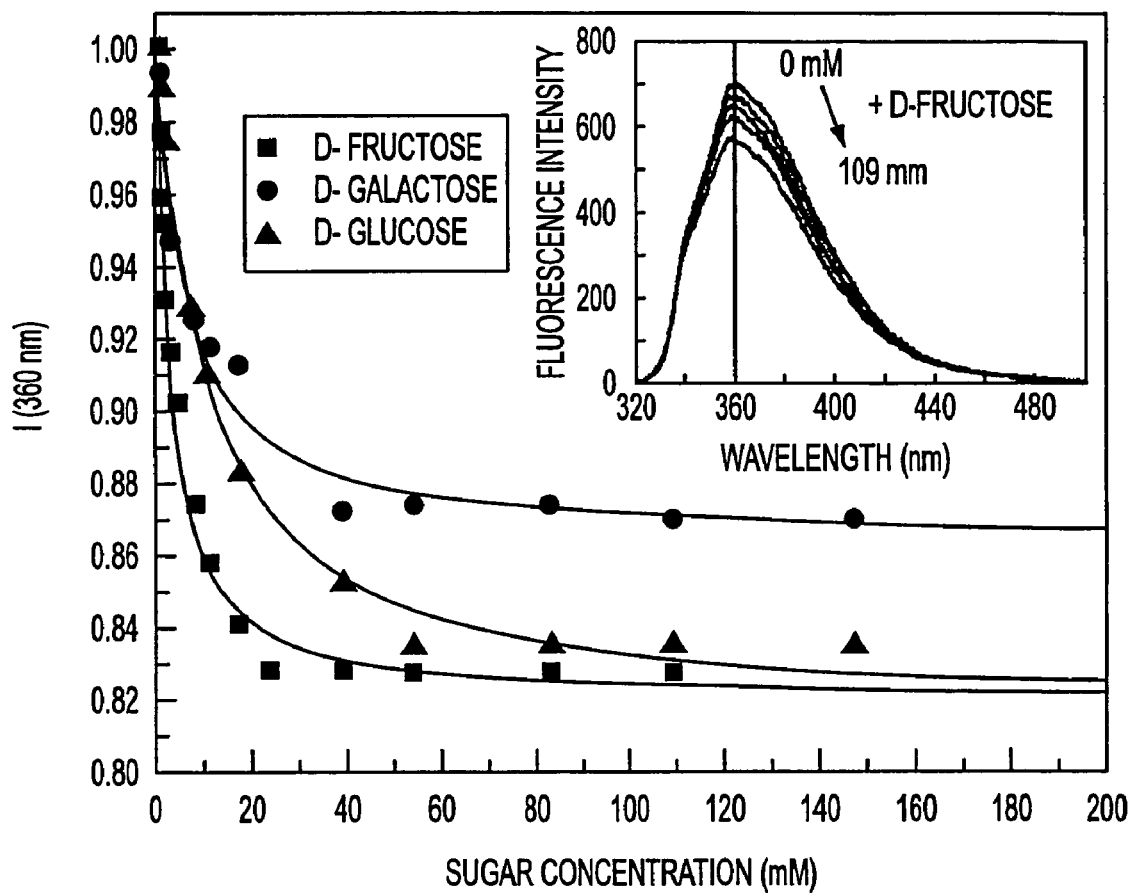
FIG. 4 is a graphical representation of titration curves of STBA in phosphate buffer pH 8.0/methanol 2:1 (v/v) at room temperature, $\lambda_{ex}$=310 nm.

FIG. 4 shows the intensity changes after addition of sugars for STBA. A decrease of the fluorescence emission is observed after the addition of sugar. The overall decrease is relatively weak, about 15%. Since the same intensity change is observed by increasing the pH, this change is attributed to the formation of the anionic form of the boronic acid group. The $pK_a$ of STBA is 8.86 (Table 3) and decreases to 6.4 for the complex STBA:fructose. A $pK_a$ of 8.86 is similar to the $pK_a$ of a multitude of phenylboronic acid derivatives reported in the literature (47-49). The decrease of this $pK_a$ for the complex with sugar is also a general observation for this chelator group. For example, Yoon et al. reported a $pK_a$ change of 8.8 to 5.9 for the anthrylboronic acid and its complex with fructose. At pH 8.0, STBA is present mostly in its neutral form. After the addition of sugar, the complex exists under the anionic form due to its lower $pK_a$. This change from the neutral to the anionic form is at the origin of the intensity changes observed for STBA and the other complexes presented in this study. Dissociation constants ($K_D$) for the three different sugars are presented in Table 3. All titration curves against sugars have been taken at pH 8.0. This pH does not correspond necessarily to the maximum effect of the optical change but is an average pH that allows measurements of all derivatives at the same pH. The pH effect on the $K_D$ values is discussed below. Monophenylboronic acid groups are well known to be more sensitive to D-fructose and the sensitivity decreases for D-galactose and decreases again for D-glucose. All stilbene derivatives presented in this study follow this rule and show $K_D$ similar to the other monophenylboronic group. For example, phenylboronic acid shows $K_D$ of 0.2, 3.6 and 9.1 mM for D-fructose, D-galactose and D-glucose, respectively.

Intensity changes observed for STBA are similar to the intensity changes reported for anthryl-2-boronic acid. For this anthracene derivative, the boronic acid group is also linked directly on the anthracene fluorophore. Intensity decreases of 30% and 10% were reported after the addition of fructose and glucose at pH 7.4, respectively. To explain these decreases, the authors suggested a photoinduced electron transfer (PET) mechanism where the negative charge on the boron atom acts as the quencher. This statement was based on the oxidizability of the borate. In the insert of FIG. 4, we show the emission spectra of STBA with different concentrations of fructose. We can observe that the emission is slightly blue shifted and an isosbestic point appears at about 338 nm after the addition of fructose. This could suggest that the effects of sugars on the emission spectra of STBA could be induced by the change of conformation of the boron atom from the neutral to the anionic forms, $sp^2$ to $sp^3$, as schematically shown in Scheme 1. Without being bound by theory, the loss of the empty p orbital of the boron atom could result in a partial loss of the resonance between the aromatic system and the boronic acid group. Further studies would be necessary to clarify the nature of these fluorescence changes.

DSTBA

Figure 5A:
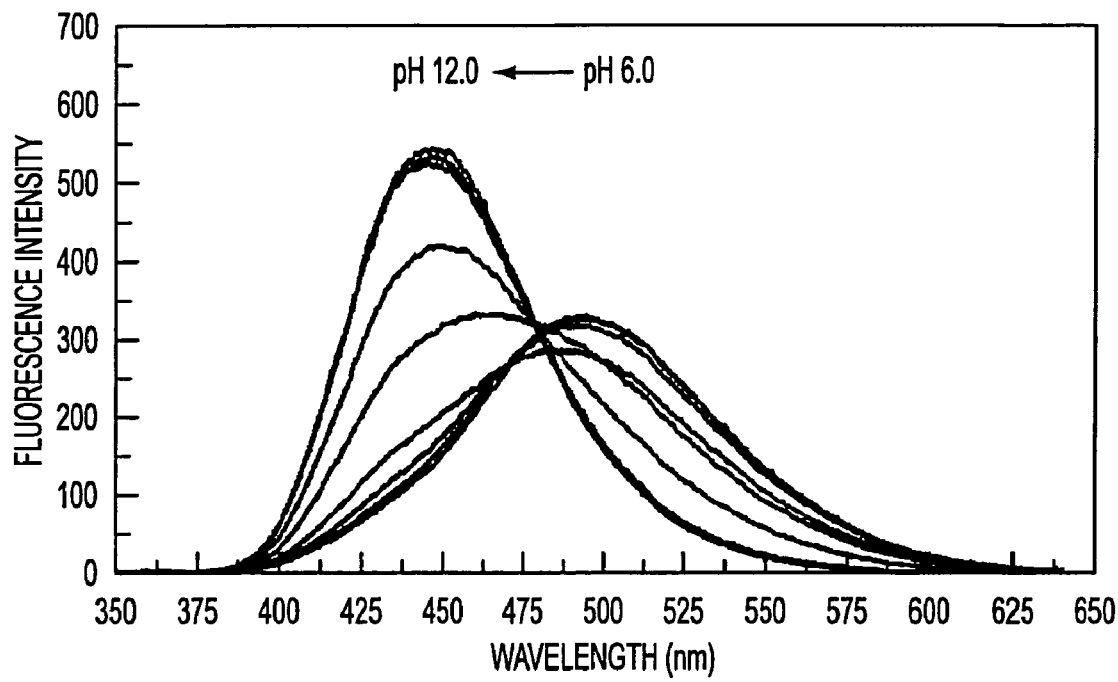
FIG. 5(A) pH dependence on the emission spectra of DSTBA without sugar at room temperature, $\lambda_{ex}$=330 nm. (B) Titration curves of DSTBA with and without sugar.
Figure 5B:
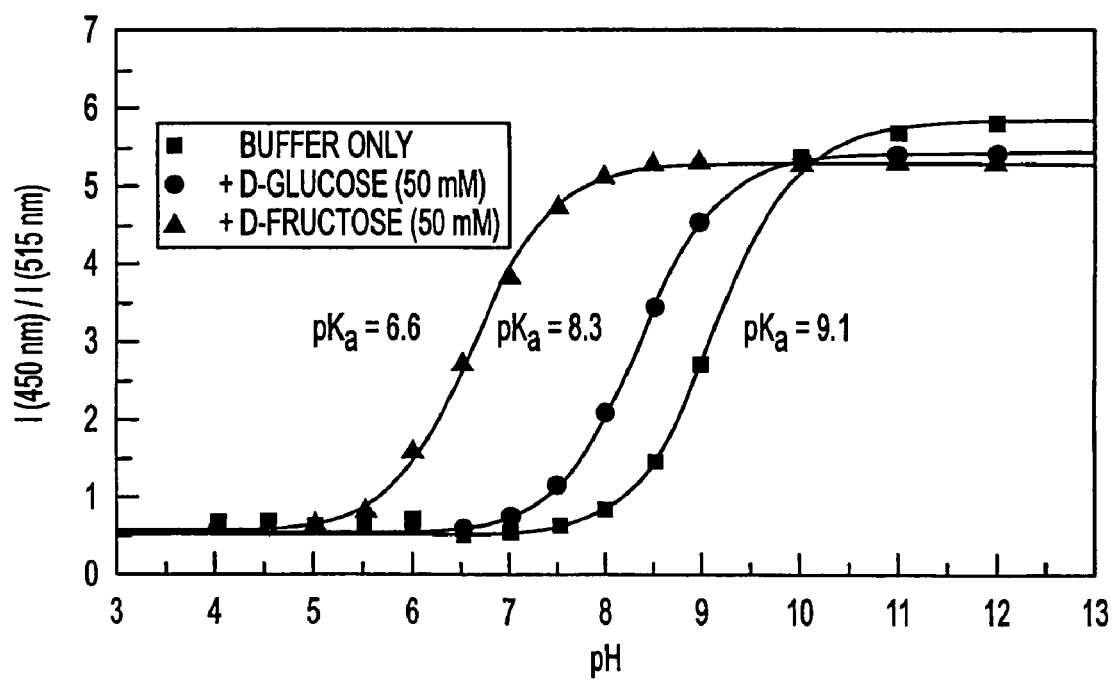

FIG. 5A displays the pH dependence of the fluorescence spectra of DSTBA. The emission spectrum shows a hypsochromic shift of about 45 nm and an increase of the intensity as the pH is increased from 6 to 12. These dramatic changes in the emission band of DSTBA are explained by the loss of the electron withdrawing property of the boronic acid group following the formation of the anionic form at high pH. This results in the loss of the CT excited state, resulting in a blue shift and the increase of the intensity. The absorption spectrum of DSTBA also shows a hypsochromic shift of about 15 nm (results not shown), showing that the formation of the anionic forms also perturbs the ground state of the compound. We also observed significant blue shifts in both absorption and emission spectra at pH below 4.0 (results not shown), which was explained by the protonation of the dimethylamino group. Titration curves against pH with and without sugar are presented in FIG. 5B. The $pK_a$ of DSTBA is slightly higher than that observed for STBA and the presence of sugar induces a decrease of the $pK_a$.

Figure 6A:
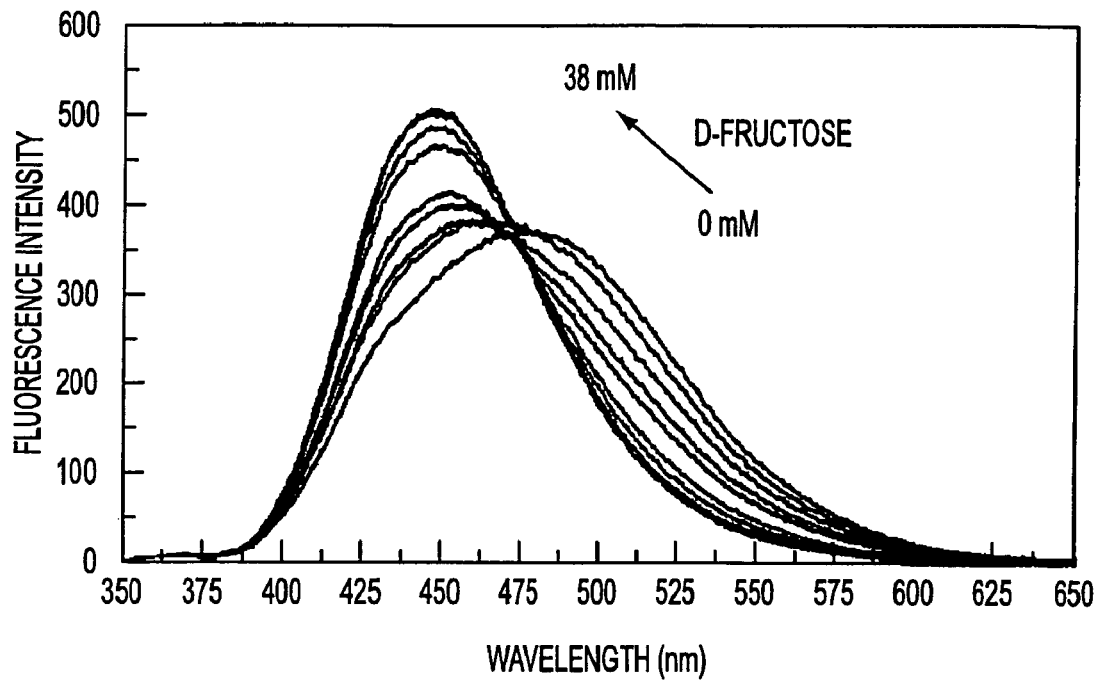
FIG. 6(A) is a graphical representation of the change in the emission spectra of DSTBA after addition of D-fructose, in phosphate buffer pH 8.0/methanol 2:1 (v/v) at room temperature, $\lambda_{ex}$=330 nm.
Figure 6B:
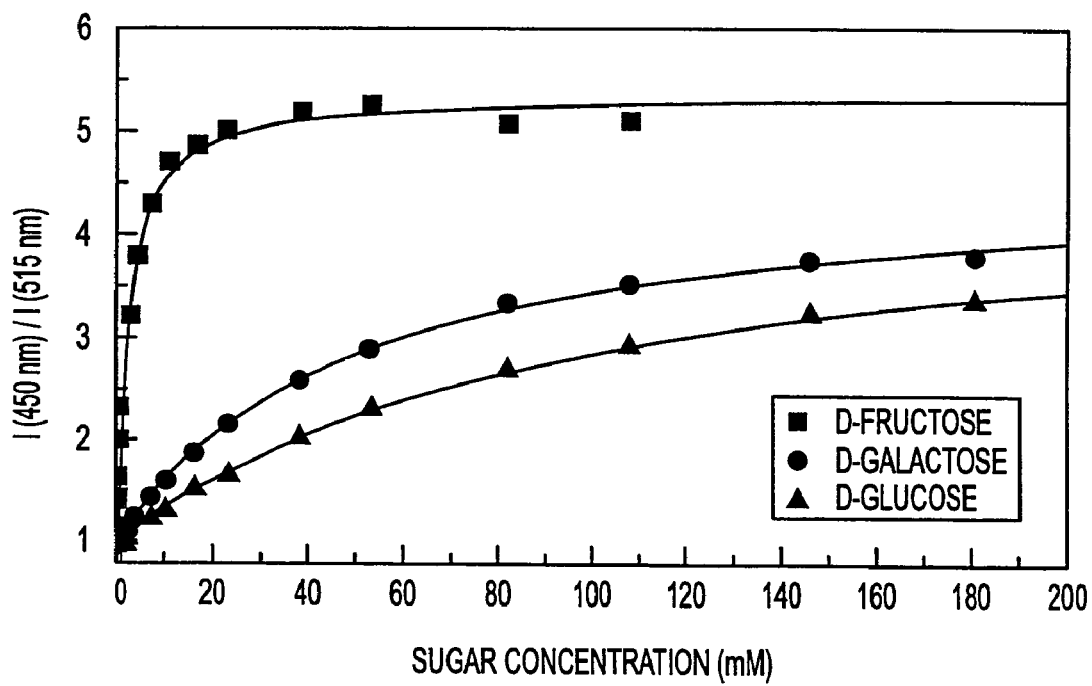
FIG. 6(B) is a graphical representation of titration curves of DSTBA with the different sugars.

FIG. 6A displays the effect of fructose on the emission spectrum of DSTBA. As observed for the pH, the addition of fructose induces a hypsochromic shift and an increase of the intensity of emission. The same spectral changes are observed for the other sugars. As explained above, the results are interpreted with the formation of the anionic form of the sugar complex due to the decrease of the $pK_a$ of this complex. In comparison with STBA, the formation of the anionic form in DSTBA induces not only a change in the emission intensity but also a blue shift in the emission band. This important effect, resulting from the insertion of a electron donating group on the fluorophore, provides a wavelength-ratiometric probe for the analysis of sugars using changes in the donor-acceptor properties of this kind of compounds. The ratiometric method is well known to be a superior technique for quantitative measurements of analytes in comparison with simple intensity changes [35-37]. Titration curves against sugars for DSTBA are shown in FIG. 6A and $K_D$ values are listed in Table 3. This compound shows similar affinity for fructose than the others phenylboronic acid groups but much less sensitivity for galactose and glucose.

MSTBA

The pH dependence of the fluorescence of MSTBA (results not shown) is quite similar to what we observed for DSTBA. By increasing the pH, we can observe a modest hypsochromic shift and an increase of the intensity of the emission. The blue shift is smaller, 29 nm, in comparison with DSTBA. This lead to the conclusion that a CT state is also involved in the excited state of MSTBA. Due to a smaller effect of solvent and pH on the emission spectrum of MSTBA in comparison with DSTBA, we can say that the extent of charge transfer is less than for DSTBA. $pK_a$ values with and without sugars are listed in Table 3 and comparable with those observed for the other stilbene derivatives.

Figure 7:
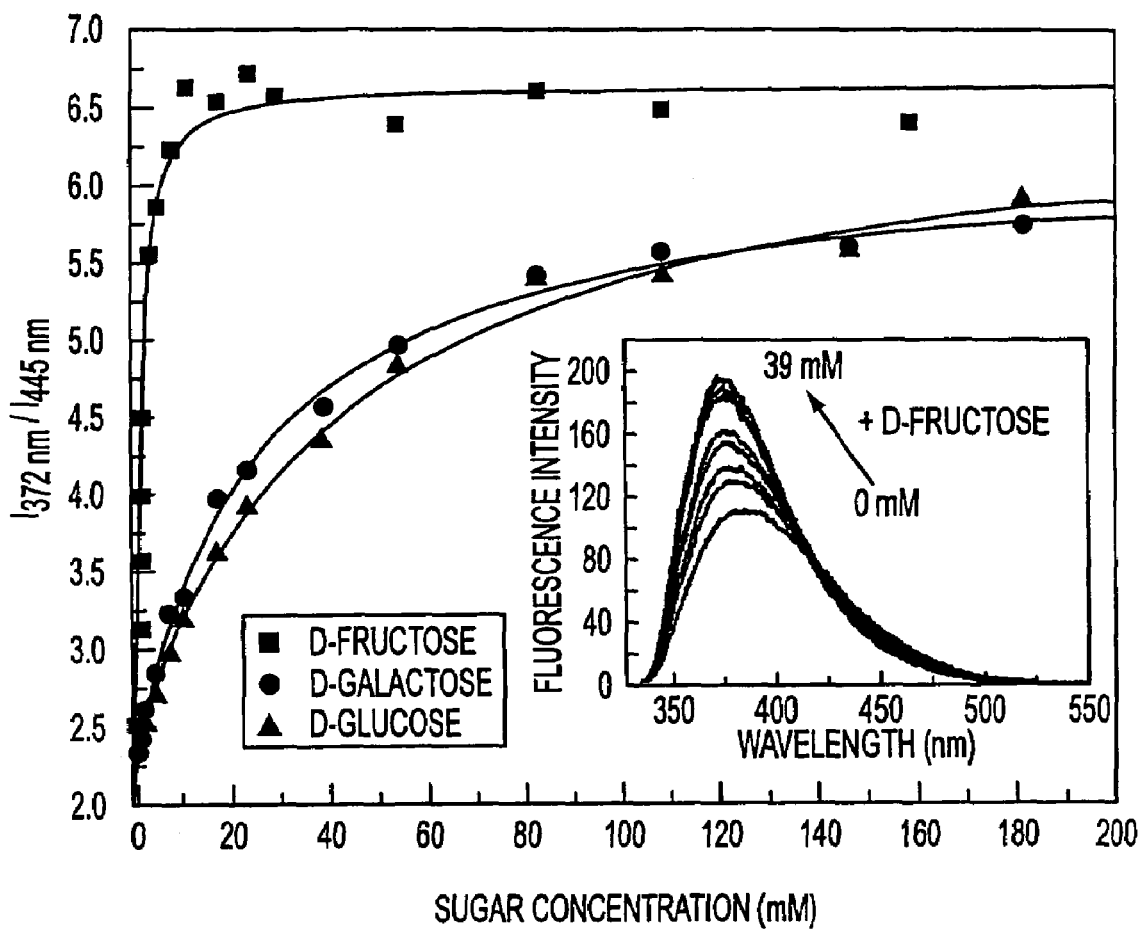
FIG. 7 is a graphical representation of titration curves of MSTBA against sugars in phosphate buffer pH 8.0/methanol 2:1 (v/v) at room temperature, $\lambda_{ex}$=325 nm. Insert: emission spectra changes with the addition of D-fructose.

Effect of fructose on the emission spectrum of MSTBA is shown in the inset of FIG. 7. As described for the pH, the effect of sugar is smaller for the shift of the band but the intensity change is comparable to what we observed for DSTBA. Titration curves and $K_D$ are shown in FIG. 7 and Table 3, respectively.

CSTBA

Figure 8A:
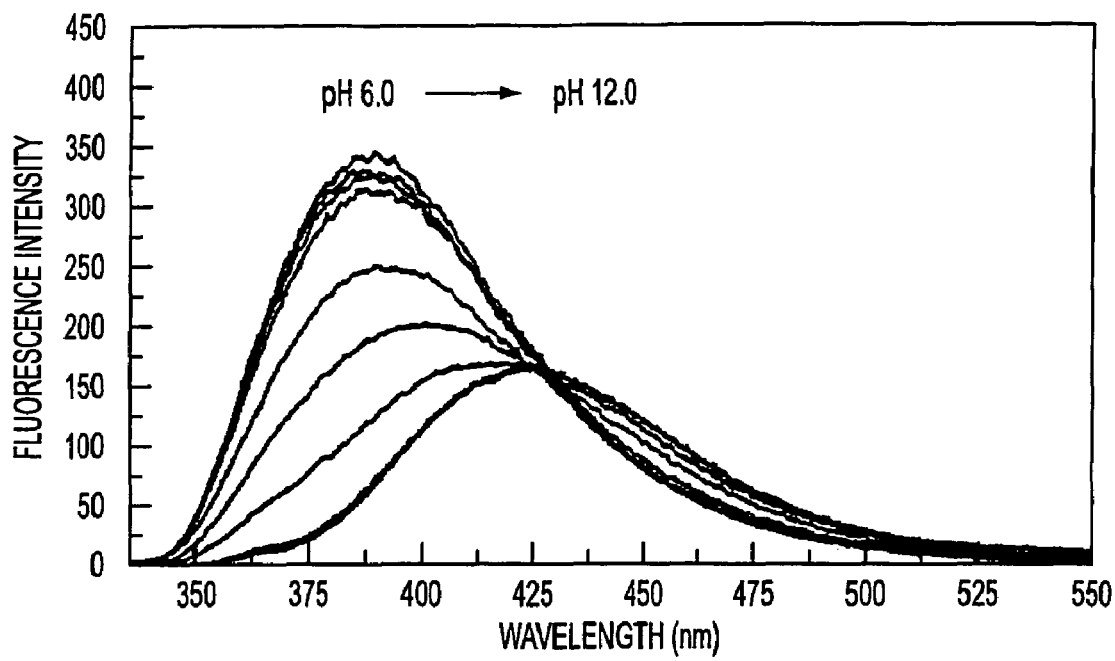
FIG. 8(A) is a graphical representation of pH dependence on the emission spectra of CSTBA without sugar at room temperature, $\lambda_{ex}$=325 nm.
Figure 8B:
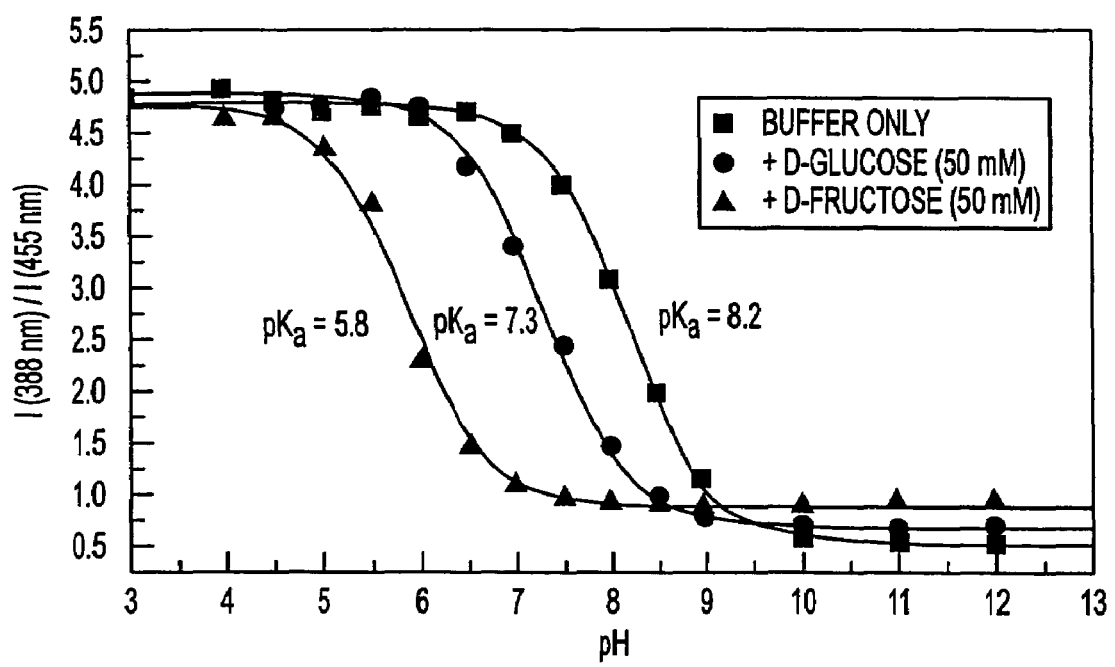
FIG. 8(B) shows titration curves of CSTBA with and without sugar.
Figure 9A:
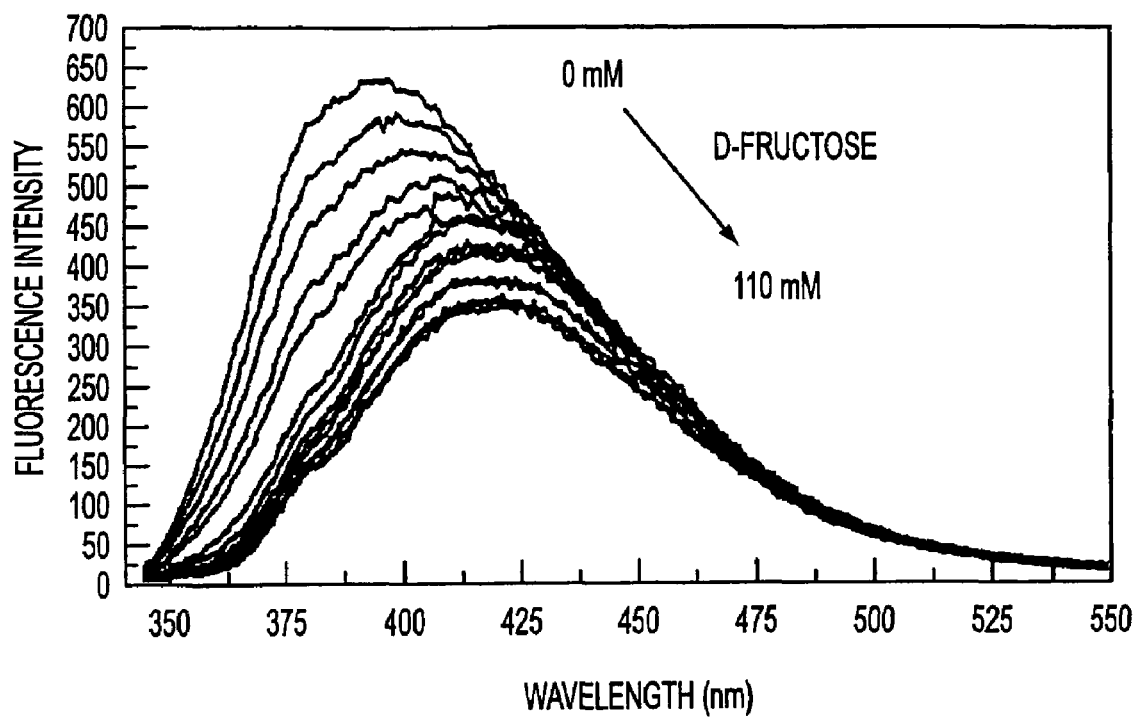
FIG. 9(A) shows a change in the emission spectra of CSTBA after addition of D-fructose, in phosphate buffer pH 8.0/methanol 2:1 (v/v) at room temperature, $\lambda_{ex}$=335 nm.
Figure 9B:
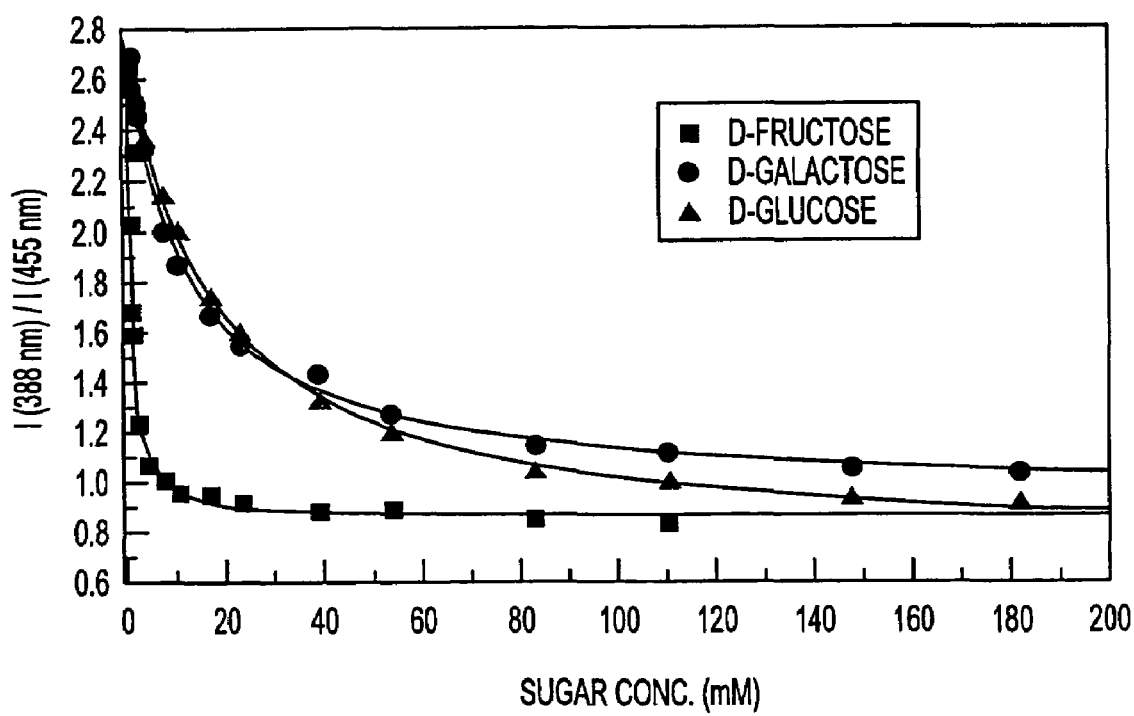
FIG. 9(B) shows titration curves of CSTBA with the different sugars.

CSTBA is a different compound than the previous two compounds because it possesses two electron withdrawing groups, the cyano and boronic acid groups. As expected for this kind of compounds, no CT states are observed for the neutral form of the boronic acid group. On the other hand, we can observe a large bathochromic shift, 40 nm, and a decrease of the intensity in the emission spectrum of CSTBA with an increase of pH (FIG. 8A). A smaller red shift, 8 nm, is also observed in the absorption spectrum following the increase of pH (results not shown). The shift and the intensity change are very similar, but in opposite direction respect to those observed for DSTBA and MSTBA. We attributed this new red shifted band to an excited CT state present for the anionic form of CSTBA. This suggests that the anionic form of the boronic acid group can act as an electron donor group. Titration curves against pH and $pK_a$ values of CSTBA are shown in FIG. 9A and Table 3. $pK_a$ values are comparable to those observed for the other stilbene derivatives previously presented. FIG. 9A shows the effect of addition of fructose on the emission spectrum of CSTBA. The same effects as those observed for the pH are observed upon the addition of sugars. Titration curves against sugars and $K_D$ values are presented in FIG. 9B and Table 3, respectively. By comparing the $pK_a$ and $K_D$ of all stilbene derivatives (Table 3), we can observe a decrease of these values from DSTBA to MSTBA and CSTBA. Only STBA does not follow the trend. As the strength of the donor group increased, one could expect a larger negative partial charge on the boron atom in the ground state. A partial negative charge on the boron would reduce the affinity of the boronic acid group to link with a hydroxyl group. Without wishing to be bound by theory, this effect could explain the trend observed for the $pK_a$ and the $K_D$ values since the methoxy group is a weaker donor and the cyano group is not a donor at all. However, further studies would be necessary to verify this hypothesis.

The effect of pH on the dissociation constant of CSTBA for D-fructose was also evaluated (results not shown). A decrease of the dissociation constant with the increase of pH (3.22, 1.19 and 0.65 mM for pH of 7.0, 7.5 and 8.0 respectively) was observed, suggesting that the affinity of the boronic acid group for fructose increases when the pH increases. This could be useful to setting the concentration range of the applicability of a boronic acid sensor. The effect of adding fructose on the fluorescence lifetime of the derivatives was also performed. For all derivatives, except for MSTBA, a decrease of the mean lifetime was observed (results not shown). For example, the lifetime of DSTBA decreased to 320 ps in presence of 110 mM of fructose.

The combination of an electron withdrawing and/or donor group and the boronic acid group both directly linked to a fluorophore could lead to the formation of an excited charge transfer state. The neutral form of the boronic acid group act as an electron withdrawing group while the anionic form could acts as an electron donor group. After complexation with a sugar molecule, the boronic acid changes from the neutral form to the anionic one, and a change in the CT properties of the fluorophore occurs. A shifting and a change in the intensity of the emission bands are then observed. This leads to a new optical and ratiometric approach for the analysis of sugar using fluorescence probes having the boronic acid group. This donor/acceptor combination gives much more optical changes than the presence of only the boronic acid group on a fluorophore opening the perspective to a new class of fluorescence probes for sugars.

TABLE 1

Spectral properties and fluorescence quantum yield ($\Phi_F$) of the stilbene derivatives in water/methanol 1:1 (v/v) at room temperature.

|  | $\lambda_{abs}$ (nm) | $\epsilon$ ($M^{-1} cm^{-1}$) | $\lambda_F$ (nm) | $\Delta^b$ ($cm^{-1}$) | $\Phi_F$ |
|---|---|---|---|---|---|
| $ST^a$ | 296 | 33800 | 348 | 5100 | 0.021 |
|  | $(295)^c$ | (31500) | (349) | (5250) | (0.044) |
| STBA | 314 | 39700 | 358 | 3950 | 0.009 |
|  | (317) | (31300) | (359) | (3690) | (0.054) |
| CSTBA | 327 | 47300 | 385 | 4600 | 0.006 |
|  | (330) | (34900) | (373) | (3500) | (0.013) |
| MSTBA | 324 | 38000 | 391 | 5320 | 0.025 |
|  | (325) | (25700) | (370) | (3750) | (0.31) |
| DSTBA | 346 | 32800 | 485 | 8300 | 0.088 |
|  | (347) | (36500) | (400) | (3820) | (0.64) |

$^a$ST: trans-stilbene;
$^b\Delta$: Stokes' shift;
$^c$in cyclohexane.

TABLE 2

Fluorescence decay parameters of the stilbenes investigated in water/methanol 1:1 (v/v) at room temperature.

|  | $\tau_1$ (ps) | $\tau_2$ (ps) | $\alpha_1$ | $\alpha_2$ | $\tau$ (ps) | $\chi_R^2$ |
|---|---|---|---|---|---|---|
| STBA | 23 | — | 1.0 | — | 23 | 1.8 |
| CSTBA | 21 | — | 1.0 | — | 21 | 5.4 |
| MSTBA | 30 | 130 | 0.82 | 0.18 | 80 | 2.2 |
| DSTBA | 40 | 360 | 0.20 | 0.80 | 350 | 0.9 |

EXAMPLE 2

The probes of this Example are based on donor/acceptor diphenylbutadiene and diphenylhexatriene derivatives involving the boronic acid group that display useful shifts and intensity changes in their emission spectra. These changes are induced by the changes of the electron-withdrawing property between the boronic acid group and its anionic form. Compared to the analogous stilbene probes, which also displays the charge transfer mechanism, the charge transfer mechanism can be applied for longer wavelength probes. This mechanism could be extended to the development of red and/or near infrared probes using appropriate fluorophores. In addition, the charge transfer mechanism induces a change in the fluorophore lifetime of the probes, thus opening the door to the development of new probes for fluorescence lifetime based sensing for sugars.

This example demonstrates the effect of the wavelength of absorption and emission of the fluorophore on the efficiency on the CT mechanism and on the spectral changes of fluorophores combining the boronic acid group and an electron-donor group. The following compounds designated as compounds 4 and 5 were examined:

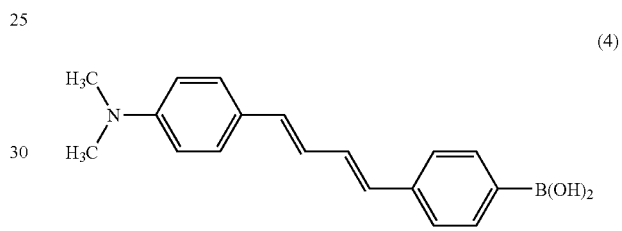

(4)

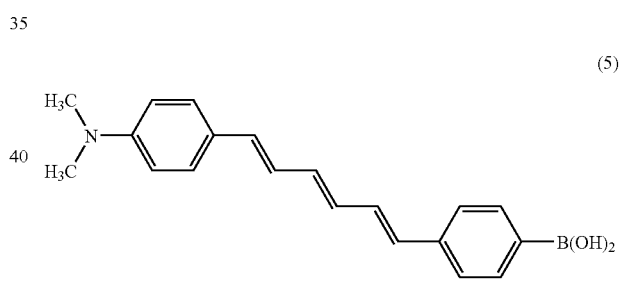

(5)

TABLE 3

$pK_a$ and dissociation constant ($K_D$) of the different stilbenes investigated in the absence and presence of sugars. All solution contained 33.3% methanol. $K_D$ measured at pH 8.0.

|  | pKa | | | $K_D$ (mM) | | |
|---|---|---|---|---|---|---|
|  | Alone | +D-fructose (50 mM) | +D-glucose (50 mM) | D-fructose | D-galactose | D-glucose |
| STBA | 8.86 | 6.4 | 7.63 | 3.4 | 6 | 11 |
|  | (±0.08) | (±0.1) | (±0.06) | (±0.7) | (±1) | (±1) |
| CSTBA | 8.17 | 5.84 | 7.30 | 0.65 | 12.5 | 18.3 |
|  | (±0.03) | (±0.04) | (±0.04) | (±0.04) | (±0.8) | (±0.8) |
| MSTBA | 8.58 | 6.36 | 7.88 | 1.0 | 26 | 43 |
|  | (±0.03) | (±0.03) | (±0.01) | (±0.1) | (±2) | (±4) |
| DSTBA | 9.14 | 6.61 | 8.34 | 2.5 | 49 | 98 |
|  | (±0.03) | (±0.02) | (±0.01) | (±0.2) | (±1) | (±3) |

Both compounds show longer wavelength of emission than the stilbenes of Example 1. Solvent polarity effect shows the presence of an excited-state charge transfer for both compounds. In both cases, the formation of the anionic form of the boronic acid group, at high pH or induced by the complexation with sugar, induces a blue shift and an increase of the intensity in the emission spectra. Frequency-domain intensity decays of the emission are also presented. The results show that the spectral changes are also associated with modest changes in the fluorescence lifetimes.

Figure 10A:
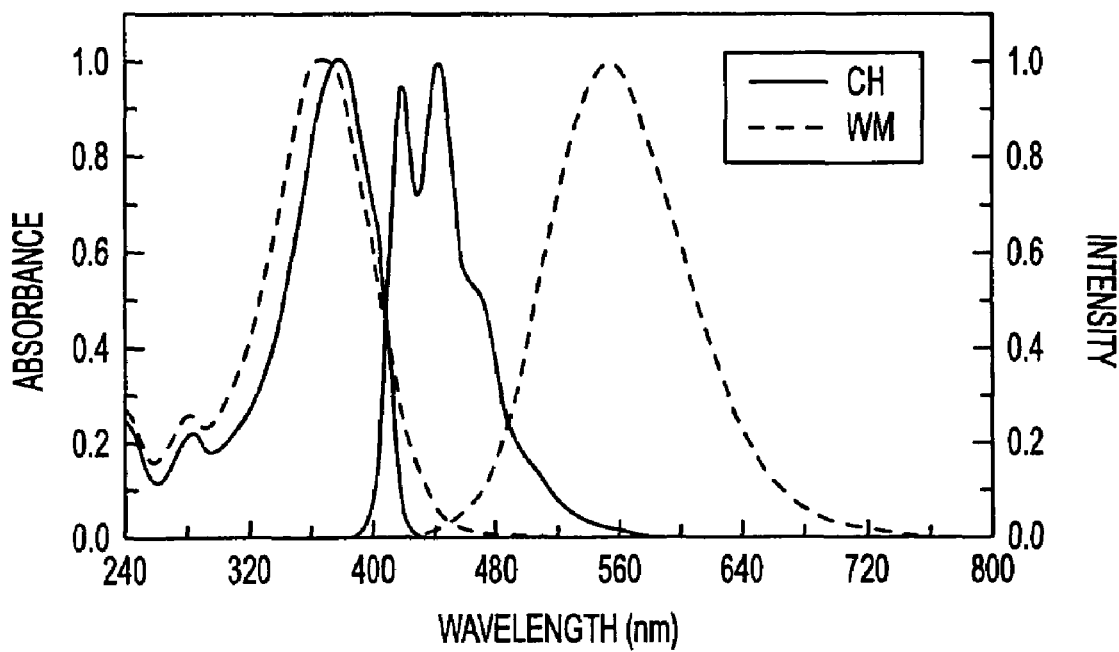
FIG. 10(A) is a graphical representation of the absorption and emission spectra of compound 4 in cyclohexane (CH) and water/methanol 1:2 (v/v) (WM) at room temperature.
Figure 10B:
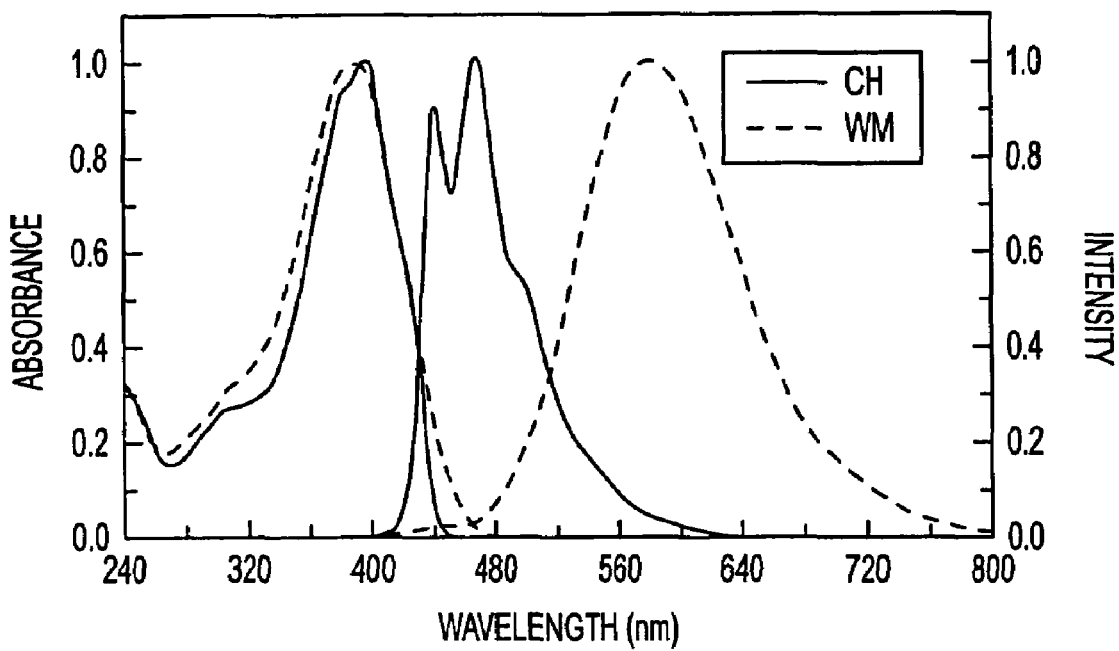
FIG. 10(B) is a graphical representation of the absorption and emission spectra of compound 5 in cyclohexane (CH) and water/methanol 1:2 (v/v) (WM) at room temperature.

Absorption and emission spectra for 4 and 5 in cyclohexane and in a mixture of water/methanol are displayed in FIG. 10. Spectral parameters are listed in Table 4. In cyclohexane, both compounds show vibronic structure and small Stokes' shift in their absorption and emission spectra. In water/methanol, absorption spectra remain similar but the emission spectra show large red shifts and lost of the vibronic resolution for both compounds. These spectral changes follow the increase of the polarity of the solvent and are characteristic of the formation of an excited-state charge transfer state in polar solvent. As discussed previously for the 4'-dimethylaminostilbene-4-boronic acid (DSTBA), the excited-state charge transfer occurs between the electron donor dimethylamino group and the electron withdrawing boronic acid group. The dimethylamino/boronic acid pair gives similar spectral characteristics and polarity effects as other donor/acceptor pairs. The absorption and emission maxima of 4 ($\lambda_{abs}$=368 nm, $\lambda_F$=551 nm and $\Delta$=9025 cm$^{-1}$) are similar to the corresponding parameters of the p-dimethylamino-p'-cyanodiphenylbuta-1,3-diene in methanol ($\lambda_{abs}$=399 nm, $\lambda_F$=576 nm and $\Delta$=7701 cm$^{-1}$) [Singh et al.]. Similarly, the absorption and emission maxima of 5 ($\lambda_{abs}$=390 nm, $\lambda_F$=580 nm and $\Delta$=8400 cm$^{-1}$) are comparable to the corresponding parameters of the p-dimethylamino-p'-nitrodiphenylhexa-1,3,5-triene in acetonitrile ($\lambda_{abs}$=452 nm, $\lambda_F$=625 nm and $\Delta$=6156 cm$^{-1}$) (52). For comparison, absorption and emission spectra of diphenylbuta-1,3-diene (DPB) and diphenylhexa-1,3,5-triene (DPH) are independent of the polarity of solvent and show maxima of: $\lambda_{abs}$=330 nm, $\lambda_F$=380 nm and $\Delta$=4000 cm$^{-1}$ for DPB (53) and $\lambda_{abs}$=352 nm, $\lambda_F$=452 nm and $\Delta$=6290 cm$^{-1}$ for DPH (56) both in acetonitrile.

Despite the longer wavelength of absorption and emission of 4 and 5 in comparison with DSTBA ($\lambda_{abs}$=346 nm and $\lambda_F$=485 nm), the Stokes' shifts remain similar for the three compounds: $\Delta$=8300 cm$^{-1}$ for DSTBA in comparison with 9025 cm$^{-1}$ and 8400 cm$^{-1}$ for 4 and 5, respectively. This observation seems to demonstrate that the CT remains efficient with the increase of the length of the molecule and the decrease of the energy of excitation and emission. This observation also shows that the CT mechanism is applicable to a wide range of fluorophores and remains efficiency for long-wavelength probes.

Figure 11A:
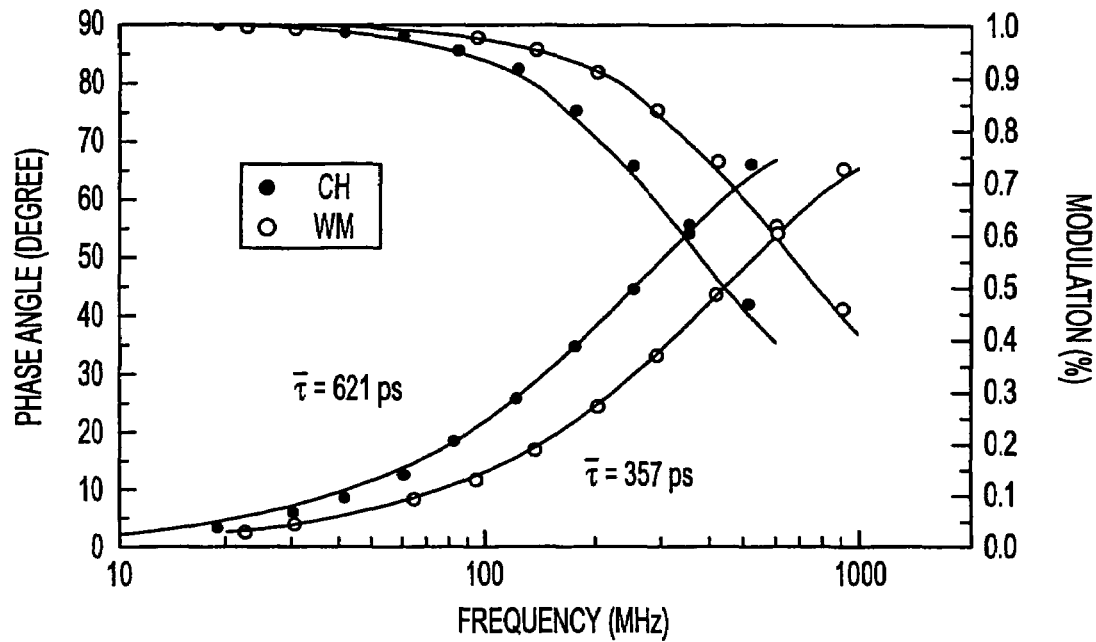
FIG. 11A shows the frequency decay profiles of compound 4 in cyclohexane (CH) and water/methanol 1:2 (v/v) (WM) at room temperature.
Figure 11B:
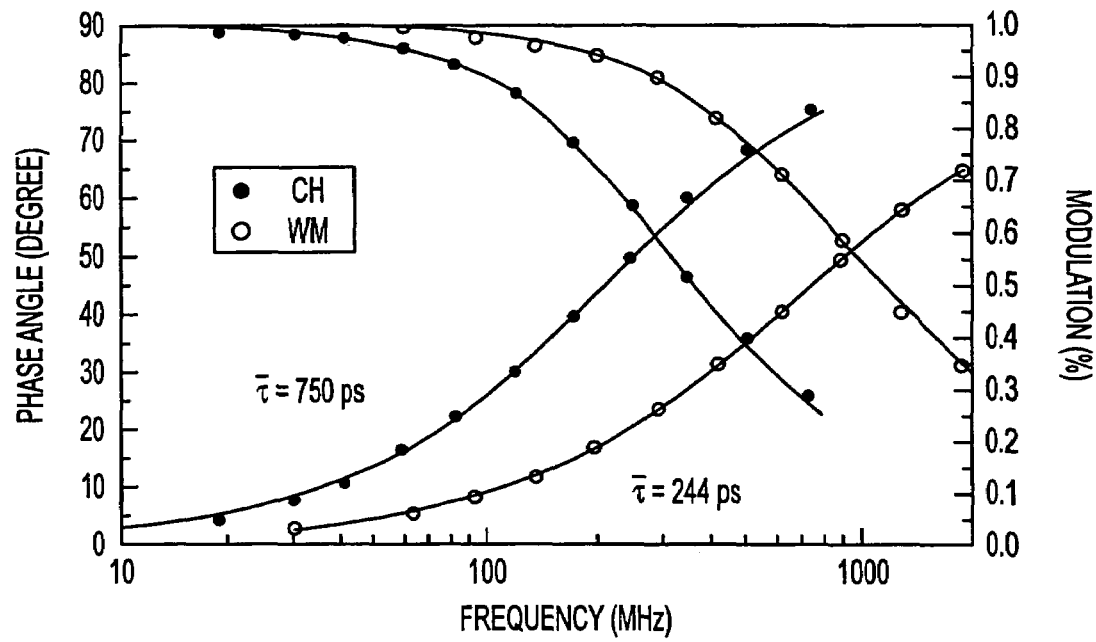
FIG. 11B shows the frequency decay profiles of compound 5 in cyclohexane (CH) and water/methanol 1:2 (v/v) (WM) at room temperature.

FIG. 11 shows the frequency-domain decay profile of 4 and 5 in cyclohexane and water/methanol. Intensity decay parameters are listed in Table 5. For both compounds, a decrease of the mean lifetime is observed when the polarity of the solvent increases as seen by the higher frequency response of the phase angle and modulation in FIG. 11. Intensity decays are mono exponential in cyclohexane for 4 and 5 but become double exponential in water/methanol for 5 while remain single exponential for 4. This decrease of the mean lifetimes following the formation of the excited-state charge transfer could be explained by a twisted induced charge transfer (TICT) state which increases the non-radiative decay rate as observe for some DPH derivatives (55). The fluorescence lifetime of this family of compounds is also known to show large dependence on the viscosity of the solvent. For example, DBP show a mean lifetime of 60 ps in ethanol and 351 ps in cyclohexanol (56).

pH Effects on the Spectroscopic and Photophysiscal Properties

Figure 12A:
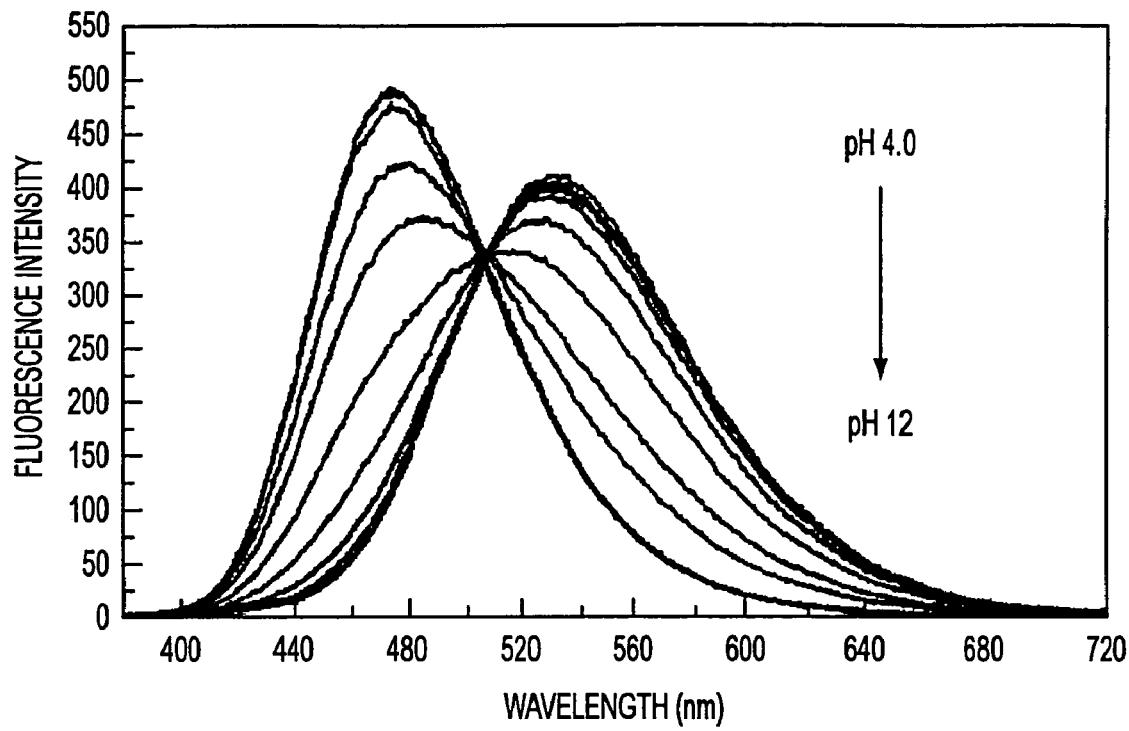
FIG. 12A shows pH dependence on the emission spectra of 4 without sugar at room temperature, $\lambda_{ex}=370$ nm.
Figure 13A:
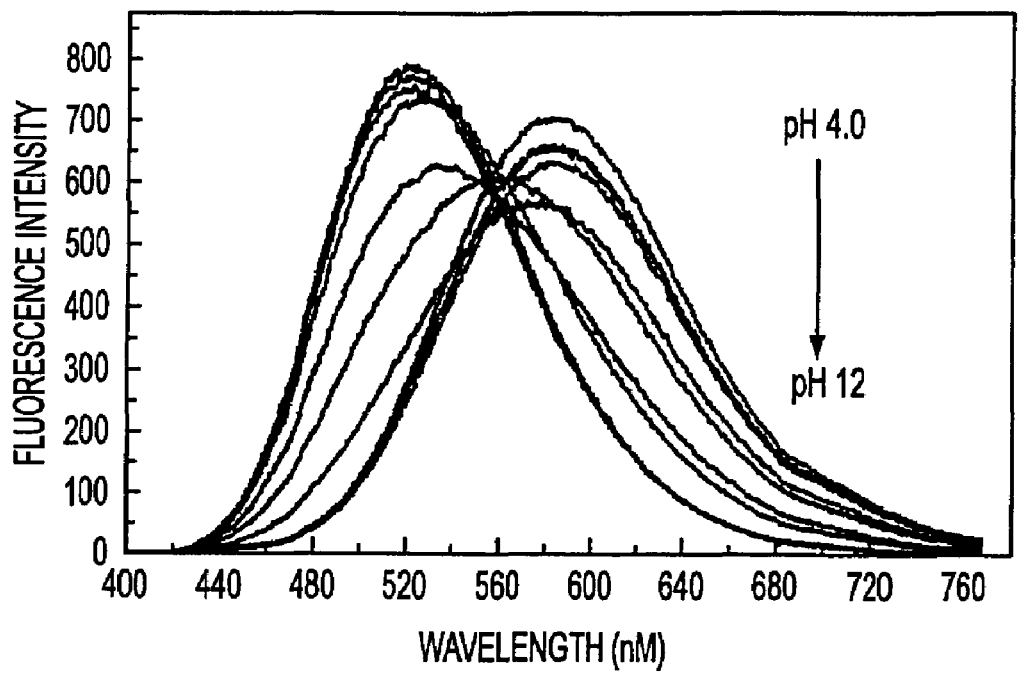
FIG. 13A shows the pH dependence on the emission spectra of compound 5 without sugar at room temperature, $\lambda_{ex}=390$ nm.

FIGS. 12A and 13A display the pH dependence of the emission spectra of 4 and 5, respectively. As the pH increases, we observed an increased of the intensity and a blue shift of the emission profile for both compounds. The isobestic point observed in both cases indicates equilibrium between two species as the pH increases. These species are the neutral and the anionic forms of the boronic acid group. As previously described for stilbene derivatives [DiCesare and Lakowicz], the spectral changes are attributed to the lost of the electron-withdrawing properties of the boronic acid group following the formation of the anionic form. This lost of the electron-withdrawing properties prevent the formation of the CT state and induce the blue shift and the increase of the intensity. The shift induce by the pH observed in the emission spectra of 4 (3360 cm$^{-1}$) is larger than the one observe for 5 (1975 cm$^{-1}$). For comparison, the shift observed for the stilbene analogue (DSTBA) was 9769 cm$^{-1}$. Also, we observe a smaller increase of the intensity as the molecular length increases. These observations seem to show that as the molecular length increases and/or the emission energy decreases, the lost of the electron-withdrawing property of the boronic acid group lead to smaller spectral changes. This could also lead to the conclusion that the charge transfer is less important as the molecular length increases.

Figure 12B:
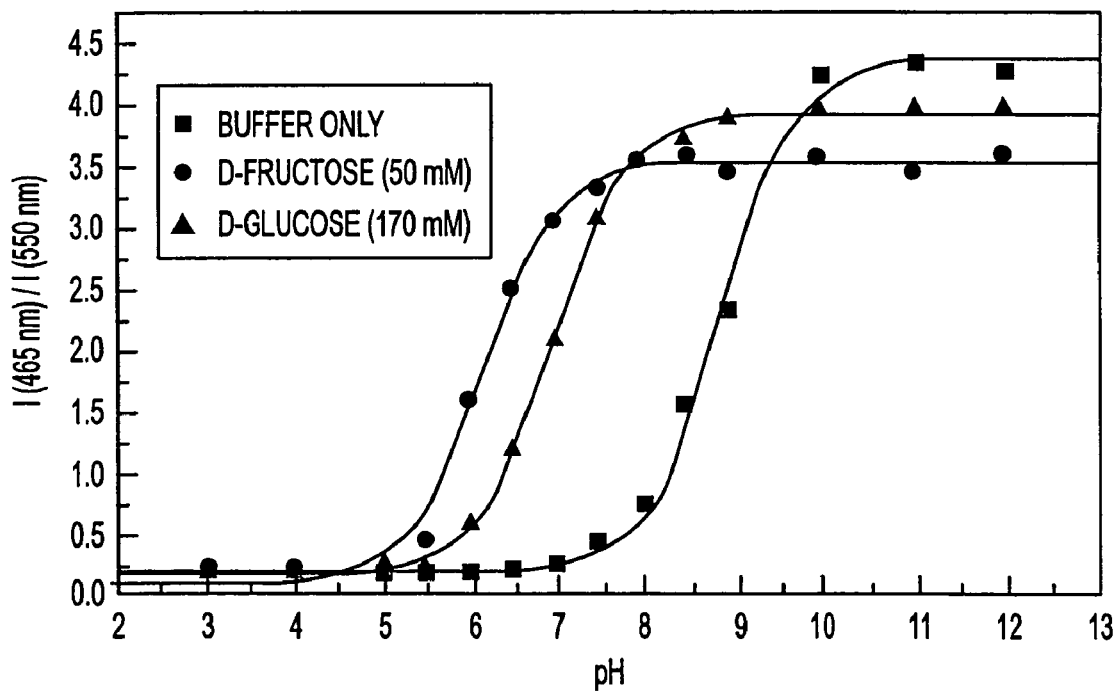
FIG. 12B shows titration curves of compound 4 with and without sugar. All buffer solutions contained 66.6% (v/v) of methanol.
Figure 13B:
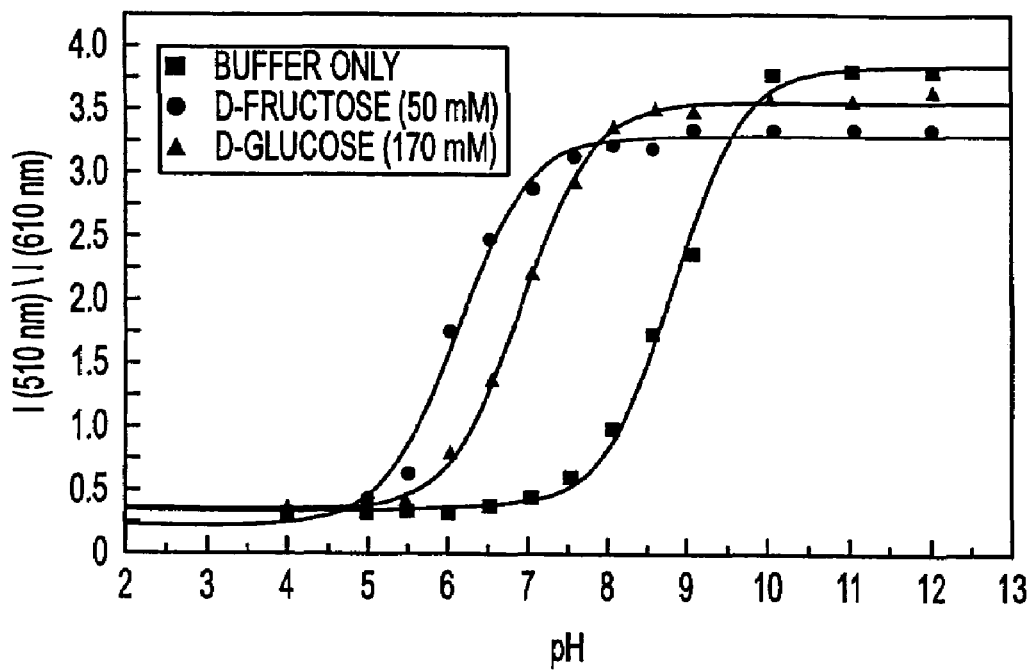
FIG. 13B shows titration curves of compound 5 with and without sugar. All buffer solution contained 66.6% (v/v) of methanol.

FIGS. 12B and 13B show the titration curves, in absence and presence of sugar, against the pH for 4 and 5, respectively. The pK$_a$ values are listed in Table 6. The pK$_a$ values with and without sugar are similar than the pK$_a$ observe for other phenylboronic acid derivatives. As a general trend, the pK$_a$ of the boronic acid: sugar complex is smaller then the uncomplexed boronic acid group. We also observed a decrease of the pK$_a$ of the boronic acid group (with and without sugar) as the molecular length increase. The pK$_a$ values observed for the stilbene derivative (DSTBA) was 9.14 in comparison of 8.90 and 8.75 for 4 and 5, respectively. We attribute this decrease of the pK$_a$ to a decreased involvement of the boron atom in electron delocalization and/or to a more electrophilic boron atom as the molecular length increase. In other word, as the molecule length increase, the partial charge transfer in the ground state between the dimethylamino group and the boronic acid group become smaller and the boron atom is more "available" for a hydroxyl anion. This is in agreement with the fact that the emission shifts between the neutral and anionic forms become smaller as the molecular length increases as discuss previously.

Figure 14A:
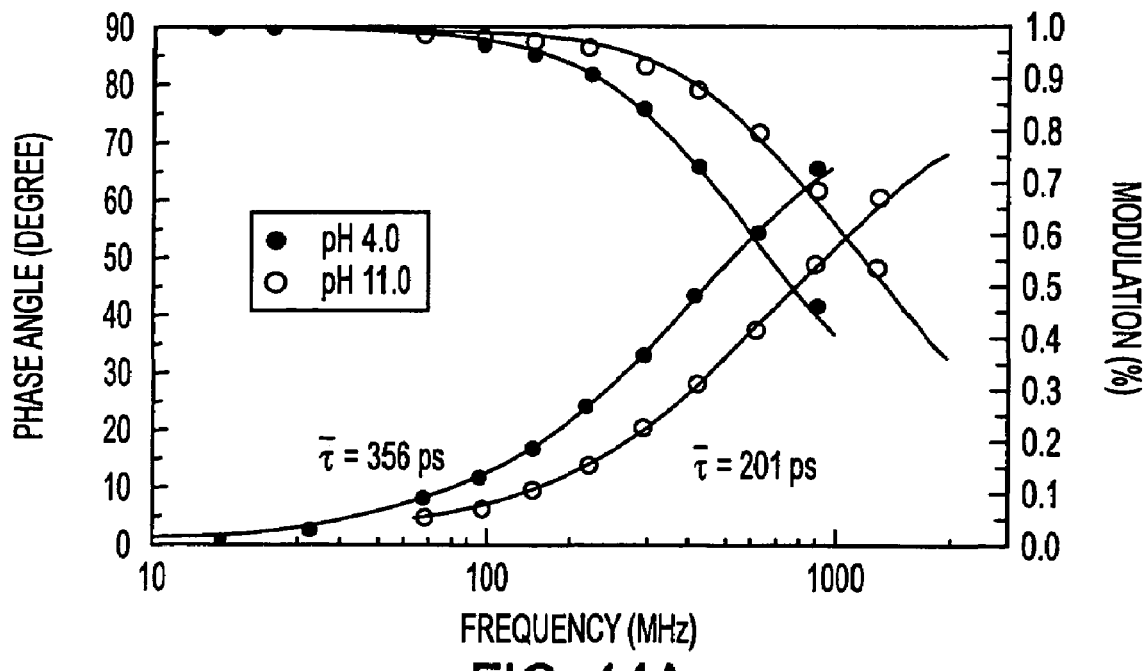
FIG. 14A shows the dependence of pH on the frequency decay profiles of compound 4 at room temperature. All buffer solution contain 66.6% v/v of methanol.
Figure 14B:
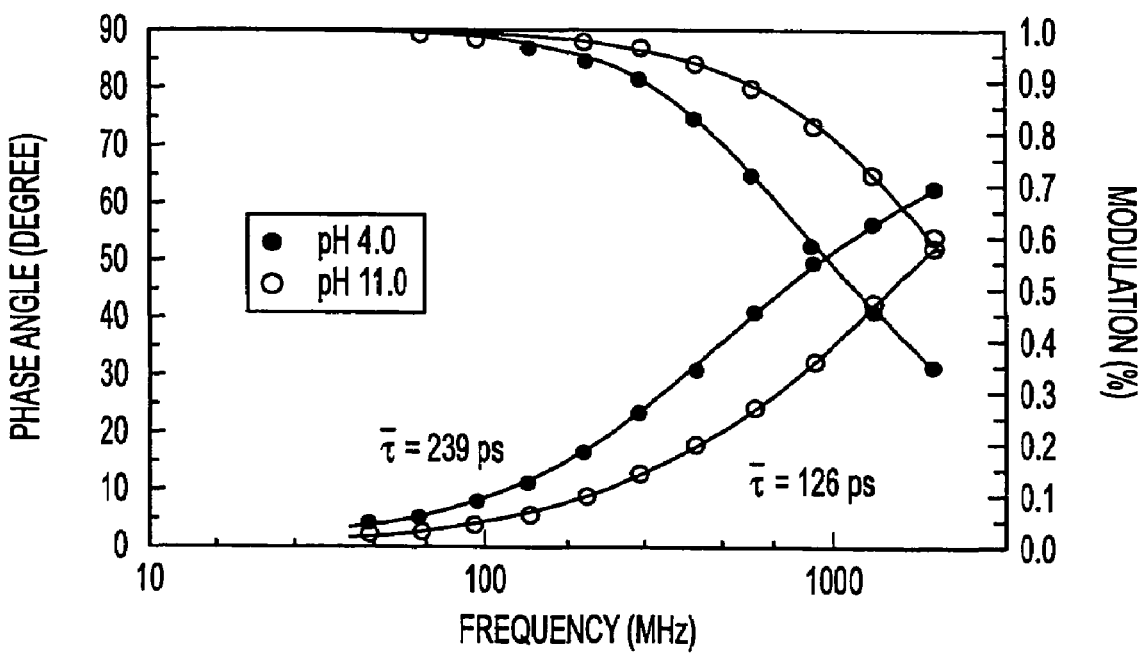
FIG. 14B shows the dependence of pH on the frequency decay profiles of compound 5 at room temperature. All buffer solution contain 66.6% v/v of methanol.

FIG. 14 displays the frequency-domain decay profile of 4 (A) and 5 (B) at pH 4.0 and 11.0. Decay parameters are listed in Table 5. Both compound show a decrease of the mean lifetime at higher pH. Formation of the excited state charge transfer state induces a decrease of the mean lifetime. Since an increase of the pH prevents formation of the CT state, we expected an increase of the mean lifetime at higher pH. At this point, we do not have a clear interpretation of these results and deeper study would be required to understand this effect. We just would like to point out that the change of the electron-withdrawing property of the boronic group following the formation of the anionic form leads to both spectral changes and change in the fluorescence lifetime of the probes. The implication of this observation for sugar sensing will be discuss in the next section.

Sugar Effects on the Spectroscopic and Photophysiscal Properties

Figure 15A:
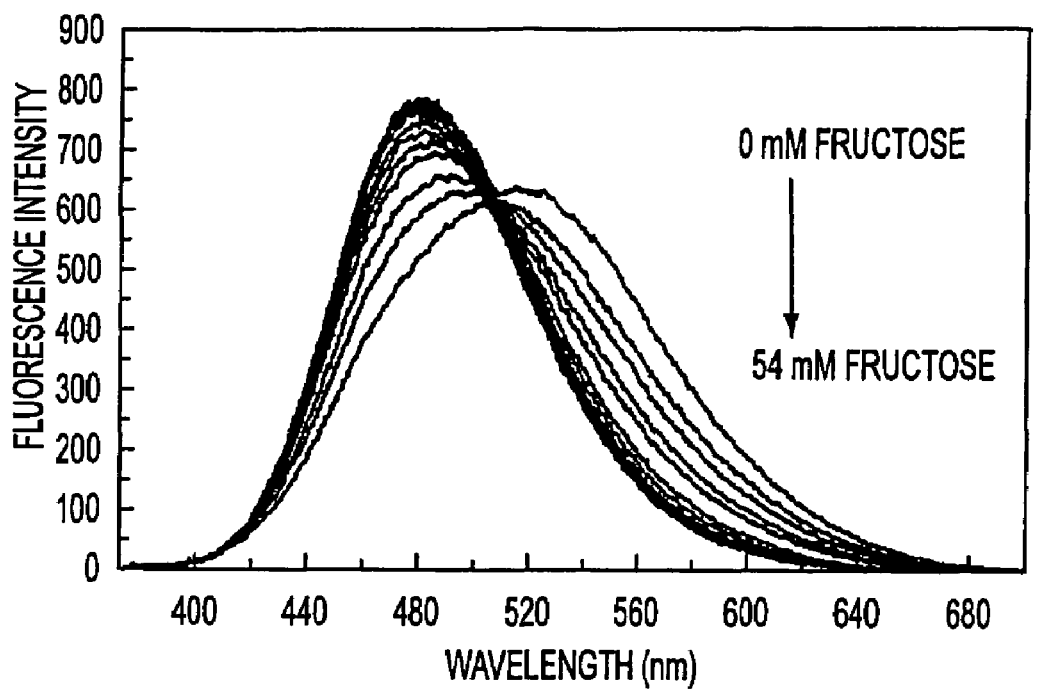
FIG. 15A is a graphical representation of the change in the emission spectra of compound 4 after addition of D-fructose in phosphate buffer pH 8.0/methanol 1:2 (v/v) at room temperature, $\lambda_{ex}=370$ nm.
Figure 15B:
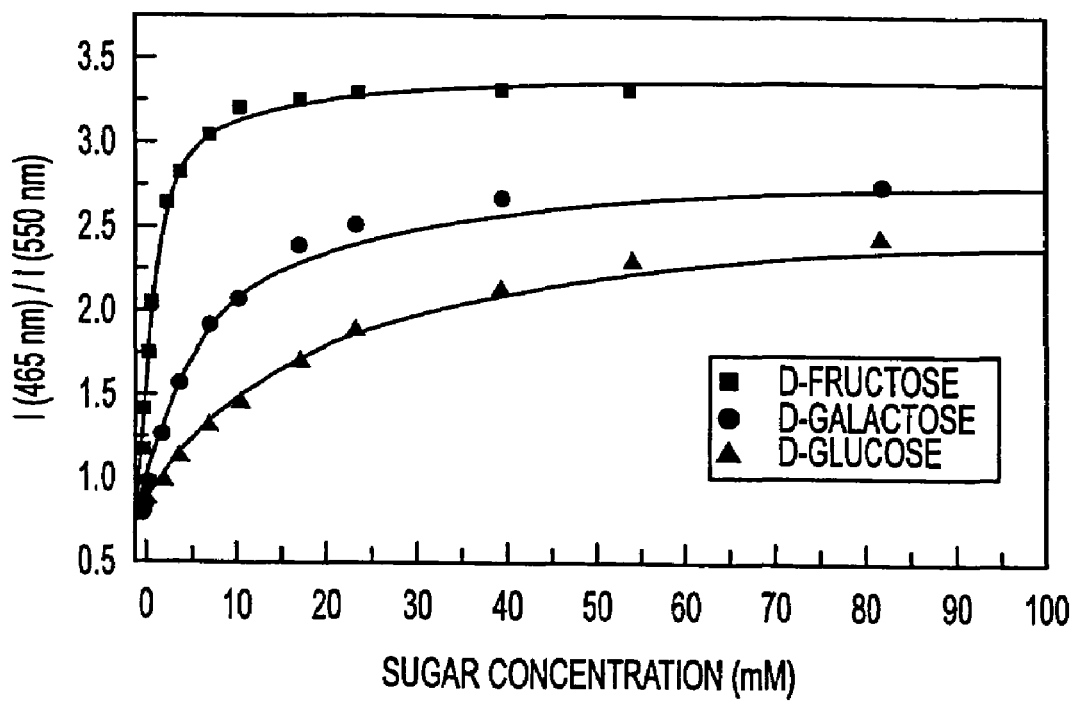
FIG. 15B shows titration curves of compound 4 with different sugars.
Figure 16A:
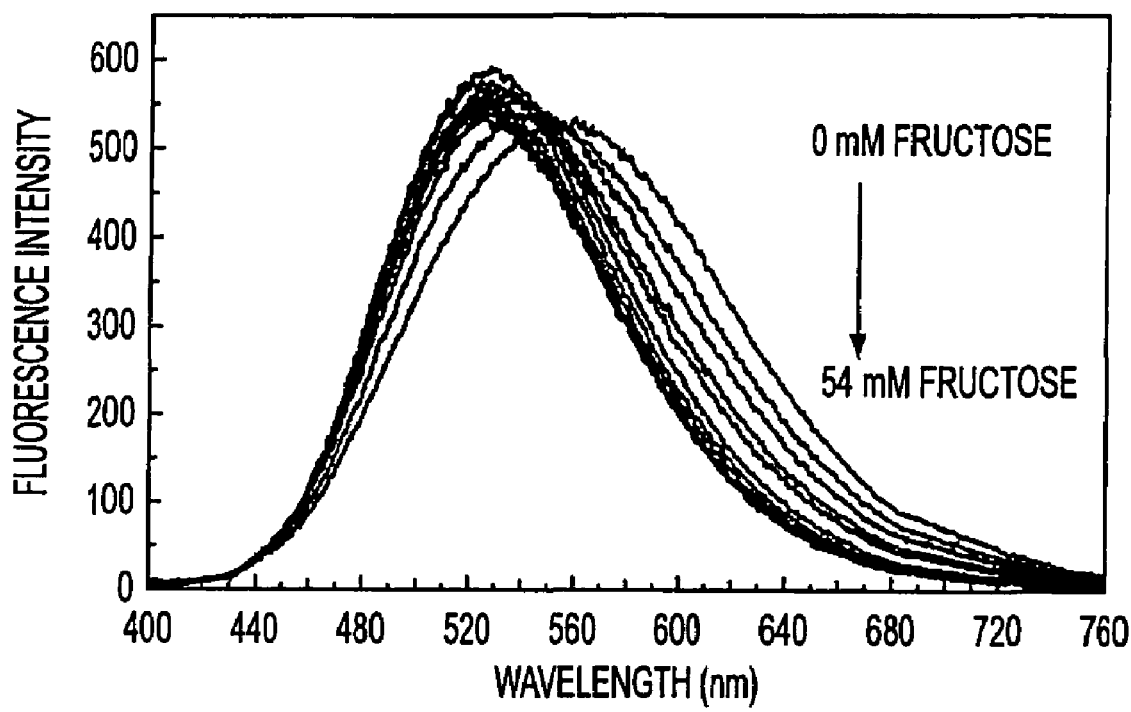
FIG. 16A shows a change in the emission spectra of compound 5 after addition of D-fructose in phosphate buffer pH 8.0/methanol 1:2 (v/v) at room temperature, $\lambda_{ex}=390$ nm.
Figure 16B:
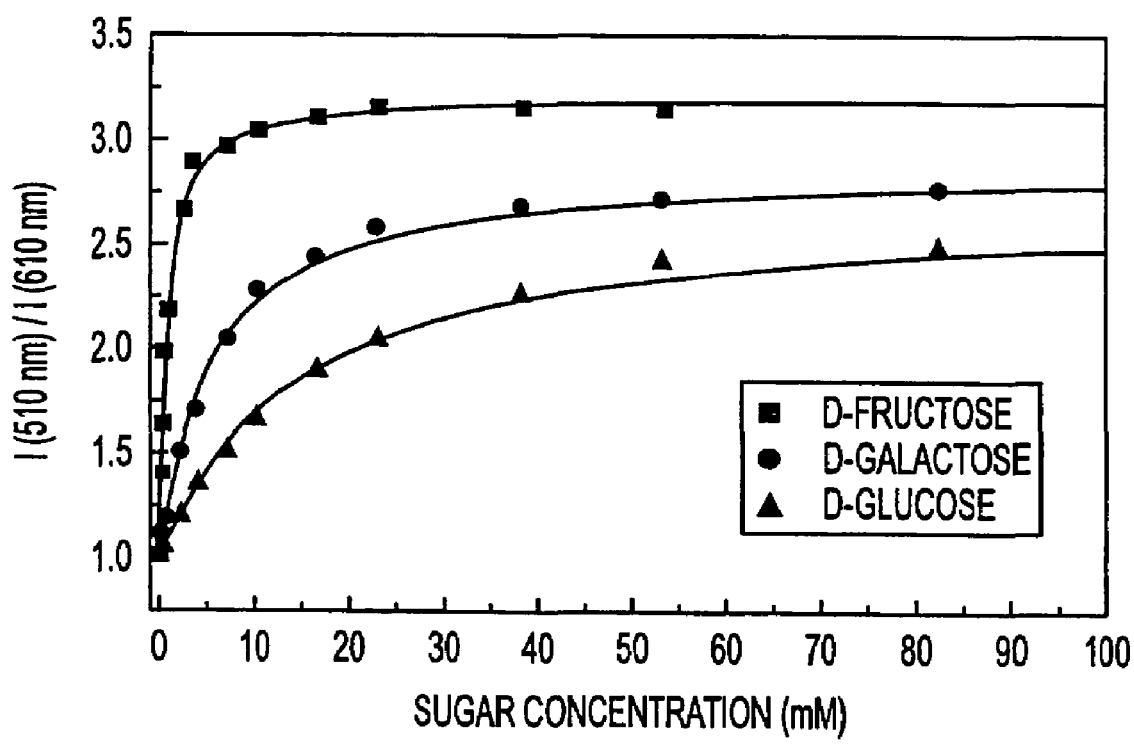
FIG. 16B shows titration curves of compound 5 with different sugars.

The maximal spectral change appears at pH 7.5 for fructose and 8.0 for glucose for both compounds (FIGS. 12B and 13B). We measured the effect of sugar at pH 8.0 to have the same pH for all compound and sugars and for comparison with previous results on stilbene derivatives. For comparison, the spectral change for 4 for fructose at pH 8.0 is only about 6% smaller than at pH 7.5. FIGS. 15 and 16 show the spectral changes following the addition of fructose and the titration curves of fructose, galactose and glucose for 4 and 5, respectively. In both cases, a blue shift of the emission spectra and an increase of the intensities were observed. These spectral changes are interpreted as the lost of the electron-withdrawing property of the boronic acid group following the complexation with sugar. At pH 8.0, the majority of the boronic acid groups are presented under their neutral forms. The anionic forms are created upon the addition of sugar since the $pK_a$ of the complex with sugars is smaller. Spectral changes observed for 4 are quite similar to the changes observed for the stilbene analogue (DSTBA) showing that the CT mechanism could be apply to longer wavelength probes than the UV probes. On the other hand, spectral changes observed for 5 are smaller. This could show that the CT effect decreases in importance with the increase of the length of this family of compounds and other fluorophores must be use to obtain longer wavelength probes for sugars.

Dissociation constants ($K_D$) for the different sugar investigated are listed in Table 6 for 4 and 5. The trend of the $K_D$ for the different sugars is the same as for the other monophenylboronic acid probes presented in the literature. On the other hand, the $K_D$ values show large changes from DSTBA, 4 and 5. The dissociation constants decrease with the increase of the molecular length. This decrease is drastic for the $K_D$ values of galactose and glucose. The decrease is around 3-fold for fructose, near 10-fold for galactose and around 6-fold for glucose dissociation constants from DSTBA to 5. Since the $K_D$ values of 4 and 5 are similar than other monophenylboronic acid probes, we think that for the stilbene derivative the boron atom is much more involved in the electron delocalization and/or the partial charge transfer in the ground state is so large that the nucleophilicity of the boronic acid group is low. This results in the increase of the $pK_a$ of the compound and a decrease of the apparent affinity constants for sugars. As the molecular length increases, the contribution of the boronic acid group to the delocalization decreases and $pK_a$ and affinity constants become more similar than the other monophenylboronic acid derivatives.

Figure 17A:
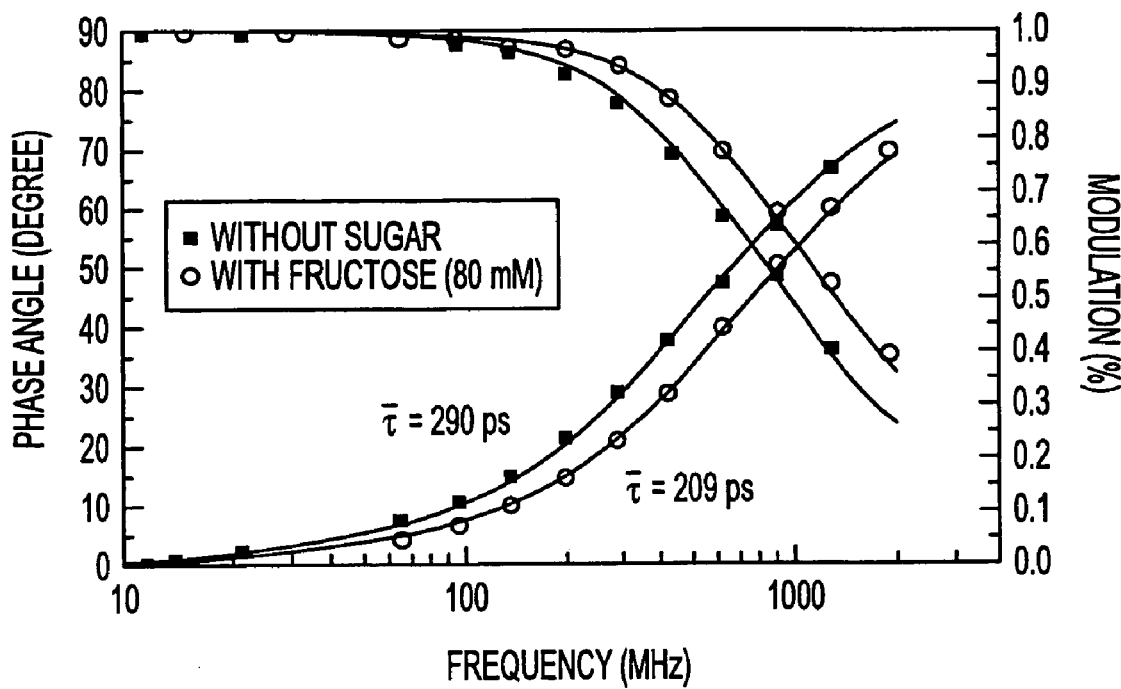
FIG. 17A shows sugar effect on the frequency decay profiles of compound 4 at room temperature in phosphate buffer pH 8.0/methanol 1:2 (v/v).
Figure 17B:
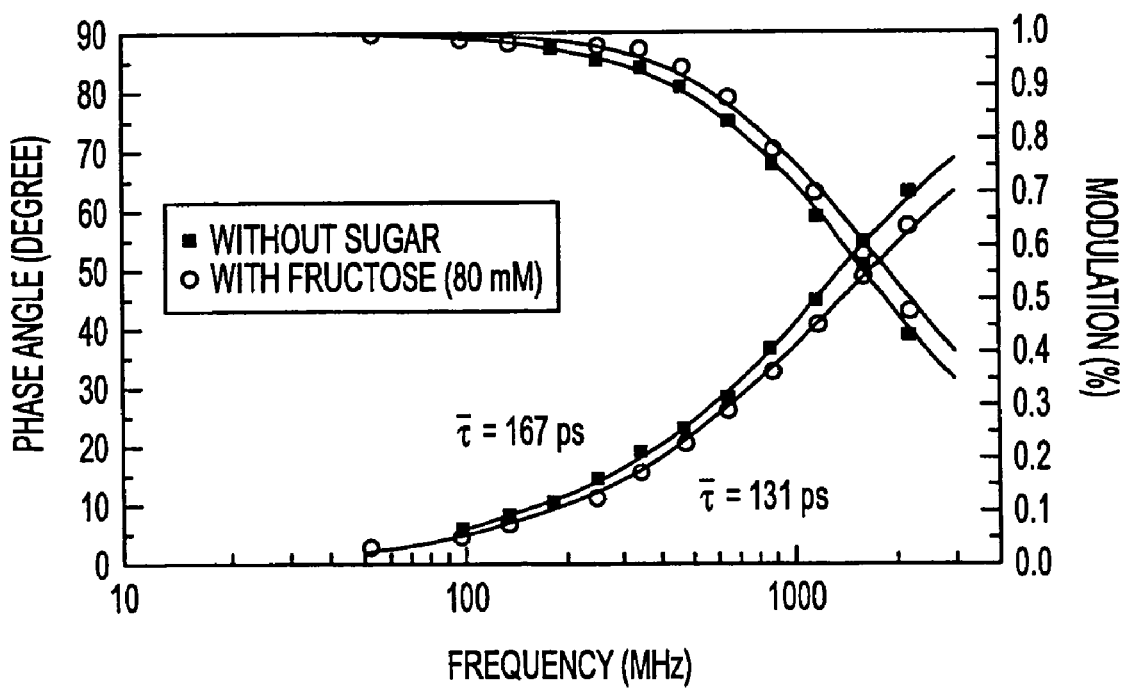
FIG. 17B shows sugar effect on the frequency decay profiles of compound 5 at room temperature in phosphate buffer pH 8.0/methanol 1:2 (v/v).

FIG. 17 displays the frequency-domain decay profiles with and without fructose for 4 and 5. Decay parameters are listed in Table 5. For both compounds, a decrease of the mean lifetime after addition of fructose is observed. The use of the CT mechanism involving the boronic acid group leads not only to spectral changes but also to lifetime changes. For the compounds investigated in this example, these lifetime changes are small. Without being bound by theory, this may be due principally to the presence of a large non-radiative deactivation rate constant present for these polyenes, which minimize the sugar effect. It can be expected that the CT mechanism applied to longer lifetime fluorophores could lead to new probes for glucose displaying useful lifetime changes for use in fluorescence lifetime based sensing.

TABLE 4

Spectroscopic and Photophysics properties of Investigated Compounds 4 and 5

| | solvent | $\lambda_{Abs}$ (nm) | $\lambda_F$ (nm) | $\Delta$ (cm$^{-1}$) |
|---|---|---|---|---|
| 4 | CH | 377 | 441 | 3850 |
| | WM | 368 | 551 | 9025 |
| 5 | CH | 396 | 470 | 3975 |
| | WM | 390 | 580 | 8400 |

CH: cyclohexane;
WM: water/methanol (1:2);
$\Delta$: Stokes' shift

TABLE 5

Intensity Decay Parameters of 4 and 5 in Different Environments

| | Enviro. | $\tau_1$ (ps) | $\tau_2$ (ps) | $\alpha_1$ | $\alpha_2$ | $f_1$ | $f_2$ | $\tau_F$ (ps) | $\chi_R^2$ |
|---|---|---|---|---|---|---|---|---|---|
| 4 | CH | 621 | — | 1.0 | — | 1.0 | — | 621 | 2.65 |
| | WM | 357 | — | 1.0 | — | 1.0 | — | 357 | 1.12 |
| | pH 4.0 | 356 | — | 1.0 | — | 1.0 | — | 356 | 1.57 |
| | pH 11.0 | 201 | — | 1.0 | — | 1.0 | — | 201 | 1.92 |
| | No fructose | 290 | — | 1.0 | — | 1.0 | — | 290 | 1.95 |
| | Fructose | 209 | — | 1.0 | — | 1.0 | — | 209 | 1.62 |
| 5 | CH | 750 | — | 1.0 | — | 1.0 | — | 750 | 1.73 |
| | WH | 97 | 280 | 0.41 | 0.59 | 0.2 | 0.8 | 244 | 0.33 |
| | pH 4.0 | 60 | 265 | 0.4 | 0.6 | 0.13 | 0.87 | 239 | 0.35 |
| | pH 11.0 | 105 | 370 | 0.98 | 0.02 | 0.92 | 0.08 | 126 | 0.28 |
| | No fructose | 134 | 607 | 0.98 | 0.02 | 0.93 | 0.07 | 167 | 1.33 |
| | Fructose | 83 | 171 | 0.63 | 0.37 | 0.45 | 0.55 | 131 | 1.51 |

CH: cyclohexane;
WM: water/methanol (1:2);
pH 4.0 and 11.0: buffer with 66.6% methanol; with and without fructose: phosphate buffer pH 8.0 with 66.6% methanol.
The values of $\chi_R^2$ were calculated using uncertainties in the phase and modulation of $\delta p = 0.01$ and $\delta m = 0.5$, respectively.

TABLE 6

$pK_a$ and Dissociation Constants ($K_D$) for 4 and 5 in Presence of Different Saccharides

| | $pK_a$ | | | $K_D$ (mM) | | |
|---|---|---|---|---|---|---|
| | no sugar | fructose (50 mM) | glucose (170 mM) | fructose | galactose | glucose |
| DSTBA[a] | 9.14 | 6.61 | 8.34[b] | 2.5 | 49 | 98 |
| 4 | 8.90 ± 0.04 | 6.19 ± 0.04 | 6.97 ± 0.02 | 1.12 ± 0.05 | 5.9 ± 0.6 | 17 ± 2 |
| 5 | 8.75 ± 0.04 | 6.10 ± 0.05 | 6.86 ± 0.02 | 0.84 ± 0.03 | 5.4 ± 0.4 | 15 ± 1 |

[a]from reference 3.
[b]in presence of 50 mM of glucose.

EXAMPLE 3

In attempt to develop additional fluorescent probes for glucose detection, the following compound 6 was synthesized as shown in the following reaction scheme:

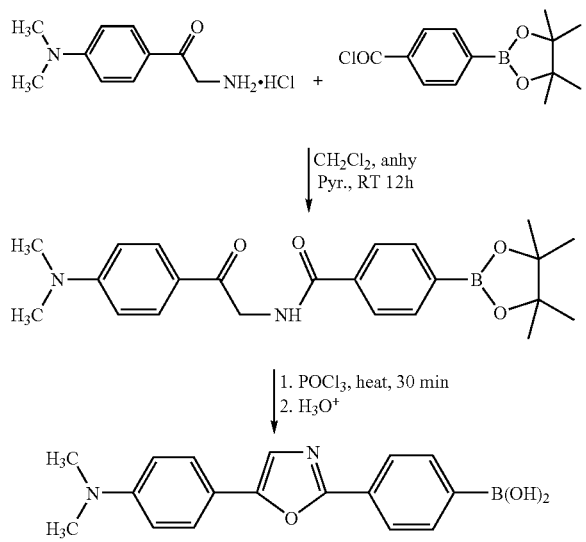

Figure 18:
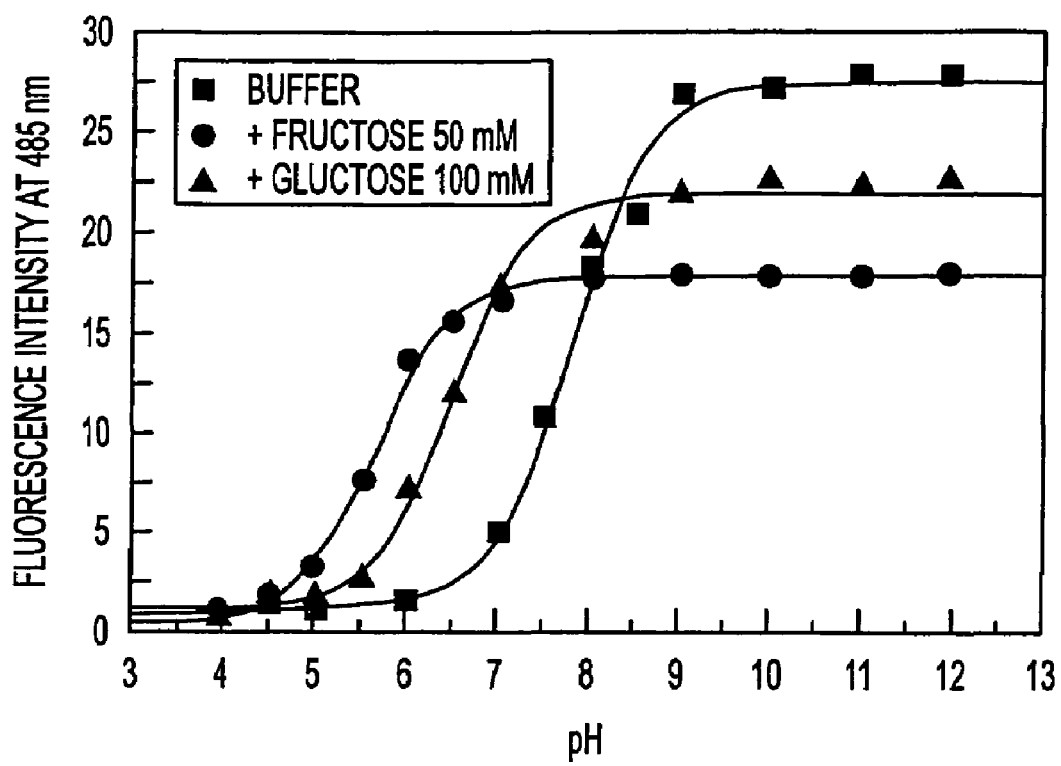
FIG. 18: Titration curves of 6 against the pH in absence and presence of sugars, $\lambda_{ex}=350$ nm.

Compound 6 is readily synthesized from the reaction between the 2-amino-4'-dimethylaminoacetophenone hyrochloride (Synthesized from 4'-Dimethylaminoacetophenone (TCI america) according to the standard procedure described in the literature (57-58) and the 4-(4,4,5,5-tetramethyl-1,3,2-dioxaborolan-2-yl)benzoic acyl chloride, obtained from the commercially available 4-(4,4,5,5-tetramethyl-1,3,2-dioxaborolan-2-yl)benzoic acid refluxed in $SOCl_2$, following by the dehydratation of the product in $POCl_3$ (59). Donor/acceptor derivatives of diphenyloxazole are well known to show high fluorescence quantum yields, long wavelength emission and to be very sensitive to small variations affecting the ICT property of the excited state. In this case, the ICT state is between the boronic acid, the electron-withdrawing group, and the N,N-dimethylamino group, the electron-donating group. As the boronic acid group changes to its anionic form the electron-withdrawing property of the boron is removed and then the ICT is affected as shown in the following reaction scheme:

As the pH increases, one can observe a blue shift (results not shown) and an important increase of the fluorescence intensity. The emission band of the neutral form appears at 557 nm with a $f_F$ of 0.03, on the other hand, the emission of the anionic form appears at 488 nm with a $f_F$ of 0.95. These important spectral changes are interpreted by the lost of the ICT property for the anionic form. The intensity change following the pH change is shown in FIG. 18. Nearly a 30-fold increase of the fluorescence intensity can be observed at 485 nm. Usually, the effects of sugars are observed since the complex boronic acid: sugar has a lower $pK_a$ than the uncomplexed boronic acid. At a selected pH, it is possible to have a predominance of the neutral form in absence of sugar and a predominance of the anionic form in presence of sugar. This conformational change of the boron group, induced by the presence sugar, is the origin of the spectral changes observed. Titration curves of 6 in presence of the sugar are displayed in FIG. 18. The observed $pK_a$ of 6 is 7.8 in absence of sugar, $pK_a$ of 5.6 and 6.5 are obtained in presence of fructose and glucose, respectively. Maximum changes between the titration curves with and without sugar are obtained at pH 6.5 and 7.0 for fructose and glucose, respectively. Since the spectral changes induced by sugar are not so different between these two pH values, we performed our measurements at pH 7.0 for all saccharides. It is also interesting to note that large spectral changes could also be observed at pH higher than 9.0 as seen in FIG. 18. This suggests that probe 6 could also be used for monitoring sugar at high pH.

Figure 19:
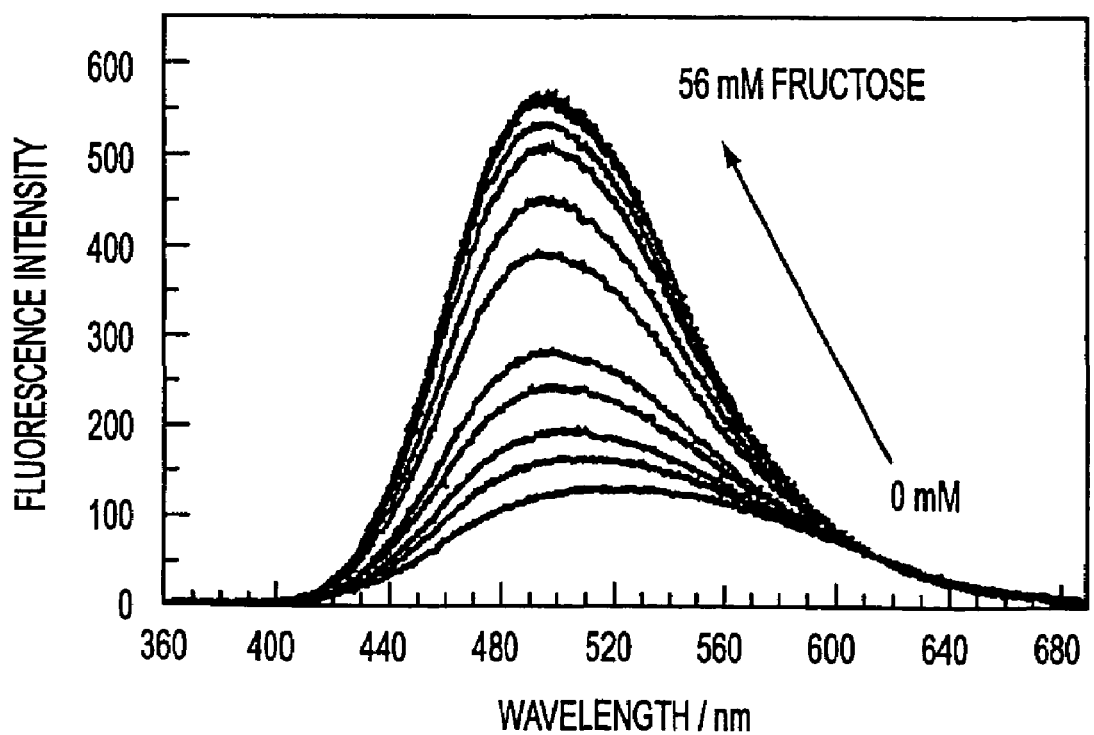
FIG. 19: Effect of the Fructose on the emission of 6, measured in phosphate buffer/methanol (2:1 v/v) at pH 7.0, $\lambda_{ex}=350$ nm. Probe concentration: $5\times10^{-6}$ M.
Figure 20:
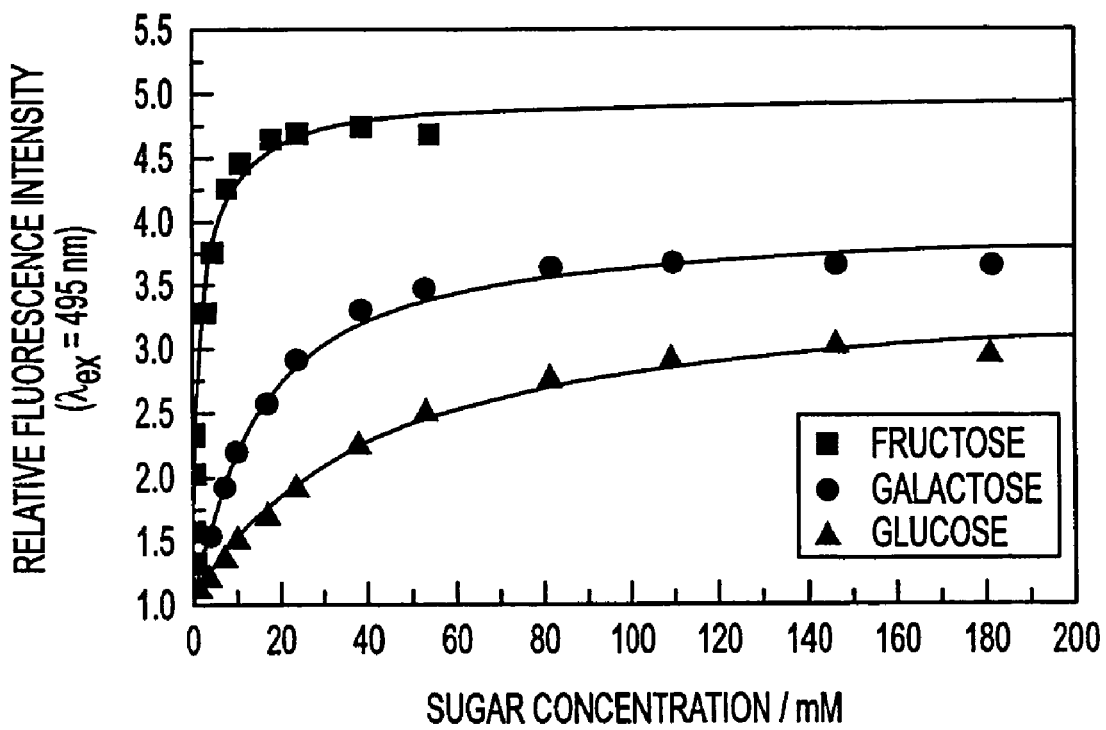
FIG. 20: Titration curves of 6 against sugars, measured in phosphate buffer/methanol (2:1 v/v) at pH 7.0, $\lambda_{ex}=350$ nm. Probe concentration: $5\times10^{-6}$ M.

The effect of fructose on the emission band of 6 is displayed in FIG. 19. As observed for the pH, the presence of the sugar induces a blue shift and an increase of the fluorescence intensity. An isobestic point is observed at 615 nm showing the equilibrium of the two conformations, the neutral and anionic form of the boronic acid. The same isobestic point was observed in the pH effect on the emission band. The increase of the emission intensity is about 5-fold in presence of fructose and about 3-fold in presence of galactose and glucose. Titration curves of 6 against sugars are displayed in FIG. 20. Dissociation constants ($K_D$) of 6 were calculated at 1.9±0.1 mM for fructose and 14±1 mM and 37±3 mM for galactose and glucose, respectively. $K_D$ values are comparable to previous values obtained with donor/acceptor chromophore involving the boronic acid group[6,7]. The higher affinity of the monoboronic acid 6 for fructose in comparison with glucose and the high concentration range of practical usefulness of 6 for glucose would not be suitable for glucose sensing in biological samples and/or in presence of fructose

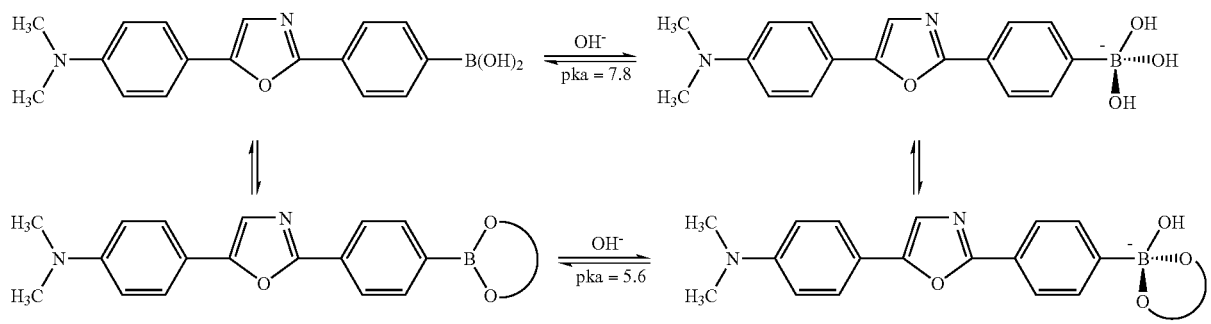

but could find applications in the food industry and/or in fermentation industry were high concentration glucose are used.

In addition to the observed changes in the steady-state emission properties of 6, changes in the fluorescence lifetime of the probes were also observed. The neutral structure, 6, showed a monoexponential fluorescence decay with a lifetime of 1.7 ns while the anionic form 2 possesses a lifetime of 3.7 ns, also monoexponential. At pH 7, the presence of fructose changes the fluorescence lifetime of the probe from 2.8 ns to 3.6 ns. Fluorescence lifetime changes are useful for sensing and monitoring since they are independent of the total intensity and independent also from the power of the excitation source and the concentration of the probe.

Selected data for 6 (5-(4'-Dimethylaminophenyl)-2-(4"-boronophenyl)oxazol: yellow solid, yield 48%, $\delta_H$(300 MHz; $CD_3OD$) 2.83 (6H, s), 6.59 (2H, d), 7.05 (1H, s), 7.40 (2H, d), 7.52 (1H, s), 7.67 (1H, s) and 7.82 (2H, s).

EXAMPLE 4

The use of decay times (as opposed to intensities) would be a preferred method because the decay times are mostly independent of the probe concentrations or the signal of the fluorescence signal. The frequency-domain or phase-modulation method for sensing is well recognized for the instrumental simplicity, rapid data acquisition, and ability to detect small changes in phase angle or lifetime. A mean lifetime can be measured at a single modulation frequency using simple light emitted diodes or laser diodes (60-61). Importantly, lifetime can be measured in highly scattering media (62-63), and have been successfully measured through several layers of chicken skin (64). We present, in this study, the evaluation for fluorescence lifetime based sensing of two anthracenes compounds having the phenyl boronic acid group and showing removal of PET quenching upon binding glucose. The results show a considerable change in the phase angle and in the modulation for both compounds. Evaluation for fluorescence lifetime based sensing of two anthracene compounds having the phenyl boronic acid group as shown below were performed.

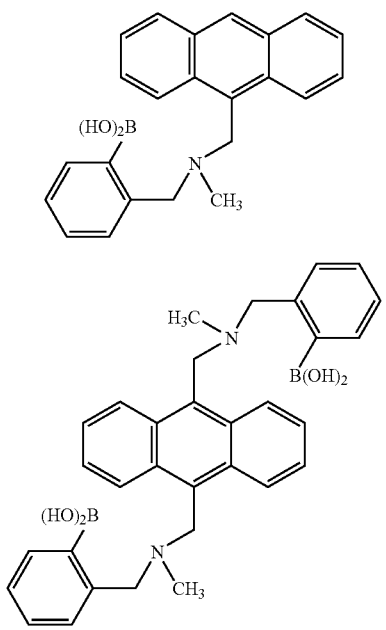

Fluorescence lifetimes were obtained with the phase-modulation method and the excitation was provided by a UV-LED source. The results show a considerable change in the phase angle and in the modulation for both compounds. Titration curves in presence of BSA and micelles have been measured in order to evaluate the possible interference from biosystems. Results on the reversibility are also presented showing a complete reversibility of the association between the boronic acid group and glucose.

Steady-State Measurements

Figure 21A:
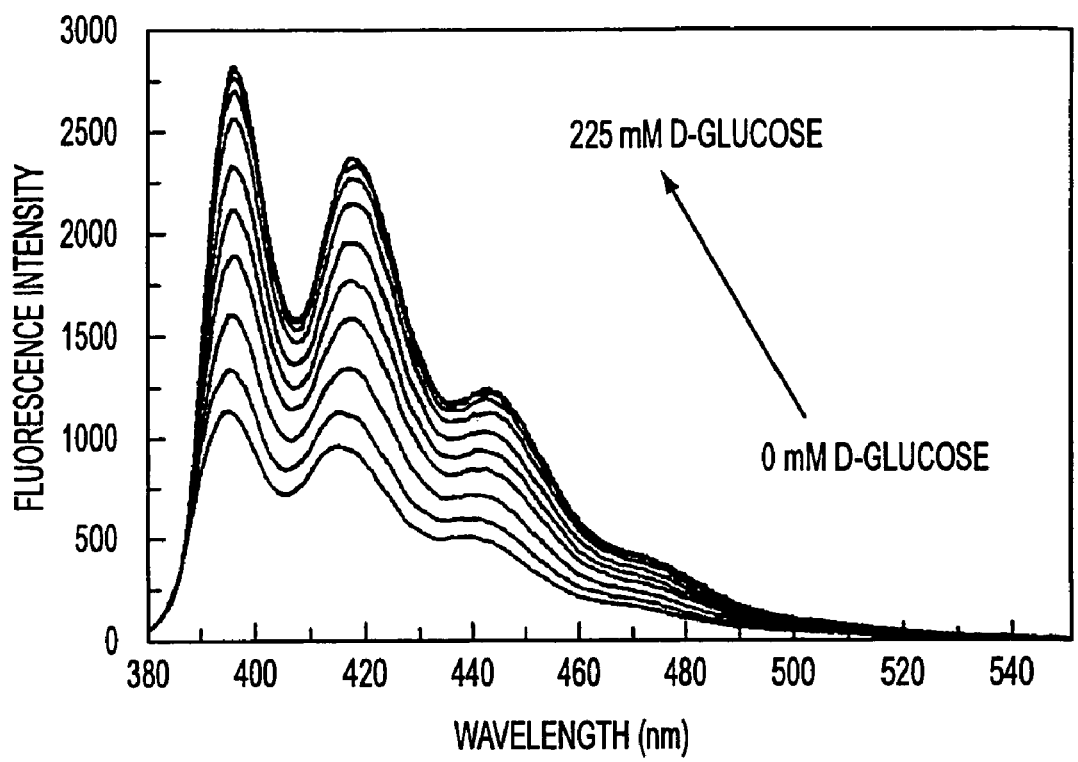
FIG. 21: Fluorescence spectral changes of 7 (A) and 8 (B) in methanol/phosphate buffer pH 7.7 (1:3). $\lambda_{ex}$: 365 and 380 nm for 7 and 8 respectively. Measured at room temperature.
Figure 21B:
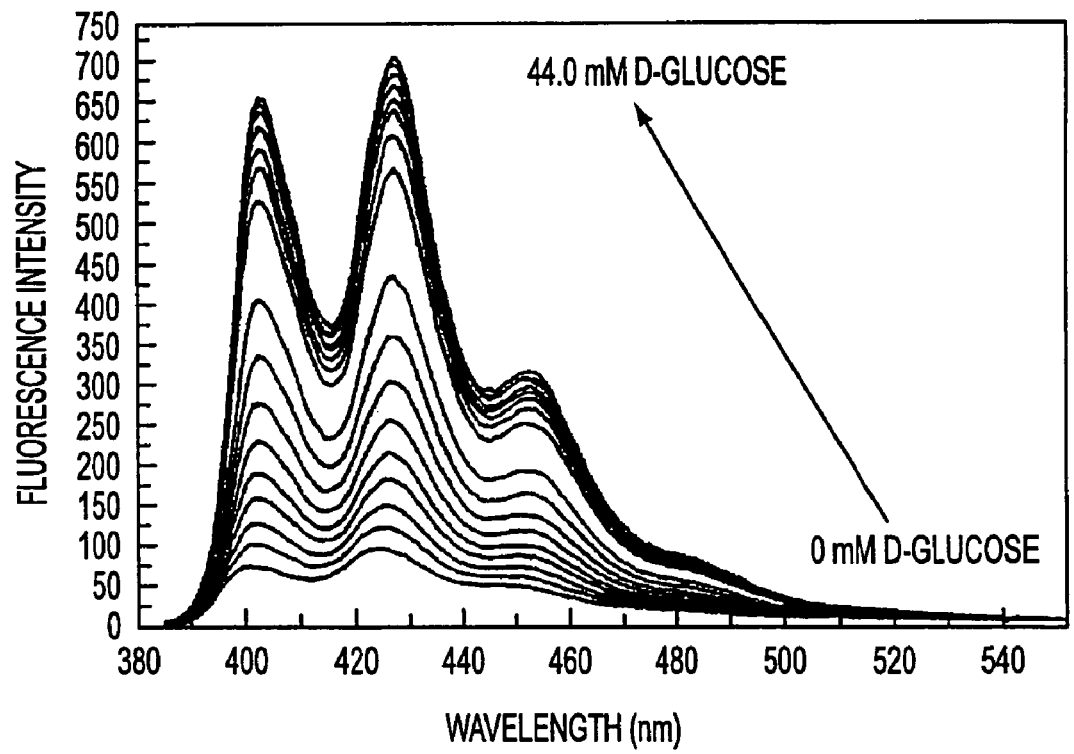
Figure 22A:
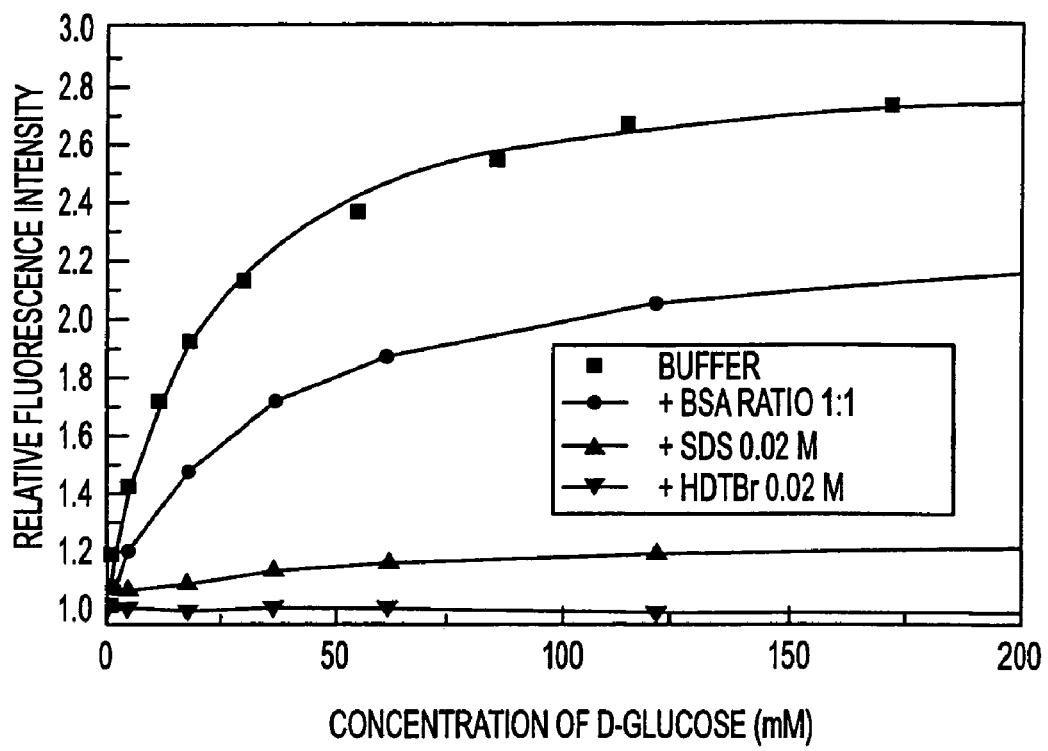
FIG. 22: Titration curves against D-Glucose obtained with the steady-state intensity for 7 (A) and 8 (B) in absence and presence of BSA and micelles. $\lambda_{ex}$: 420 and 425 nm for 7 and 8 respectively.
Figure 22B:
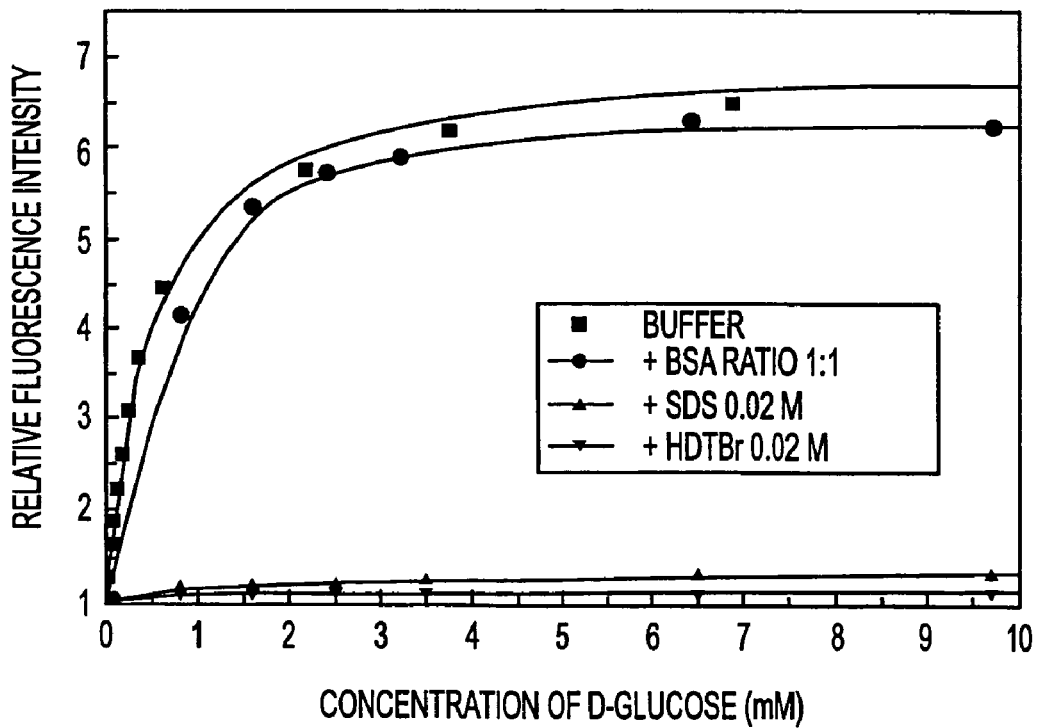

Emission spectra and corresponding titration curves for 7 and 8 are presented in FIGS. 21 and 22 respectively. Stability constants and dissociation constant are presented in Table 7. As discussed in the literature, the change is the intensity is attributed to the removal of the PET quenching due to the interaction between the boron and nitrogen atoms following the binding with glucose. In attempt to see the possible interference from macrobiosystems, titration curves have also been measured in presence of BSA and two detergents, one with a negative charged head group (HDTBr) and the other with a positive charged head group (SDS). BSA has a little effect on the titration curve of 7 and no effect for compound 8. The effect of BSA one compound 7 could be the result of an interaction between these two compounds. But, as the measurements are taken in a mixture of methanol and water, aggregation could not be neglect. Both compounds 7 and 8 show a relatively low solubility due to the high hydrophobicity of both the anthracene and phenyl part. To obtain a reproducible titration curve, vigorous stirring and time must be applied. In the presence of micelles, a complete inhibition of the intensity change is observed. These results suggest that, in presence of micelles, the probes is located in the micelle and cannot interact with the glucose present in solution. For compound , the dissociation constant is in the millimolar range which is characteristic with the boronic acid group. For compound 8, this dissociation constant goes down to submillimolar range. This is due to the ability of both boronic acid group present on compound 8 to bind one molecule of glucose. This is not characteristic just for this compound, but is general for the majority of probes possessing two linker groups.

Frequency Domain Measurements

Figure 23A:
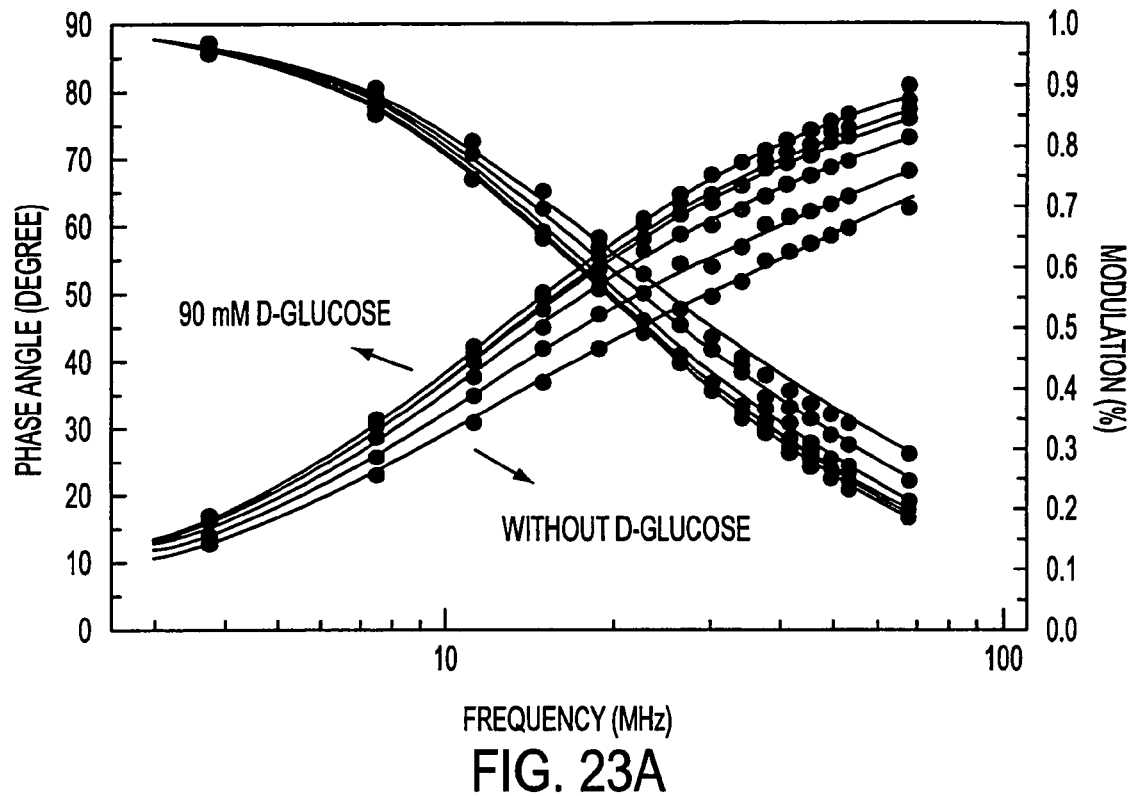
FIG. 23: D-Glucose effect on the frequency-domain decay profiles for 7 (A) and 8 (B) in absence and presence of D-glucose in methanol/phosphate buffer pH 7.7 (1:3).
Figure 23B:
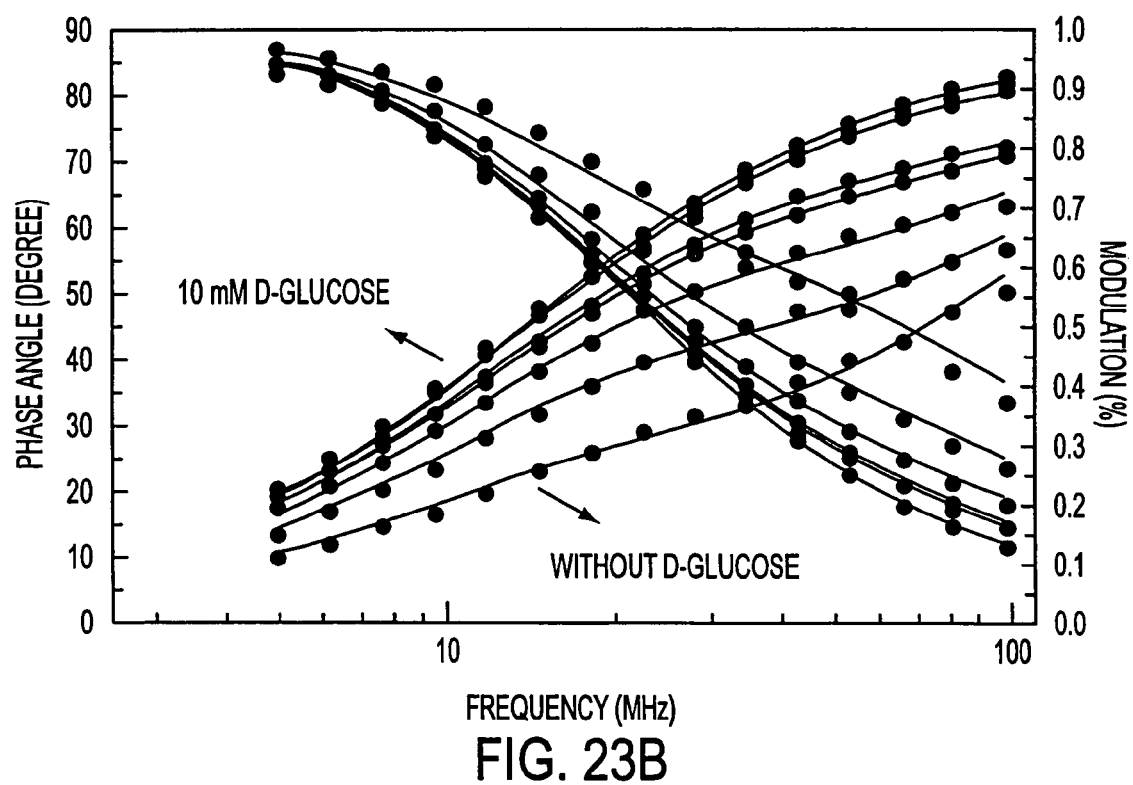

FIG. 23 shows the frequency domain intensity decays for 7 and 8. For both probes, the frequency responses display a significant shift to low-modulation frequencies with the addition of D-glucose, indicating a longer mean lifetime in presence of glucose. These results are consistent with the decrease of the PET quenching in presence of glucose. The intensity decays, for both probes, were satisfactorily fitted to the two-exponential model in absence and presence of glucose, except a single-exponential model was satisfactorily fitted in presence of high concentration of glucose. For both compounds, a short lifetime ($\tau_i$ in Tables 8 and 9) component is present and show an important contribution ($\alpha_i$) of the mean lifetime in absence of glucose. This component increase in lifetime while the contribution in the mean lifetime decrease with the addition of glucose until the decay profile becomes monoexponential. Compound 8 shows a smaller mean lifetime in comparison with 7, 5.7 vs 9.5 ns respectively, in absence of glucose. At the saturation limit, both compounds show a much more similar mean lifetime, 11.8 vs 12.6 ns for 8 and 7 respectively. Without being bound by theory, the smaller mean lifetime of 8 without glucose is probably due to the more efficient quenching when two amino groups are present on the molecule in comparison with one amino group for 7. The similar lifetime observed for both compounds and monoexponential decay for 8, at the saturation limit, imply, not only that both boronic acid groups are involved in the binding with glucose as suggest with the steady-state results, but both boronic acid groups interact with the nitrogen atom causing a removal of the PET quenching similar than observed for compound 7.

Figure 24A:
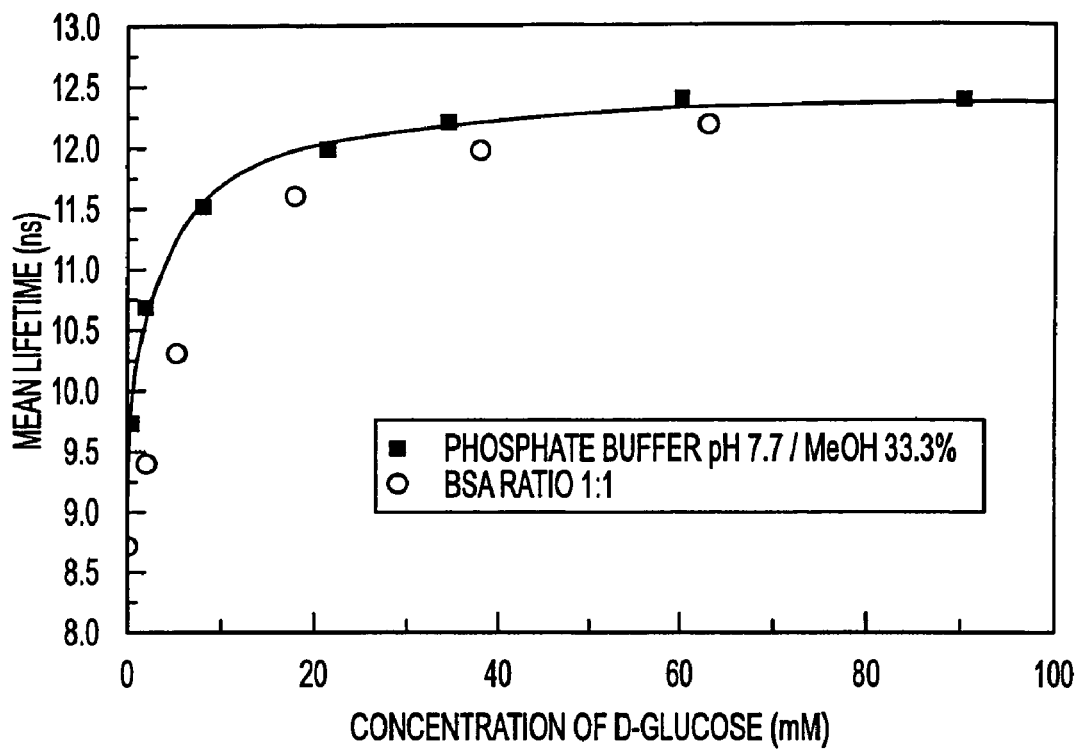
FIG. 24: Titration curves against D-Glucose obtained with the frequency-domain intensity decay for 7 (A) and 8 (B) in absence and presence of BSA.
Figure 24B:
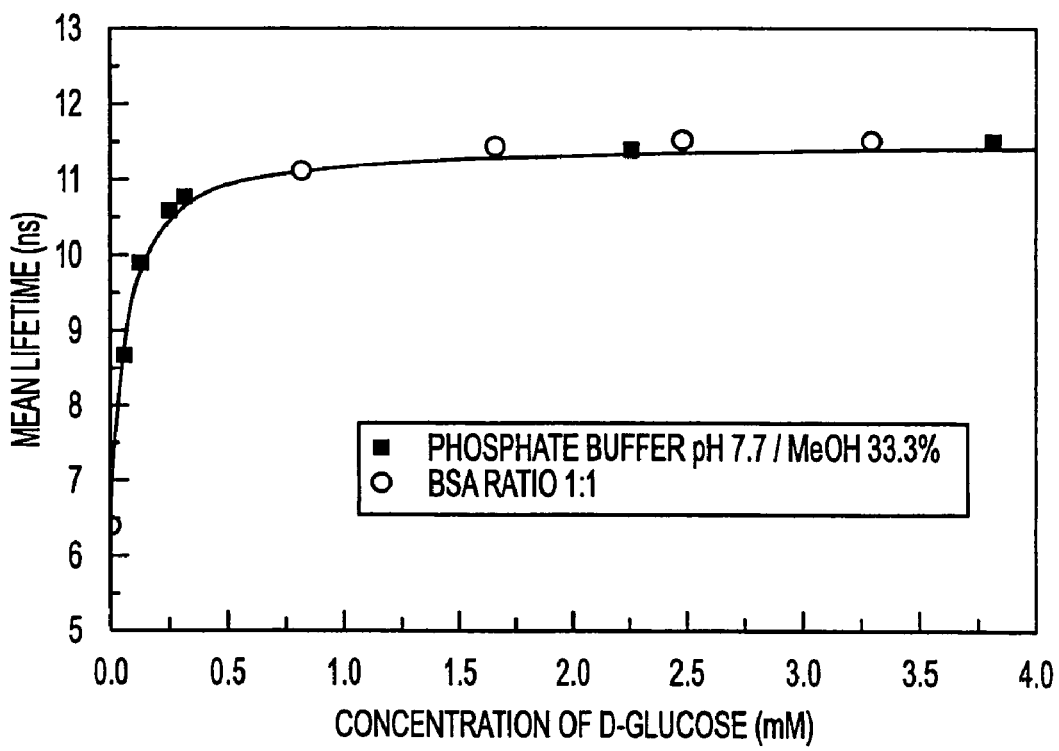
Figure 25A:
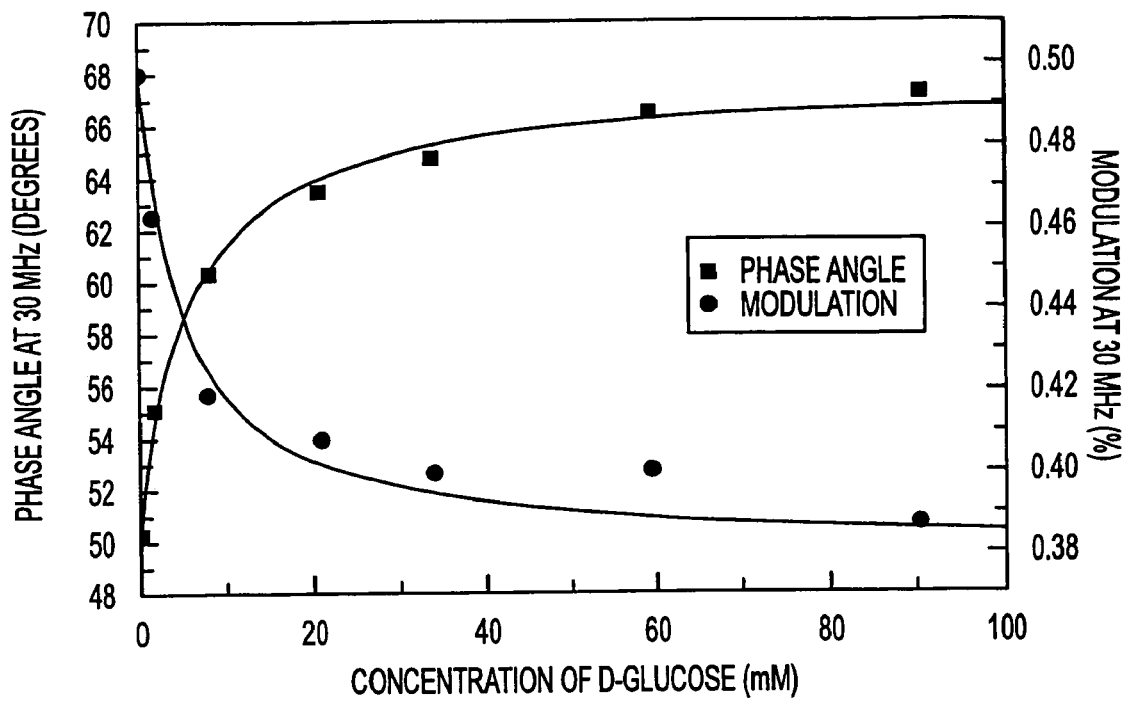
FIG. 25: Effect of glucose on modulation and phase angle measured at 30 MHz for 7 (A) and 8 (B).
Figure 25B:
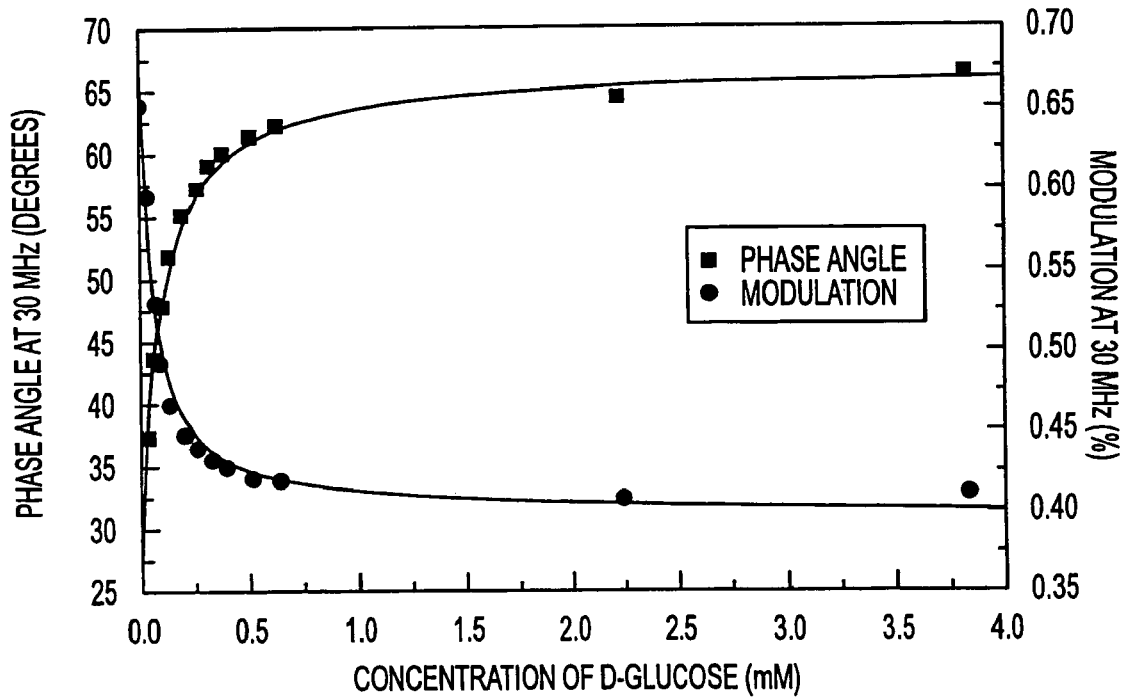

Titration curves obtain with the mean lifetime and with the phase angle and modulation are shown in FIGS. 24 and 25 respectively for both compounds. Despite a relatively small mean lifetime change, compound 7 shows an interesting change in the phase angle and modulation at 30 MHz (FIG. 24A). This is due to the fact that the short lifetime component becomes less important and gradually the decay become more monoexponential with the addition of glucose. For compound 8, the combination of larger mean lifetime change and decrease of the short lifetime component result in a larger change in the phase angle and modulation with the presence of glucose. Stability constants and association constants are presented in Table 7. The apparent association constants obtained with the mean lifetime, phase angle and modulation show a decrease of an order in comparison with the $K_D$ obtained with the steady-state intensity change. Using the frequency domain measurements, probe 7 shows a sensitivity for glucose in the range of few millimolar while the sensitivity for 8 is in the range of tens of micromolar. This is due to the more important contribution of the complex (probe with analyte) on the lifetime because of the higher quantum yield and longer lifetime of the latter. As shown in FIG. 23, the presence of BSA does not interfere in the interaction between the probes and glucose. The effect of BSA on the titration curve of 7 FIG. 23A, is much less than what observe with the steady-state, suggesting than the effect observe with the steady-state could be due to an artifact like aggregation.

Figure 26A:
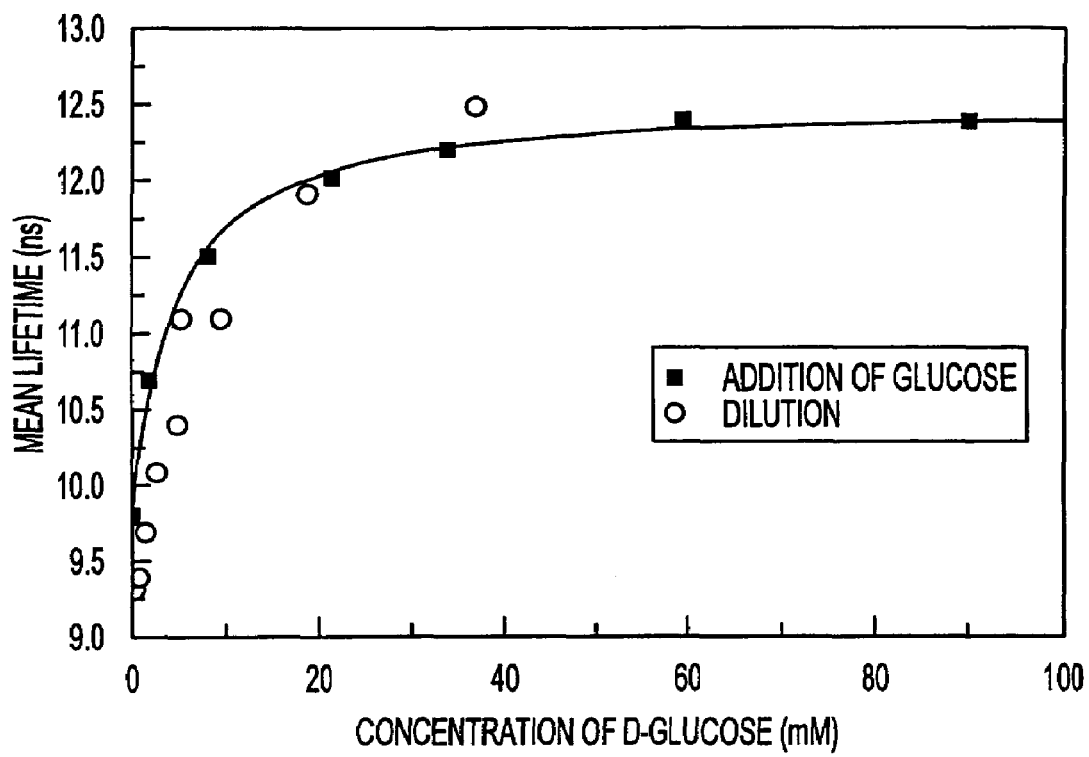
FIG. 26: Dilution effect on the mean lifetime for 7 (A) and 8 (B) in methanol/phosphate buffer pH 7.7 (1:3).
Figure 26B:
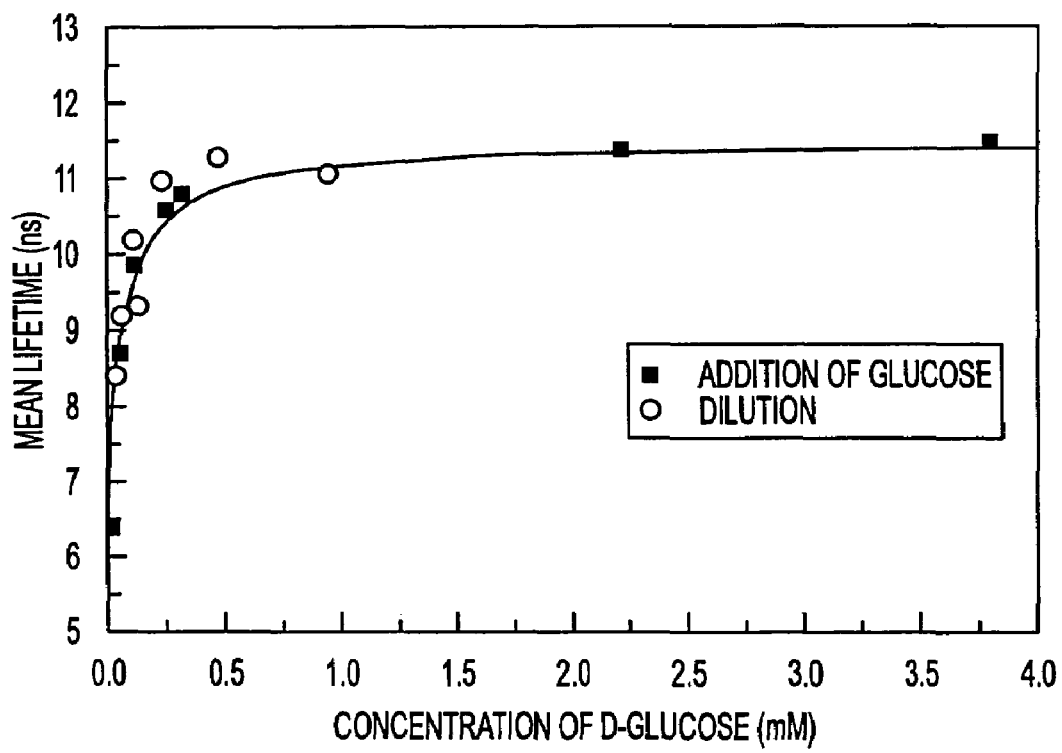

FIG. 26 shows the effect of dilution on the mean lifetime for probe compounds 7(A) and 8(B). The dilution is done with solvent only and not with a solution of free probes. As seen in FIG. 26, the dilution result in a decrease of the mean lifetime. This decrease is comparable to the increase obtained by the addition of glucose. This seems to confirm that the association equilibrium between the probe and the glucose in independent of the concentration of the probes, as assumed in the literature and suggested by the utilization of a single order model in the fitting of the titration curves. It shows, also, that the covalent bond between the boronic acid group and the saccharide is completely reversible.

The development of synthetic probes combines with the development in fluorescence sensing is an interesting way for the improvement and/or for new approaches in glucose sensing. The synthetic probes of the present Example show an interesting intensity change combined with different affinities for glucose. In addition, they also show an interesting change in the fluorescence intensity decay profiles in response to the glucose. Combined with the fact that a simple UV-LED could be use as light source, the probes are very promising as probes for fluorescence lifetime base sensing. In addition, the use of the intensity decay expands the range of concentration of glucose where these probes could be used. This is important since a wide range of glucose concentration in blood could be covered and would also be applicable to for other non-medical applications like the food industry for example. The present example also shows that the interaction between the boronic acid and the glucose is reversible and, knowing that the probes do not consume the glucose, this indicates the possibility to make an implantable and long term use sensor with the probes.

TABLE 7

Stability Constant ($K_s$) and Association Constant ($K_D$) for 7 and 8 for an 1:1 Complexion Between the Boronic Acid Group and D-Glucose. Measured in Methanol/Phosphate Buffer pH 7.7 (1:3)

| Properties | Log $K_S$ ($r^2$ : data points) | $K_D$ (mM) |
|---|---|---|
| 7 | | |
| Steady State Intensity | 1.7 (0.993: 7) | 19.3 |
| Mean Lifetime | 2.5 (0.994: 4) | 3.2 |
| Phase Angle | 2.2 (0.993: 5) | 6.1 |
| Modulation | 2.5 (0.999: 6) | 3.4 |
| 8 | | |
| Steady State Intensity | 3.1 (0.998: 12) | 0.79 |
| Mean Lifetime | 4.4 (0.992: 11) | 0.040 |
| Phase Angle | 4.5 (0.996: 10) | 0.032 |
| Modulation | 4.1 (0.995: 7) | 0.079 |

TABLE 8

Intensity Decay Analysis of 7 in Methanol/Phosphate Buffer pH 7.7 (1:3)

| Conc. D-Glu. (mM) | $\tau_1$ (ns) | $\tau_2$ (ns) | $\alpha_1$ | $\alpha_2$ | $\tau_F$ (ns) | $\chi^2$ |
|---|---|---|---|---|---|---|
| 0 | 2.7 | 11.6 | 0.57 | 0.43 | 9.5 | 1.69 |
| 1.7 | 3.0 | 12.0 | 0.45 | 0.55 | 10.5 | 0.63 |
| 8.3 | 3.6 | 12.9 | 0.32 | 0.68 | 11.8 | 1.11 |
| 21.3 | 5.0 | 13.0 | 0.22 | 0.78 | 12.2 | 0.42 |
| 34.2 | 7.0 | 13.7 | 0.29 | 0.71 | 12.6 | 0.37 |
| 59.5 | 12.1 | — | 1.0 | — | 12.1 | 0.94 |
| 90.2 | 12.6 | — | 1.0 | — | 12.6 | 0.5 |

TABLE 9

Intensity Decay Analysis of 8 in Methanol/Phosphate Buffer pH 7.7 (1:3)

| Conc. D-Glu. (mM) | $\tau_1$ (ns) | $\tau_2$ (ns) | $\alpha_1$ | $\alpha_2$ | $\tau_F$ (ns) | $\chi^2$ |
|---|---|---|---|---|---|---|
| 0 | 1.5 | 9.2 | 0.83 | 0.17 | 5.7 | 2.00 |
| 0.066 | 1.5 | 10.3 | 0.70 | 0.30 | 8.1 | 1.50 |
| 0.132 | 1.5 | 11.0 | 0.55 | 0.45 | 9.7 | 1.07 |
| 0.261 | 1.8 | 11.4 | 0.39 | 061 | 10.5 | 0.49 |
| 0.326 | 1.7 | 11.4 | 0.34 | 0.66 | 10.8 | 0.83 |
| 2.24 | 3.2 | 12.0 | 0.11 | 0.89 | 11.7 | 0.28 |
| 3.82 | 11.5 | — | 1.0 | — | 11.5 | 0.61 |
| 10.1 | 11.8 | — | 1.0 | — | 11.8 | 0.29 |

EXAMPLE 5

An additional highly flourescent probe based on a boron-dipyrromethene functionalized with a phenylboronic group was synthesized using techniques well known in the art and based on the following reaction scheme:

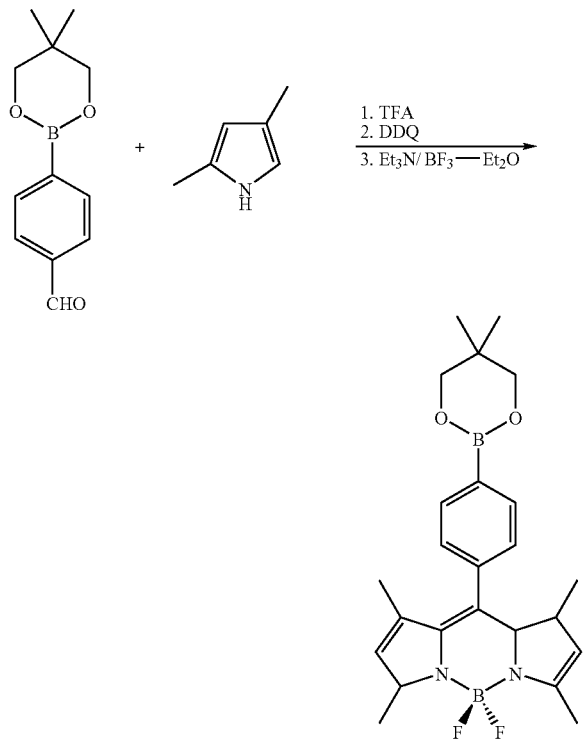

Figure 27A:
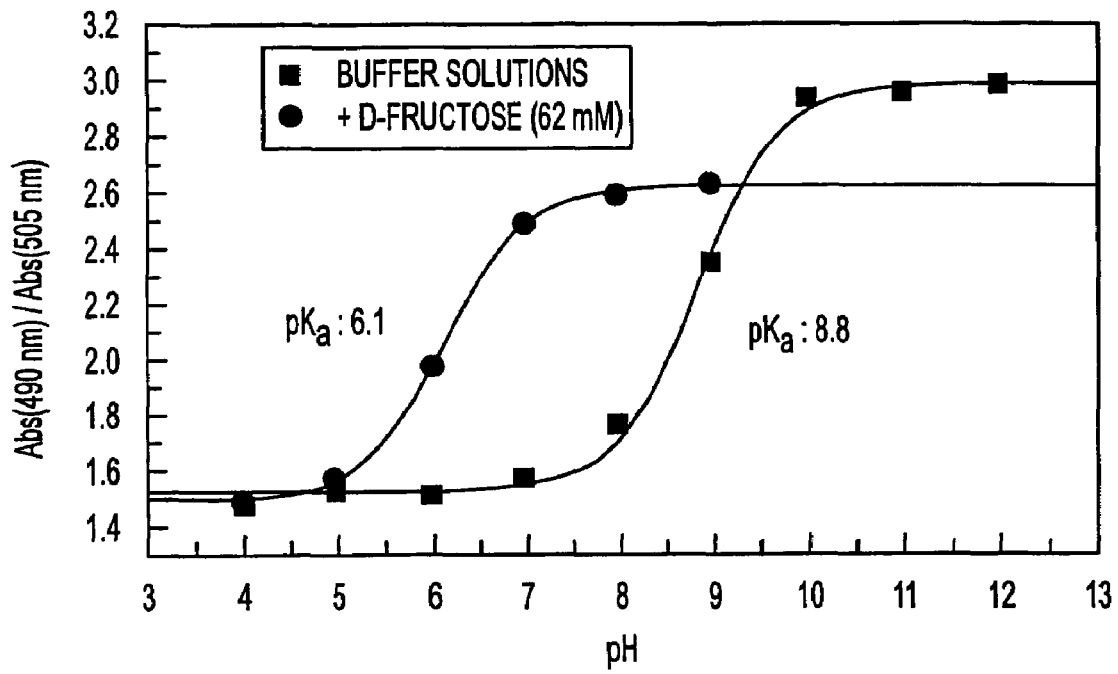
FIG. 27: Titration curves against the pH obtained absorption and fluorescence spectra for a boron-pyrromethene fluorescent probe.
Figure 27B:
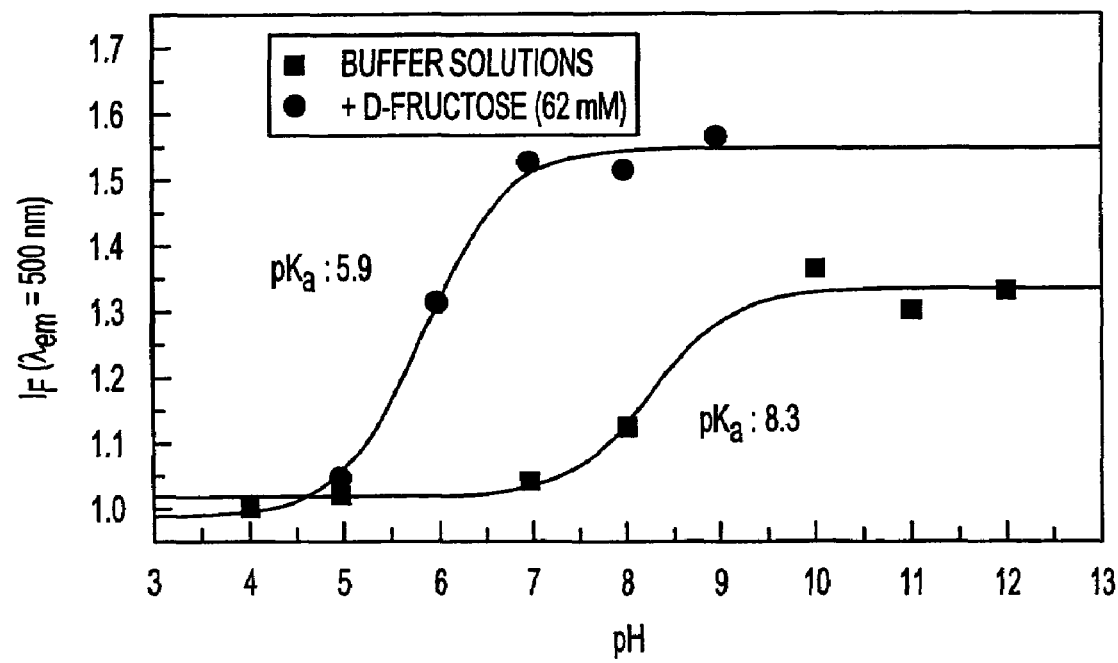

This probe was used directly without deprotection since the hydrolysis is expected to be complete in water and the same effect of sugar is observed with and without the protecting group. Boron-dipyrromethene dyes possess high extinction coefficients, high quantum yields, good photostability, narrow emission band and their building block synthesis allows the development of numerous analogues showing emission ranges from 500-700 nm. Long wavelength fluorescent probes are desirable for transdermal glucose monitoring or whole blood monitoring and narrow emission bands are desirable due to the high signal/noise ratio. The probe of this example exhibits narrow absorption and emission with maxima at 495 nm (need inserts here) and 510 nm (need inserts here) respectively in phosphate buffer, pH 7.5. As the pH increased from 4.0 to 12.0, a blue shift in absorption band with an increase in the absorption coefficient was observed. An isobestic point was observed at 500 nm demonstrating an equilibrium between the neutral and anionic forms of the boronic acid group. FIG. 27 shows titration curves in presence and absence of D-fructose. The pKa of this compound (8.3-8.8) is similar to the general pKa obtained for phenylboronic acid derivatives. In the presence of D-fructose (chosen because it has higher affinity for monoboronic acids in comparison with other sugars) the pH effect gives similar spectral changes in the absorption and emission spectrum. The presence of D-fructose increases changes in the emission spectra and decreases changes in the absorption spectrum.

At pH7-7.5, the probe compound of this example exists under its neutral form while in the presence of sugar it exists under is anionic form. This change thus allows the detection of sugars at neutral pH.

Figure 28A:
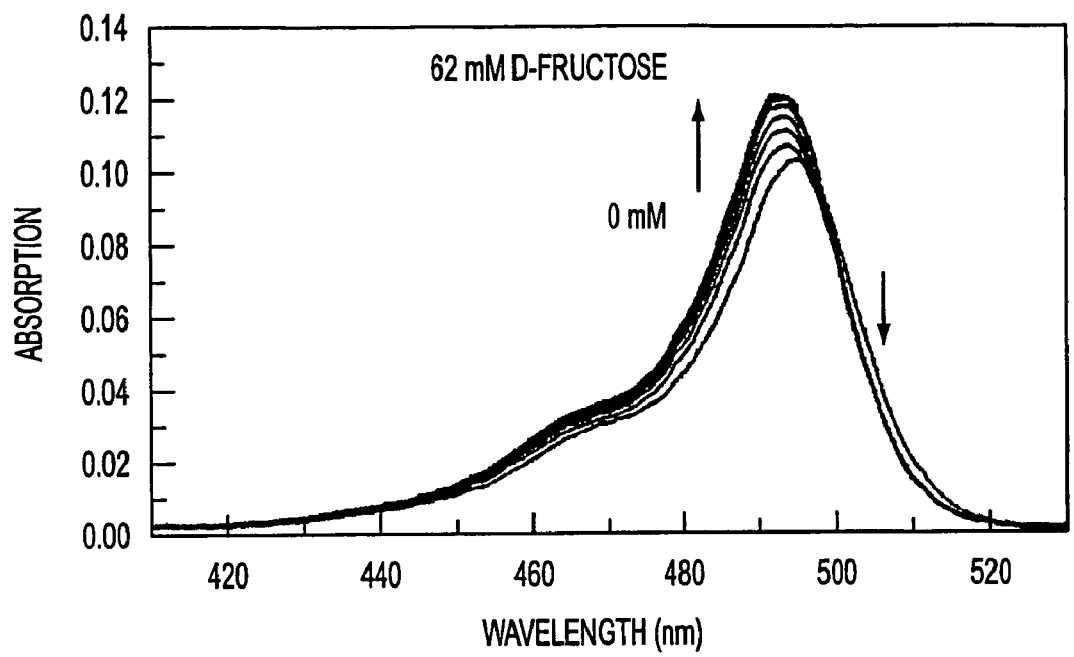
FIG. 28: Effect of fructose on the absorption and fluorescence spectra of a boron-pyrromethene fluorescent probe.
Figure 28B:
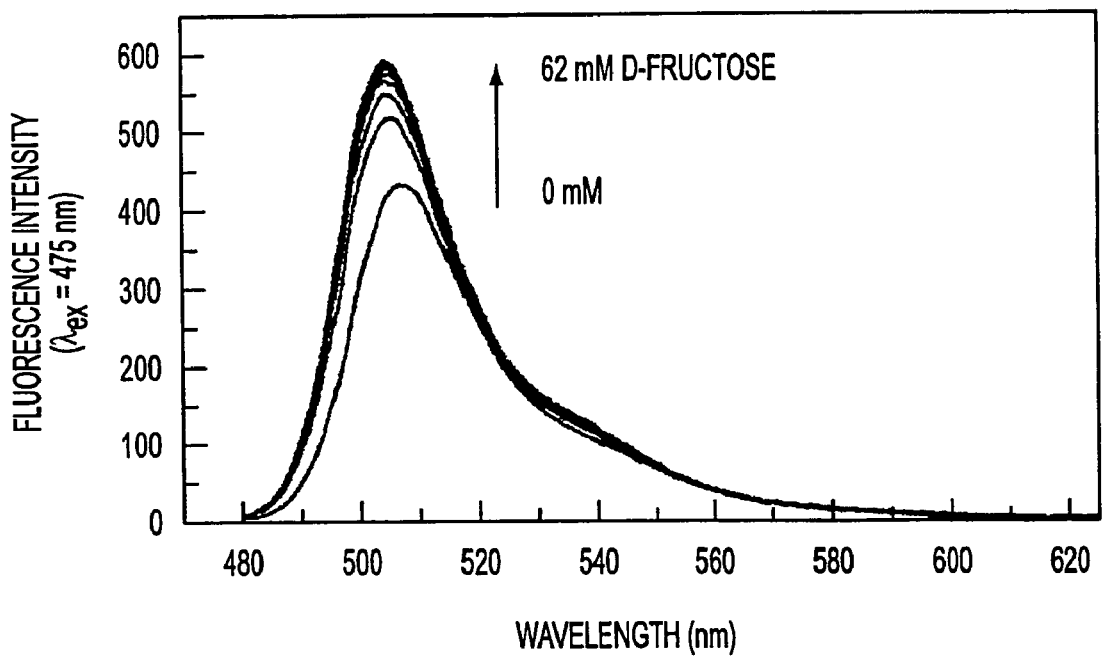
Figure 29A:
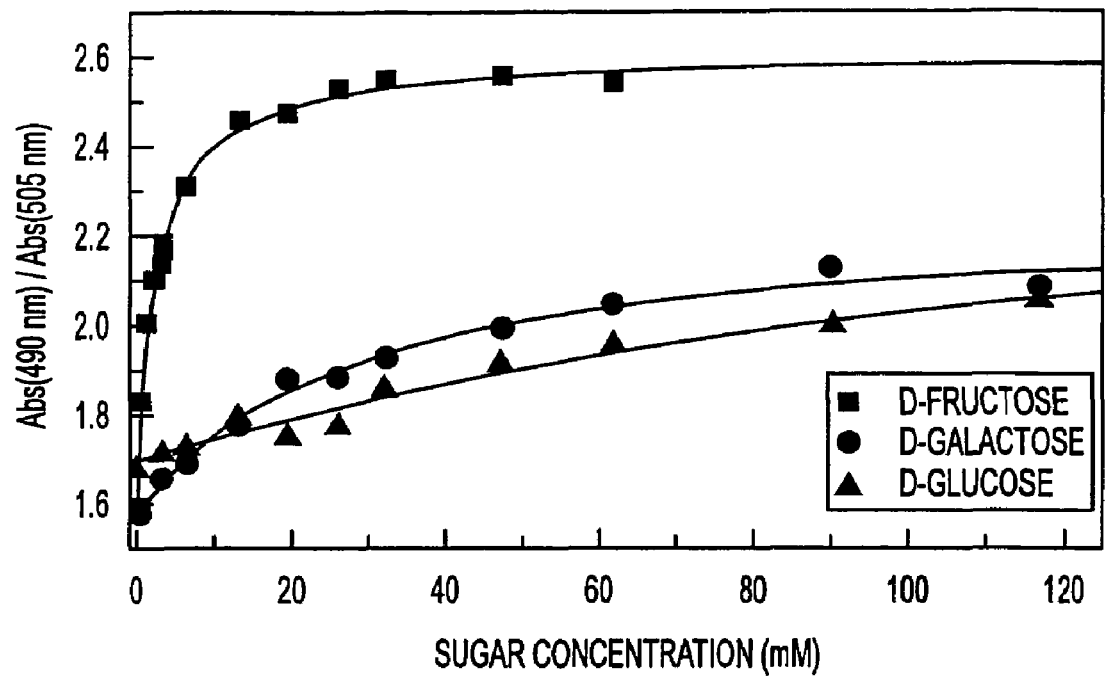
FIG. 29: Titration curves of several sugars for a boron-pyrroinethene fluorescent probe.
Figure 29B:
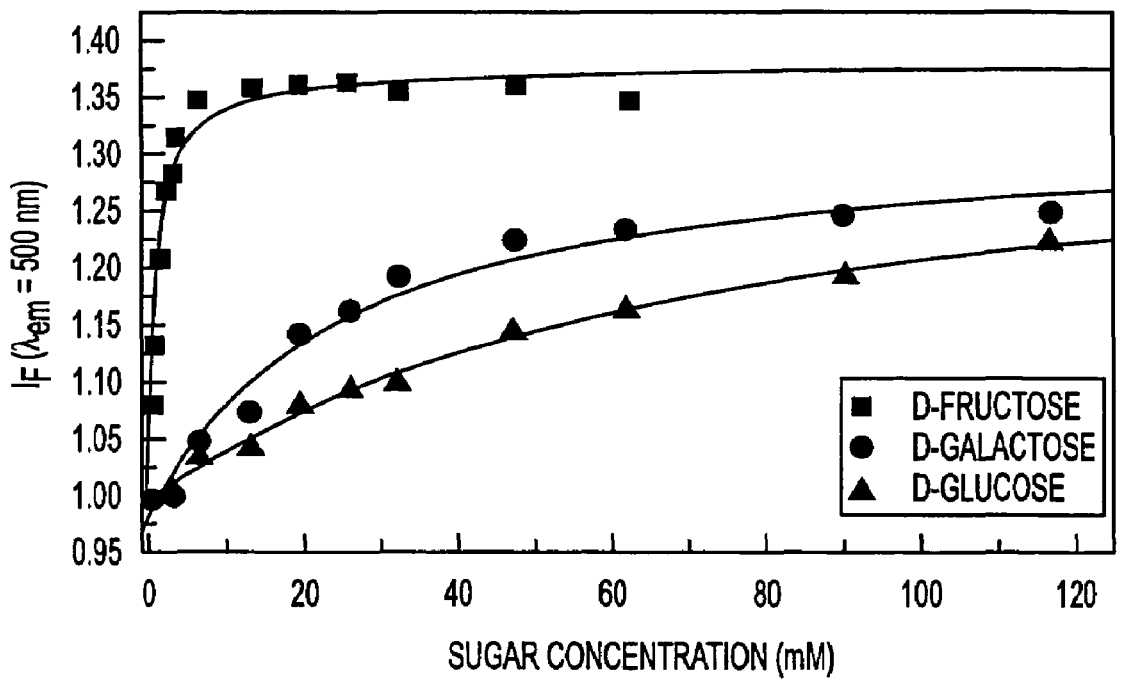

FIG. 28 shows the effects of D-Fructose on absorption and emission spectra of the compound of this example. A blue shift and increase of the absorption coefficient were observed with increases in concentration of sugar. A small blue shift and an increase of the emission were also observed in the emission spectrum. FIG. 29 shows titration curves against D-Glucose, D-fructose and D-galactose. As generally observed for monoboronic acids, the affinity for sugar decreases from D-fructose-D galactose-D-glucose. Dissociation constants are listed in Table 10.

Fluorescence changes were also corroborated by fluorescence decay measurements. Decay profiles did not show changes with pH changes from 4.0 to 12.0 with both measurements showing single exponential decay profiles with a fluorescence lifetime of 3.5 ns. However, significant changes were observed in the presence of D-fructose (62 mM) in phosphate buffer at pH 7.5. The intensity decay remains monoexponential but with a longer (4.1 ns) fluorescence lifetime. The building block nature of this probe and the numerous descriptions in the literature of substituted pyrroles known in the art would allow for numerous modified long wavelength and conjugable fluorescent probes for sugars.

TABLE 10

|  | D-fructose | D-galactose | D-glucose |
|---|---|---|---|
| absorption (mM) | 2.4 | 27 | 130 |
| emission (mM) | 1.0 | 24 | 73 |

Additional General Materials and Methods

D-Glucose, D-galactose and D-fructose were purchased from Sigma and used as received. All solvents used were HPLC grade and purchased from Aldrich. Sodium Dodecyl Sulfate (SDS) was purchase from ICN Biochemicals. Cetyltrimethylamrnonium bromide (HDTBr) was purchased from Sigma. 9-[[N-Methyl-N-(o-boronobenzyl)amino]methyl]anthracene (7) and 9,10-Bis[[N-methyl-N-(o-boronobenzyl)amino]methyl]anthracene (8) were synthesis according to the procedure describe in the literature (33).

Steady-state fluorescence measurements were performed in 1 cm quartz cuvette in an ISS spectrofluorometer.

Frequency-domain (FD) measurements were performed using instrumentation described previously (65). The Domain (TD measurements can also be applied to the fluorescent compounds and methods of the present invention, as readily recognized by those of ordinary skill in the art. For Example 4, an amplitude modulated UV-LED was use as light source given and peak intensity centered around 370 nm. Emission was observed through a 415 nm cut-off and a 420 nm interference filter. The FD or TD intensity decay data were analyzed by nonlinear least squares in terms of the multiexponential model:

$$I(t) = \sum_i \alpha_i \exp(-t/\tau_i),$$

where $\alpha_i$ are the preexponential factors associated with the decay time $\tau_i$, with $\Sigma_i \alpha_i = 1.0$. The mean lifetime is given by:

$$\bar{\tau} = \frac{\sum \alpha_i \tau_i^2}{\sum \alpha_i \tau_i} = \sum f_i \tau_i,$$

where $f_i$ are the fractional steady-state intensities of each lifetime component:

$$f_i = \frac{\alpha_i \tau_i}{\sum_j \alpha_j \tau_j},$$

The intensity-weighted lifetime is given by:

$$\langle \tau \rangle = \sum_i a_i \tau_i$$

The values of (τ) are thought to be proportional to the quantum yield of the sample. For all measurement, the O.D. of the samples does not exceed 0.1 and solutions are stir to avoid any aggregation. Stability and association constants are determined according to the method described in the literature [40].

Stilbene-4-boronic acid (STBA), 4'-cyanostilbene-4-boronic acid (CSTBA), 4'-methoxystilbene-4-boronic acid (MSTBA) and 4'-(dimethylamino)stilbene-4-boronic acid (DSTBA) were synthesized by the Wittig reaction between the para-substituted benzaldehydes and the para-boronic acid derivative of the benzyltriphenylphosphonium bromide. This latter was synthesized by the reaction of the p-bromomethylphenylboronic acid with triphenylphosphine in toluene. All compounds were purified by recrystalization in methanol and all NMR spectra were consistent with the structure and showed only the presence of the trans conformation. Absorption spectra were recorded with a Cary 50 UV-Vis spectrophotometer from Varian. Emission spectra were recorded with a Varian Eclipse spectrofluorometer from Varian. In both cases, the measurements were taken at room temperature in a 1 cm quartz cuvette. For all measurements, the absorbances of the solutions were about 0.1 corresponding to a concentration range of $2-3 \times 10^{-6}$ M of the fluorophore. Fluorescence quantum yields were measured against p-quaterphenyl in cyclohexane ($\phi_F$=0.89) [27] for trans-stilbene (ST) and STBA, anthracene in cyclohexane ($\phi_F$=0.36) for CSTBA and MSTBA and Quinine sulfate in 1N sulfuric acid ($\phi_F$=0.577) for DSTBA.

Titration curves against pH were measured in buffer solutions: acetate buffer for pH 4.0-5.5, phosphate buffer for pH 6.0-9.0 and carbonate buffer for pH 10,0-11.0. Titration curves were fitted and $pK_a$ ($pK_a$=-log $K_a$) values were obtained using the equation:

$$I = \frac{10^{-pH} I_{acid} + K_a I_{base}}{K_a + 10^{-pH}} \quad (1)$$

where $I_{acid}$ and $I_{base}$ are the intensity limits in the acid and basic region, respectively. Titration curves against sugar were fitted and dissociation constant ($K_D$) values were obtained using the equation:

$$I = \frac{I_o + I_f K_D^{-1}[C]}{1 + K_D^{-1}[C]} \quad (2)$$

where $I_o$ and $I_f$ are the initial (no sugar) and final (plateau) intensities of the titration curves. All solutions in water and buffer contained also 33.3% (2:1 v/v) methanol to avoid any problem due to the aggregation.

Frequency-domain (FD) measurements were performed using the instrumentation described previously [Lakowicz and Gryczynski]. For Examples 1, 2, 3 and 5 excitation was provided by a rhodamine 6G dye laser at ~305 nm for STBA, CSTBA and MSTBA and by a pyridine 2 dye laser at ~350 nm for DSTBA. Emission was observed through a combination of a cut-off and glass filters to remove scattered and Raman scattered light. The measurements were taken in a 1 cm cuvette with continuously stirring. The frequency intensity profiles were analyzed by nonlinear least squares in terms of the multiexponential model:

$$I(t) = \sum_i \alpha_i \exp(-t/\tau_i) \quad (3)$$

where $\alpha_i$ are the preexponential factors associated with the decay time $\tau_i$, with $\Sigma_i \alpha_i = 1.0$. The mean lifetime is given by:

$$\bar{\tau} = \frac{\sum \alpha_i \tau_i^2}{\sum \alpha_i \tau_i} = \sum f_i \tau_i \quad (4)$$

where $f_i$ are the fractional steady-state intensities of each lifetime component:

$$f_i = \frac{\alpha_i \tau_i}{\sum_j \alpha_j \tau_j} \quad (5)$$

Errors of 0.5 and 0.05 on the phase angle and modulation have been used, respectively.

Preferably, the detectable quality of fluorescence is a detectable spectral change. Such changes include changes in fluorescent decay time (determined by time domain or frequency domain measurement), fluorescent intensity, fluorescent anisotropy or polarization; a spectral shift of the emission spectrum; a change in time-resolved anisotropy decay (determined by time domain or frequency domain measurement), etc. The theory for anisotropy sensing is simple, and is based on the additivity property of anisotropies demonstrated by Jabloński (66)

Exemplary Synthetic Reaction Schemes 2,2-Dimethylpropane-1,3-diyl p-Tolylboronate (A). p-Tolyllboronic acid (9.0 g, 64.2 mmol) and 2,2-dimethyl-1,3-propanediol (8.0 g, 77.0 mmol) were refluxed in toluene (300 ml) with azeotropic removal of water (Dean-Stark) for 3 h. The solvent was removed by rota-vap and the solid was purified by silica gel chromatography using petroleum ether/dichloromethane 50:50 given 13.2 g (~100%) of A as a white powder: $^1$H NMR (CDCl$_3$, 300 MHz) δ 1.02 (6H, s), 2.37 (3H, s), 3.77 (4H, s), 7.18 (2H, d), 7.69 (2H, d).

2,2-Dimethylpropane-1,3-diyl[-(Bromomethyl)phenyl] boronate (B). A (3.2 g, 15.7 mmol), recrystallized N-bromosuccinimide (3.1 g, 17.4 mmol) and 2,2'-azobis(2-methylpropionitrile) (50 mg, 0.3 mmol) in carbon tetrachloride (100 ml) were refluxed and irradiated with a 100 W lamp for 2 h. The succinimide was removed by filtration and the solvent removed by rota-vap. The white solid was then chromatographed on silica gel with dichloromethane as solvent to give 4.95 g (~100%) of B as a white solid: $^1$H NMR (CDCL$_3$, 300MHz) δ1.02 (6H, s), 3.77 (4H, s), 4.50 (2H, s), 7.38 (2H, d), 7.78 (2H, d).

2,2-Dimethylpropane-1,3-diyl [p-Boronotolyl]Triphenylphosphonium bromide (C). B (4 g, 14.1 mmol) and triphenylphospine (5.2 g, 19.8 mmol) in toluene (75 ml) were refluxed for 12 h. in a 500 ml flask. The mixture was cooled on ice and the product was colected by filtration and dry to give 3.28 g (42.6%) of C as a white powder: 1H (CDC$_3$, 300MHz) δ0.88 (6H, s), 3.34 (4H, s), 5.05 (2H, s), 7.00 (2H, d), 7.7 (15H, m), 7.93 (2H, d).

1-(p-Dimethylaminophenyl)-4-(p-boronophenyl)-buta-1, 3-diene (4). C (250 mg, 0.46 mmol) and 4-(dimethylamino) cinnamaldehyde (88 mg, 0.50 mmol) in dichloromethane (2 ml) were vigorously stirred with a magnetic bar in a 100 ml flask. 2 ml of NaOH/water 50% was then added and the vigorously stirring was continued for 15 min. About 10 ml of dichloromethane and 50 ml of water were added and the pH was reduced to 6-7 by addition of conc. HCl. The mixture was than extracted with CH$_2$CL$_2$, the organic phase was dried over magnesium sulfate and the solvent removed by rota-vap. The crude product was chromatographed on silica gel using toluene/dichloromethane 75/25 (v/v) as solvent, the product comes out at the third band. Further purification by recrystallization from methanol was use to obtained a pure yellow solid: 1H NMR (CDCl$_3$, 300 MHz) δ0.82 (6H, s), 2.99 (6H, s), 3.78 (4H, s) 6.6 to 7.8 (12H, m). The protecting group can be removed by mixing the solid obtained in a mixture of THF/water for ~15 min and, after evaporation of the solvent, chromatographed on silica gel using methanol as solvent. Spectral characteristics of the protected and unprotected compound are the same for all measurement and then this step can be skipped.

1-(p-dimethylaminophenyl)-6-(p-boronophenyl)-hexa-1, 3,5-triene (5). As for 4 except that C and t,t-5-[4-(dimethylamino)phenyl]-2,4-pentadienal were used. The crude product was chromatographed on silica gel using dichloromethane/acetone 98:2 as solvent. The compound comes out at the second band. Further purification by recrystallization from methanol was use to obtained a pure yellow solid: 1H NMR (CDCl$_3$, 300 MHz) δ1.03 (6H, s), 2.98 (6H, s), 3.77 (4H, s) 6.3 to 7.9 (14H, m).

BIBLIOGRAPHY

1. J. P. Lorand, J. O. Edwards, J. Org. Chem. 24 (1959) 769.[1] Elschenbroich, C.; Salzer, A. Organometallics; VCH: New York, 1989.
2. James, T. D.; Sandanayake, K. R. A. S.; Shinkai, S. *Nature* 1995, 374, 345.
3. N. DiCesare and J. R. Lakowicz, *J. Phys. Chem.*, 2001, 105, 6834.
4. N. DiCesare and J. R. Lakowicz, *J. Photochem. Photobiol. A*, 2001, 143(1) 9.
5. Shiino, D., Kataoka, K., Koyama, Y., Yokoyama, M., Okano, T., and Sakurai, Y (1994) *J. Intelligent Mater. Syst. & Struct.* 5, 311-314.
6. Kitano, S., Koyama, Y., Kataoka, K., Okano, T., and Sakurai, Y. (1992) *J. Control. Release* 19, 162-170.
7. Robinson, M. R., Eaton, R. P., Haaland, D. M., Koepp, G. W., Thomas, E. V., Stallard, B. R., and Robinson, P. L. (1992) *Clin. Chem.* 38(9), 1618-1622.
8. Heise, H. M., Marbach, R., Koschinsky, Th., and Gries, F. A. (1994) *Artif. Organs* 18(6), 439-447.
9. Burmeister, J. J., Chung, H., and Arnold, M. A. (1998) *Photochem. Photobiol.* 67(1), 50-55.
10. March, W. F., Rabinovitch, B., Adams, R., Wise, J. R., and Melton, M. (1992) *Trans. Am. Soc. Artif. Intern. Organ* 28, 232-235.
11. Rabinovitch, B., March, W. F., and Adams, R. L. (1982) *Diabetes Care* 5(3), 254-258.
12. Claremont, D. J., Sambrook, I. E., Penton, C., and Pickup, J. C. (1986) *Diabetologia* 29, 817-821.
13. Yokoyama, K., Sode, K., Tamiya, E., and Karube, I. (1989) *Anal. Chim. Acta* 218, 137-142.
14. Schier, G. M., Moses, R. G., Gan, I. E. T., and Blair, S. C. (1988) *Diabetes Res. Clin. Pract.* 4, 177-181.
15. Clarke, W., Becker, D. J., Cox, D., Santiago, J. V., White, N. H., Betschart, J., Eckenmode, K., Levandoski, L. A., Prusinki, E. A., Simineiro, L. M., Snyder, A. L., Tideman, A. M., and Yaeger, T. (1988) *Diabetes Res. Clin. Pract.* 4, 209-214.
16. Tretnak, W., and Wolfbeis, O. S. (1989) *Anal. Chim. Acta* 221, 195-203.
17. Meadows, D., and Schultz, J. S. (1988) *Talanta* 35(2), 145-150.
18. Tolosa, L., Malak, H., Rao, G., and Lakowicz, J. R. (1997) *Sensors Actuators B* 45, 93-99.
19. Tolosa, L., Gryczynski, I., Eichorn, L. R., Dattelbaum, J. D., Castellano, F. N., Rao, G., and Lakowicz, J. R. (1999) *Anal. Biochem.* 267,114-120
20. D'Auria, S., DiCesare, N., Gryczynski, Z., Gryczynski, I., Rossi, M., and Lakowicz, J. R. (2000) *Biochem. Biophys. Res. Conmm.* 274, 727-731.
21. B. Valeur, Topics in Fluorescence Spectroscopy, JR. Lakowicz ed.; Plenum Press, New York, 1994; pp. 21-48.
22. M. Poenie, C.-S. Chen, New Fluorescence Probes for Cell Biology, B. Herman and J. J. Lemasters ed.; Academic Press, New York, 1993; pp. 1-25.
23. R. P. Haugland, Handbook of Fluorescence Probes and Research Chemicals, Molecular Probes Inc.
24. H. Smacinski, J. R. Lakowicz, Topics in Fluorescence Spectroscopy, J. R. Lakowicz ed.; Plenum Press, New York, 1994; pp. 295-334.
25. H. Smacinski, J. R. Lakowicz, Sensors and Actuators B 29 (1995) 15.
26. J. R. Lakowicz, I. Gryczynski, Z. Gryczynski, J. D. Dattelbaum, Anal. Biochem. 267 (1999) 397.
27. J. H. Hartley, T. D. James, C. J. Wrad, J. Chem. Soc. Perkin Trans. 1 (2000) 3155.
28. Matsumi, N.; Naka, K.; Chujo, Y. *J. Am. Chem. Soc.* 1998, 120, 10776.
29. Corriu, R. J.-P.; Daforth, T.; Douglas, W. E.; Guerrero, G.; Siebert, W. S. *Chem. Commun.* 1998, 963.
30. Matsumi, N.; Naka, K.; Chujo, Y. *Macromolecules* 1999, 32, 4467.
31. Sienkiewicz, P. A.; Roberts, D. C. *J. Inorg. Nucl. Chem.* 1980, 42, 1559.
32. Yoon, J.; Czarnik, A. W. *J. Am. Chem. Soc.* 1992,114, 5874.
33. James, T. D.; Samankumara Sandanayake, K. R. A.; Iguchi, R.; Shinkai, S. *J. Am. Chem. Soc.* 1995, 117, 8982.
34. James, T. D.; Shinmori, H.; Takeuchi, M.; Shiinkai, S. *Chem. Commun.* 1996, 705.
35. Samankumara Sandanayake, K. R. A., James, T. D. James, and Shinkai, S. *Chem. Lett. (*1995), 503-504.
36. Takeuchi, M.; Mizuno, T.; Shinmori, H.; Nakashima, M.; Shinkai, S. *Tetrahedron* 1996, 52, 1195.
37. Appleton, B., and Gibson, T. D. (2000) *Sensors Actuators B* 65(1-3) 302-304.

38. Shouhai, W. W., Gao, S., and Wang, B. (1999) *Org. Lett.* 1(8) 1209-1212.
39. Lee, B. Y.; Wang, S.; Putzer, M.; Bartholomew, G. P.; Bu, X.; Bazan, G. C. *J. Am. Chem. Soc.* 2000, 122, 3969.
40. Lee, B. Y.; Bazan, G. C. *J. Am. Chem. Soc.* 2000, 122, 8577.
41. Suenaga H.; Yamamoto, H.; Shinkai, S. *Pure & Appl. Chem.* 1996, 68, 2179.
42. N. DiCesare and J. R. Lakowicz, *J. Anal. Biochem.*, 2001.
43. Rehm, D.; Weller, A. *Israel J. Chem.* 1970, 8, 259.
44. Lewis, F. D.; Weigel, W. *J. Phys. Chem. A* 2000, 104, 8146.
45. Letard, J.-F.; Lapouyade, R.; Rettig, W. *J. Am. Chem. Soc.* 1993, 115, 2441.
46. Lapouyade, R.; Czeschka, K.; Majenz, W.; Rettig, W.; Gilabert, E.; Ruilière, C. *J. Phys. Chem.* 1992, 96, 9643.
47. Shinmori, H.; Takeuchi, M.; Shinkai, S. *J. Chem. Soc., Perkin Trans.* 2 1996, 1.
48. Yam, V. W.-W.; Kai, A. S.-F. *Chem. Commun.* 1998, 109.
49. Mizuno, T.; Fukumatsu, T.; Takeuchi, M.; Shinkai, S. *J. Chem. Soc., Perkin Trans.* 1 2000, 407.
50. Sandanayake, K. R. A. S.; James, T. D.; Shinkai, S. *Chem. Lett.* 1995, 503.
51. Sananayake, K. R. A. S.; James, T. D.; Shinkai, S. *Chem. Lett.* 1995, 503.
52. D. Myung, D. G. Whitten, J. Phys. Chem. 92 (1988) 2945.
53. A. K. Singh, M. Darshi, S. Kanvah, J. Phys. Chem. 104 (2000) 464.
54. Y. Sonoda, H. Morrii, M. Sakuragi, Y. Suzuki, Chem. Lett. (1998) 349.
55. C. T. Lin, H. W. Guan, R. K. McCoy, C. W. Spangler, J. Phys. Chem. 93 (1989) 39.
56. K. M. Keery, G. R. Fleming, Chem. Phys.Lett. 93 (1982) 322.
57. Z. Diwu, Y. Lu, C. Zhang, D. H. Klaubert and R. P. Haugland, *Photochem. Photobiol.*, 1997, 66, 424.
58. C. M. Suter, S. Schalit and R. A. Cutler, *J. Am. Chem. Soc.*, 1953, 75, 4330.
59. Z. Diwu, C. Beachdel and D. H. Klaubert, *Tetrahedron Lett.*, 1998, 39, 4987.
60. Berndt, K. W., Gryczynski, I., and Lakowicz, J. R. (1990) *Rev. Sci. Instrum.* 61, 1816-1820.
61. Thompson, R. B., Frisoli, J. K., and Lakowicz, J. R. (1992) *Anal. Chem.* 64, 2075-2078.
62. Szmacinski, H., and Lakowicz J. R. (1995) *Sensors and Actuators B* 29, 16-24.
63. Burch, C. L., and Lakowicz, J. R. (1995) *Biophys. J.* 68, 1574-1582.
64. Bambot, S. B., Rao, G., Romauld, M., Carter, G. M., Sipior, J., Terpetschnig, E., and Lakowicz, J. R. (1995) *Biosens. Bioelectron.* 10(6-7) 643-652.
65. Lakowicz, J. R.; Gryczynski, I. *Topics in Fluorescence Spectroscopy*, J. R. Lakowicz ed.; Plenum Press, New York, 1991.
66. Jablonski, A. (1960). On the notion of emission anisotropy, *Bull. Acad. Pol. Sci.* 8:259-264.

What is claimed is:

1. A fluorescent compound which is represented by the chemical formula

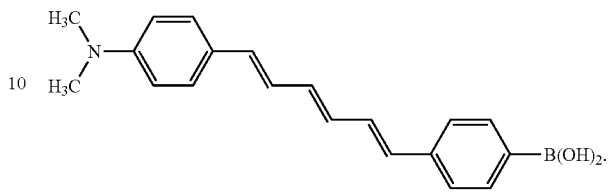

(5)

2. A fluorescent compound which is represented by the chemical formula

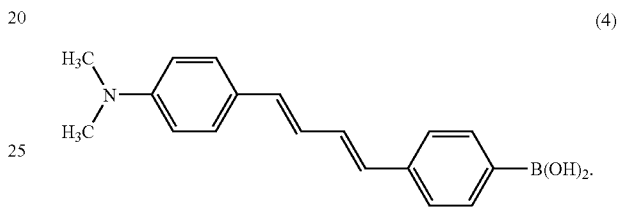

(4)

3. A fluorescent compound which is represented by the chemical formula

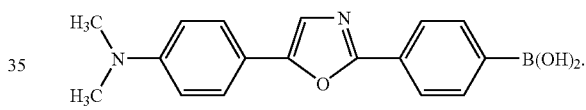

4. A fluorescent compound represented by the chemical formula

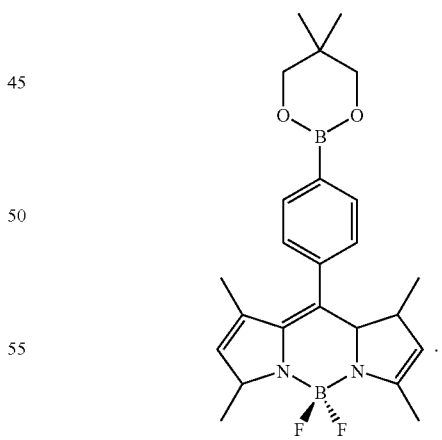

5. A method for detecting the presence or concentration of a diol in a sample which comprises the following steps:
   a) contacting the sample with a probe which comprises the compound of claim 4; and
   b) measuring any change in fluorescence emitted by the probe upon binding of the diol to the probe, thereby detecting the presence or concentration of the diol.

6. The method of claim 5 wherein the diol is a sugar.

7. The method of claim 6 wherein the sugar is selected from the group consisting of glucose, fructose and galactose.

8. The method of claim 5 wherein said change is a change in the intensity of fluorescence of said compound.

9. The method of claim 5 wherein said change is a change in the lifetime of fluorescence of said compound.

10. The method of claim 5 wherein said change is a change in the intensity ratio of said compound.

11. A method as in claim 5 which is performed in vivo in an animal.

12. A method as in claim 5 wherein said measuring step comprises a measurement of the anisotropy or polarization of the fluorescence emitted by the compound.

13. A method as in claim 5 wherein said measuring step comprises a measurement of the anisotropy decay time of the fluorescence emitted by the compound.

14. A method as in claim 5 wherein said measuring step comprises a measurement of the anisotropy correlation time of the fluorescence emitted by the compound.

15. A method as in claim 5 wherein said measuring step comprises a measurement of the anisotropy differential phase angle of the fluorescence emitted by the compound.

16. A method as in claim 5 wherein said measuring step comprises a measurement of the anisotropy modulation ratio of the fluorescence emitted by the compound.

17. A method as in claim 5 wherein said measuring step comprises a measurement of the modulated anisotropy of the fluorescence emitted by the compound.

18. A kit for detecting the presence of a diol in a sample which comprises a compound as in claim 4 and packaging material, and optionally labeling material and instructions for using said compound to detect the presence of the diol.

19. A kit as in claim 18 wherein the compound is bound to a solid support.

* * * * *